United States Patent [19]

Harnisch et al.

[11] Patent Number: 4,695,405
[45] Date of Patent: Sep. 22, 1987

[54] PROCESS FOR QUENCHING FLUORESCENCE, AND NEW CATIONIC OR AMPHOTERIC AROMATIC NITRO COMPOUNDS

[75] Inventors: Horst Harnisch, Much; Edgar Siegel, deceased, late of Leverkusen, Fed. Rep. of Germany, by Gabriele, E. Helena-Maria Siegel, heiress

[73] Assignee: Bayer Aktiengesellschaft, Leverkusen, Fed. Rep. of Germany

[21] Appl. No.: 721,818

[22] Filed: Apr. 10, 1985

[30] Foreign Application Priority Data

Apr. 21, 1984 [DE]  Fed. Rep. of Germany .... 3415103.6

[51] Int. Cl.[4] ............................................. G03C 1/00
[52] U.S. Cl. ........................................ 252/600; 8/102;
       8/568; 8/566; 8/606; 568/924; 568/931
[58] Field of Search ................... 252/600; 8/102, 568,
       8/566, 606; 250/487.1, 488.1; 162/110, 158;
       568/931, 924

[56] References Cited

U.S. PATENT DOCUMENTS

| | | | |
|---|---|---|---|
| 3,542,642 | 11/1970 | Speese et al. | 162/158 |
| 3,639,642 | 2/1972 | Matter et al. | 162/158 |
| 3,790,443 | 2/1974 | Reif | 162/158 |
| 4,098,954 | 7/1978 | Raspanti | 162/158 |
| 4,536,254 | 8/1985 | Falk et al. | 162/158 X |
| 4,584,339 | 4/1986 | Lundberg et al. | 252/2 X |

FOREIGN PATENT DOCUMENTS 2448293  4/1975  Fed. Rep. of Germany .

OTHER PUBLICATIONS

Pajeda, Liet. TSR Aukst. Mokyklu Mokslo Darb. Chem. Chem. Technol. 16, 233–8, 1974.
Lindley et al., J.C.S. Perkin I, pp. 982–994 (1979).
Cook et al., JCS Perkin II, pp. 1293–11, 1301, 1984.
Abdullah et al., J. Photochemistry 28, pp. 61–69, 1985
Beling et al., Chem. Physics 101, pp. 165–173, 1986.

Primary Examiner—John F. Terapane
Assistant Examiner—Catherine Kilby
Attorney, Agent, or Firm—Sprung Horn Kramer & Woods

[57] ABSTRACT

To quench the fluorescence produced by anionic fluorescent brighteners use is made of virtually colorless, water-soluble cationic or amphoteric compounds which contain in the molecule at least one ammonium group, at least two aryl, arylene, hetaryl and/or hetarylene groups and at least one nitro group.

7 Claims, No Drawings

PROCESS FOR QUENCHING FLUORESCENCE, AND NEW CATIONIC OR AMPHOTERIC AROMATIC NITRO COMPOUNDS

The invention relates to a process for quenching the fluorescence produced by anionic fluorescent brighteners through the action of virtually colourless, water-soluble cationic or amphoteric compounds which contain in the molecule at least one ammonium group, at least two aryl, arylene, hetaryl and/or hetarylene groups and at least one nitro group.

Preferred nitro compounds contain in the molecule 2 to 6 ammonium groups, 2 to 12 aryl, arylene, hetaryl and/or hetarylene groups and 2 to 9 nitro groups or, in the case where they are oligomric or polymeric compounds, 1 to 2 ammonium groups, 1 to 3 aryl or arylene groups and 1 to 3 nitro groups per repeat unit. Said groups are bonded to each other either directly or via bridge members. The aromatics can be substituted by non-ionic radicals or by anionic radicals, such as carboxyl or sulpho groups. Therein the total number of cationic groups is equal to or preferably greater than that of the anionic groups. Preference is given to non-ionic substituents.

The nitro groups can be bonded to aliphatic, olefinic, aromatic or cycloaliphatic radicals; but preferably they are bonded to aryl, arylene, hetaryl or hetarylene radicals, each of these radicals having up to 3, preferably up to 2 nitro groups.

Preferred aromatics are aryl and arylene.

Aryl and arylene radicals are for example members of the benzene or naphthalene series, to which can also be fused up to two 5- or 6-membered saturated carbocyclic or heterocyclic rings, such as cyclopentano, cyclohexano, dioxano or tetrahydrofurano.

Examples of suitable hetaryl or hetarylene radicals are the furan, pyran, thiophene, pyrrole, pyrazole, oxazole, thiazole, 1,2,4-oxadiazole, 1,3,4-oxadiazole, 1,3,4-thiadiazole, imidazole, 1,2,4-triazole, pyridine, pyrimidine, pyrazine and s-triazine radicals. These rings can be condensed with one another or can be fused with 1 or 2 benzene rings, such as, for example, the indol-3-yl, carbazol-2- or -3-yl, benzothiazol-2-yl, quinol-3-yl, dibenzofuran-3-yl, dibenzothiophene-S-dioxide and 9-H-thioxanthene-S-dioxide (3,6) radicals. In the case of the benzo-fused heterocyclics, the nitro groups are advantageously on the benzene ring.

These rings and ring systems, in addition to the nitro group, can carry a further 1 to 4 non-ionic substituents, such as $C_1$–$C_4$-alkyl, halogen, such as chlorine, bromine and fluorine, hydroxyl, $C_1$–$C_4$-alkoxy, cyano, carbamoyl, sulphamoyl, $C_1$–$C_4$-alkoxycarbonyl, $C_1$–$C_4$-alkylsulphonyl and trifluoromethyl and additionally an acid group, in particular a sulpho group.

The ammonium groups can be bonded to the molecule in terminal positions or they can constitute a bridge member. They can be incorporated acyclically or as ring members in saturated, partially saturated or hetero-aromatic rings. It is also possible for two such cyclammonium groups to belong to a bis-cationic piperazine or triethylenediamine ring.

Examples of saturated cyclammonium groups are piperazinium, morpholinium, piperidinium and pyrrolidinium radicals, and examples of partially saturated imidazolinium and tetrahydropyrimidinium radicals and of hetero-aromatics are pyridinium, quinolinium, imidazolium and thiazolium radicals.

Examples of acyclic ammonium groups are trialkylammonium, tetraalkylammonium, N,N,N-trialkyl-N-arylammonium, N,N,N-trialkyl-hydrazinium, N,N,N-trialkyl-N-hydroxylammonium, amidinium, guanidinium and thiuronium radicals. The ammonium groups can form inner salts, and be for example in the form of $-N^{\oplus}-O]^{\ominus}$-compounds.

Preferable acyclic ammonium groups have the formulae

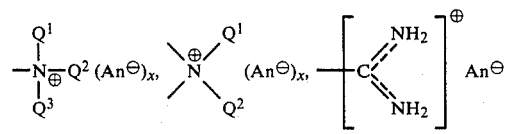

and

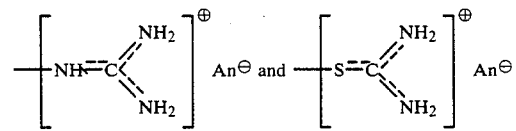

wherein
$Q^1$, $Q^2$ and $Q^3$ stand for hydrogen, $C_1$–$C_4$-alkyl, which can be substituted by OH, $NH_2$, $C_1$–$C_4$-alkoxy, halogen, $CONH_2$, CN, COOH or $C_1$–$C_4$-alkoxycarbonyl, $C_2$–$C_4$-alkenyl, cyclohexyl, phenyl-$C_1$–$C_3$-alkyl or benzoylmethyl which can each be ring-substituted by nitro, $C_1$–$C_4$-alkyl, $C_1$–$C_4$-alkoxy, chlorine or bromine,
$Q^1$ also stands for $-O]^{\ominus}$,
$An^{\ominus}$ stands for a colourless anion and
x stands for 0 or 1.
Preferable cyclammonium groups have the formulae

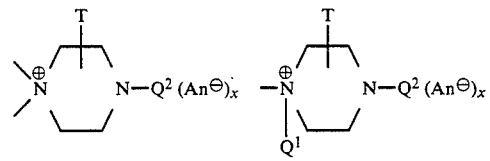

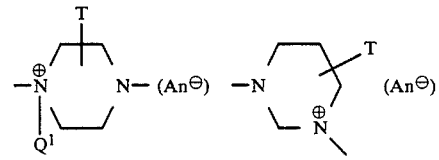

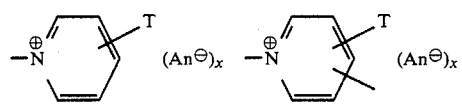

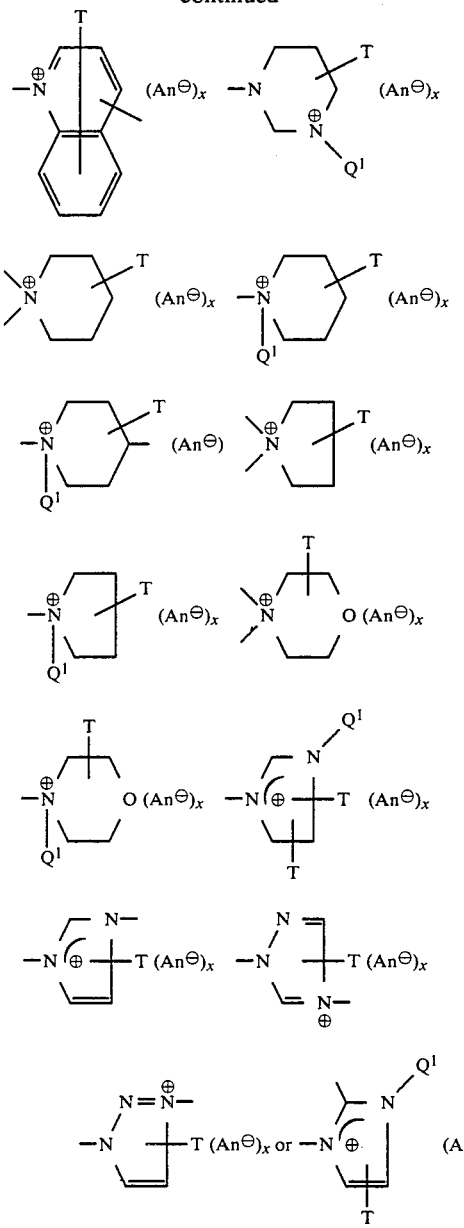

wherein
T stands for H or—depending on the nature of the ring—1–4 methyl groups and x, $An^\ominus$, $Q^1$ and $Q^2$ have the abovementioned meaning.

Particular preference is given to quaternary ammonium groups, that is to say ammonium groups formed not by protonation but by alkylation or aralkylation of a tertiary nitrogen atom ($Q^1 \neq H$).

Suitable anions are the customary colourless inorganic or organic water-solubilising anions, such as chloride, bromide, iodide, chlorozincate, tetrafluoroborate, sulphate, hydrogen sulphate, methosulphate, ethosulphate, benzenesulphonate, p-toluenesulphonate, methylsulponate, amidosulphonate, nitrate, hydrogen phosphate, methylphosphonate, acetate, lactate, formate, maleate, succinate, citrate, tartrate and oxalate.

Suitable bridge members which bond the (het)aryl(ene) groups to one another or to the ammonium groups are bridge members which are stable under application conditions, that is to say for example which are not hydrolysed in water. They are as a rule bidentate or tridentate and in rare cases even tetradentate.

The bridge members can be acyclic and cycloaliphatic. Examples thereof are: —O—, —S—, —$NR^5$—,

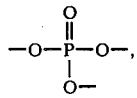

—CO—, —SO—, —$SO_2$—, —COO—, —$CONR^5$—, —$CONR^5$—NH—, —NH—CO—$NR^5$—, —$SO_2N$-$R^5$—, $$-\underset{|}{C}H-,\ -\underset{|}{\overset{|}{C}}-,$$

$C_1$–$C_7$-alkylene which can be straight-chain or branched, —O—$C_1$–$C_4$-alkylene—O—, $$-O-\overset{\overset{O}{\|}}{\underset{\underset{O-}{|}}{P}}-O-,$$

—CH=CH—, 5- or 6-membered saturated isocyclic or heterocyclic rings, in particular 1,4- or 1,1-cyclohexylene. $R^5$ stands for hydrogen, $C_1$–$C_4$-alkyl, $C_3$- or $C_4$-alkenyl, phenyl, benzyl or cyclohexyl.

Said hydrocarbon radicals can also form a common bridge together with one or two of the remaining bridge members.

Non-chromophoric bridge members which have been found to be suitable in the chemistry and application of cationic substantive dyestuffs are also very suitable for use as bridge members in the cationic and amphoteric nitro compounds of the process according to the invention.

The water solubility of the compounds is as a rule at least 1 g/l at 20° C.

A group of compounds which are preferably used for quenching fluorescence have the formula

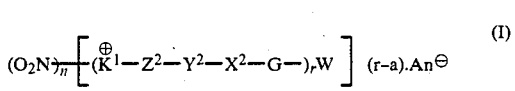 (I)

wherein
$\oplus K^1$ stands for $\oplus E^1$— or A—$X^1$—$Y^1$—$Z^1$—$E\oplus$—, A stands for a benzene, biphenyl, naphthalene, furan, benzofuran, thiophene, benzothiophene, thiazole, benzothiazole, benzimidazole, 1,3,4-thiadiazole or indole radical which, in addition to nitro, can also be substituted by $C_1$–$C_4$-alkyl, halogen, carbamoyl, sulphamoyl, cyano, hydroxyl, $C_1$–$C_4$-alkoxy or a sulpho group, $X^1$ stands for —$(CH_2)_t$—CO—, —$CH_2$—$Y^1$—CO—, —$(CH_2)_t$—$SO_2$—, —O—$CH_2$—CO—, —O—$CH_2$—$SO_2$—, —S—$CH_2$—CO—, —S—$CH_2$—$SO_2$— or a single bond, t stands for 0, 1 or 2, $X^2$ stands for —CO—, —CO—NH—CO—, —SO$_2$— or a single bond, $Y^1$ and $Y^2$ each stand for —O—, —S—, —N(R)—, —N(R)—NH— or a single bond, R stands for hydrogen, $C_1$-$C_2$-alkyl or cyanoethyl or, in $Y^1$ and $Y^2$, also for —CO— or —SO$_2$—, each of which can be bonded to the o- or periposition of A or of a benzene ring W, $Z^1$ and $Z^2$ each stand for $C_1$-$C_6$-alkylene, p-benzylene, p-xylylene or a single bond, $E^\oplus$ stands for —$^\oplus$N($R^1R^2$)—,

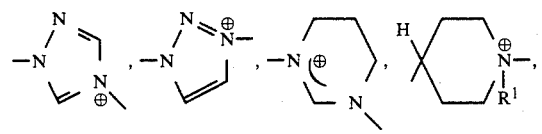

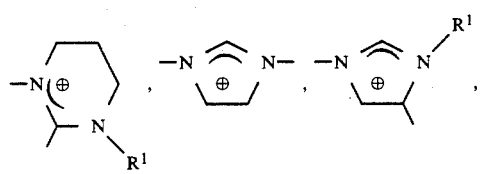

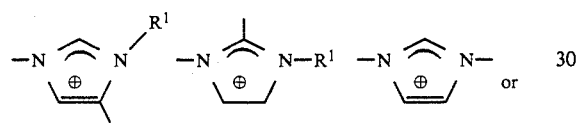

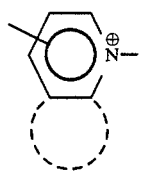

wherein
these rings can be optionally substituted by 1-4 methyl groups, and each of the two free valencies can be bonded to —$X^1$—$Y^1$—$Z^1$— or to —$Z^2$—$Y^2$—$X^2$—G—, $\oplus E^1$ stands for —N$^\oplus$($R^1R^2R^2$),

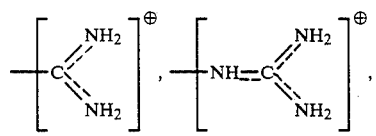

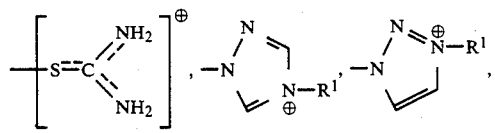

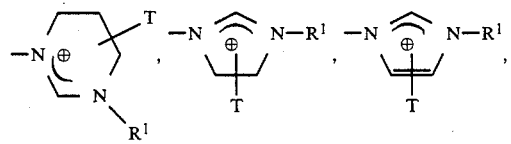

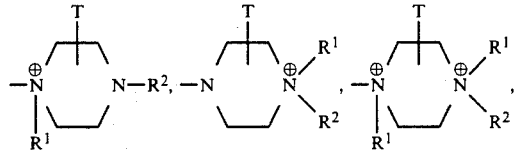

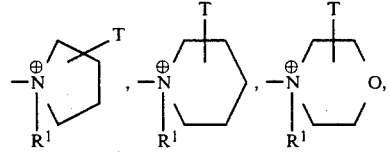

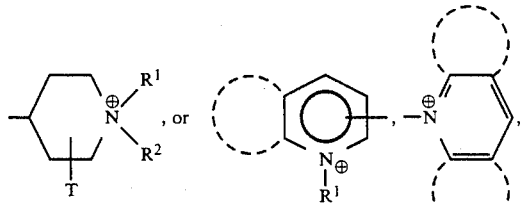

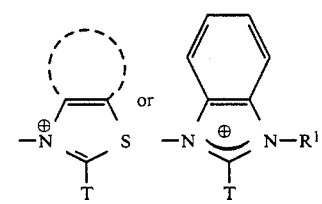

T stands for hydrogen or—depending on the nature of the ring—for 1-4 methyl groups, wherein
the aromatic radicals, in addition to 1 or 2 nitro groups, can also be substituted by $C_1$-$C_4$-alkyl, halogen, cyano or carbamoyl and the amidinium, guanidinium and thiuronium radicals can also be substituted by 1-2 $R^2$ radicals, $R^1$ and $R^2$, independently of each other, stand for hydrogen, $C_1$-$C_4$-alkyl, which can be substituted by OH, NH$_2$, halogen, $C_1$-$C_4$-alkoxy, COOH, CONH$_2$, CN or $C_1$-$C_4$-alkoxycarbonyl, $C_2$-$C_4$-alkenyl, cyclohexyl, phenyl-$C_1$-$C_3$-alkyl or benzoylmethyl which, in addition to nitro, can each also be ring-substituted by $C_1$-$C_4$-alkyl, $C_1$-$C_4$-alkoxy, Cl or Br, $R^1$ also stands for —O]$^\ominus$ or A-$X^1$-$Y^1$-$Z^1$-, R and $R^1$ can also be cyclised and then, together with —N—$Z^1$—N— or —N—$Z^2$—N—, form a piperazine radical which is optionally substituted by 1 or 2 methyl groups, or $R^1$ and $R^2$ can also be cyclised and then, together with the nitrogen atom to which they are bonded, form a pyrrolidine, piperidine, morpholine or piperazine ring each of which is optionally substituted by 1 to 4 methyl groups and can be substituted on the second N atom by optionally OH- or NH$_2$-substituted $C_1$- to $C_3$-alkyl, G stands for —NH—, —NH—CH$_2$—, —O— or a single bond, W stands for an r-dentate radical from the group comprising benzene, naphthalene, anthracene, phenanthrene, 9,10-dihydrophenanthrene, cyclohexane, fluoren-9-one(3,6), thiophene(2,5), dibenzofuran(3,6), dibenzothiophene(3,6), dibenzothiophene-S-dioxide(2,7),9-H-thioxanthene-S-dioxide(3,6), carbazole(3,6), 9-H-xanthene-9-one(2,7),9-acridone(2,7), 1,3,4,-oxadiazole(2,5), 1,2,4-oxadiazole(3,5), 1,3,4,-thiadiazole(2,5),s-triazine(2,4,6), piperazine(1,4),1,2-dihydro-1,2,4,5-tetrazine(3,6) or for a radical of the formula

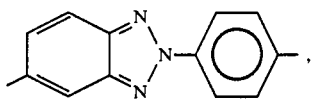

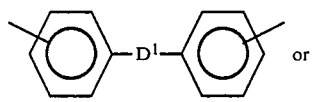  or

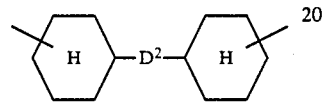

or for the case where —⊕E— denotes a bidentate pyridinium or quinolinium radical also for a single bond, $D^1$ and $D^2$, independently of each other, stand for a straight-chain or branched $C_1$-$C_7$-alkylene radical which is optionally interrupted by —O—, or for —O—$C_2$-$C_4$-alkylene—O—, —O—, —NH—, —N($C_1$-$C_2$-alkyl)—, —CO—, —CO—NH—, —N-H—CO—NH—, 1,1-cyclohexylene or a direct bond, $D^1$ can also stand for —CH($C_6H_5$)—, —CH($C_6H_4$—)—, —N($C_6H_5$)—, —CH=CH—, —S—, —$SO_2$—, —SO—, m- or p-phenylene, thiophene(2,5), 1,3,4-oxadiazole(2,5), 1,3,4-thiadiazole(2,5), oxazole(2,5), thiazole(2,5), 1,2-dihydro-1,2,4,5-tetrazine(3,6) or

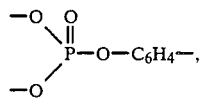

$D^2$ can also stand for —CH($C_6H_{11}$)— or —CH($C_6H_{10}$—)—, where the rings mentioned under W, $D^1$ and $D^2$, in addition to nitrogen, can also be substituted by $C_1$-$C_4$-alkyl, $C_1$-$C_4$-alkoxy, halogen and/or a sulpho group, n stands for an integer from 1 to 6, a stands for the number of anionic and/or ⊕N—⊖O groups and correspondingly for 0, 1, 2 or 3, r stands for 2 or 3 and is ≧ a, and An⊖, if present, stands for a colourless anion, and wherein the chains occurring r times can be identical or different, and wherein in the case of r=2 the grouping

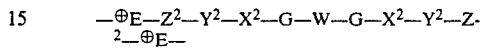

as a whole can also stand for

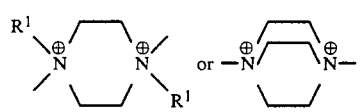

Preference is likewise given to using compounds of the formula

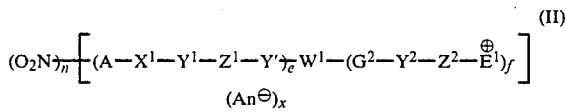

(II)

wherein

Y' stands for —O—, —S—, —NH—, —N(CH_3)— or a single bond, e stands for 1, 2 or, if $W^1$ and/or ⊕$E^1$ as a whole contain at least one nitro group and $W^1 \neq W$, also for 0, f stands for 2 or 3, x, depending on the number of anionic and/or —⊕N—⊖O— groups in the molecule and depending on f, stands for 0, 1, 2 or 3, $W^1$ stands for

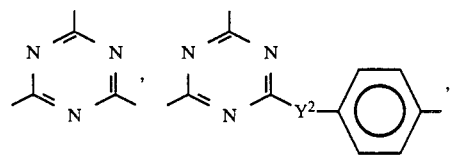

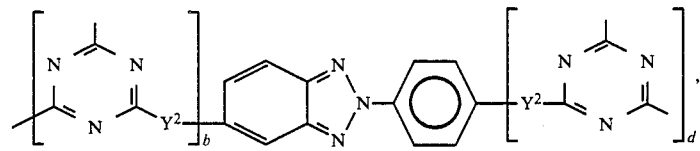

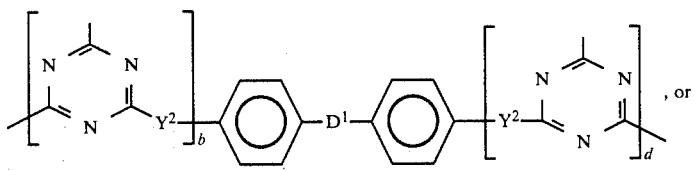

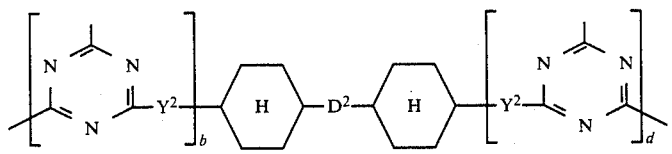

b and d stand for 0 or 1 and
G² stands for —NH—CO— or a single bond and
wherein
n, A, ⊖E¹, X¹, Y¹, Y², Z¹, Z², R¹, R², x and An⊖ have the same meaning as in formula (I).
Y', Y¹ and Y² stand in particular for —N(R)—,
E¹ stands in particular for —⊕N(R¹R²R²), $$-\overset{T}{\underset{R^1}{\overset{\oplus}{N}}}\diagdown, -\overset{\oplus}{\underset{R^1}{N}}\diagdown O, -\overset{\oplus}{\underset{R^1}{N}}\diagdown,$$

$$-N\diagdown\overset{T}{\underset{R^2}{\overset{\oplus}{N}}}\diagup R^1, \diagdown\overset{T}{\underset{R^2}{\overset{\oplus}{N}}}\diagup R^1, \text{ or } -\overset{\oplus}{N}\diagdown$$

wherein
pyridinium, in addition to 1 or 2 nitro groups, can also be substituted by methyl, ethyl, chlorine, bromine, cyano or carbamoyl.

Examples of suitable $C_1$–$C_7$-alkylene radicals D¹ and D², which can also be interrupted by —O—, are —CH₂—, —CH₂—CH₂—, —CH(CH₃)—, —C(CH₃)₂—, —CH₂—CH₂—CH₂—, —CH₂—C(CH₃)₂—CH₂—, —C(CH₃)₂—CH₂—C(CH₃)₂— and —CH₂—CH₂—O—CH₂—CH₂—.

R¹ and R² preferably stand for $C_1$–$C_4$-alkyl which can be substituted by OH, $C_1$–$C_4$-alkoxycarbonyl, CN, carboxyl or carbamoyl, or allyl, benzyl or benzoylmethyl which can each be ring-substituted by 1 or 2 nitro groups.

Halogen is in particular chlorine and bromine.

It is also preferred to use oligomeric or polymeric compounds which contain per repeat unit 1 to 3 nitro groups and 1 or 2 cationic ⊕E¹ groups, ⊕E¹ having the same meaning as in the formula (I), characterised in that they are obtained
  (a) by polymerisation or copolymerisation of one or more monomers from the group comprising maleic anhydride, $$\underset{\underset{Y^1-E^1}{\overset{|}{N}}}{\overset{HC=C-H}{\overset{|}{CO}\diagup\overset{|}{CO}}}, \underset{\underset{Y^1-\overset{\oplus}{E}^1 (An^\ominus)_x}{\overset{|}{N}}}{\overset{HC=C-H}{\overset{|}{CO}\diagup\overset{|}{CO}}},$$

$$CH_2=\underset{R'}{\overset{|}{C}}-CO-Y^1-Z^1-E^1,$$

$$CH_2=\underset{R'}{\overset{|}{C}}-CO-Y^1-Z^1-\overset{\oplus}{E}^1 (An^\ominus)_x,$$

N-allylpyridinium halide or its adducts with a nitrobenzaldehyde, E¹—CH=CH₂, such as 2- or 4-vinylpyridine, and optionally in addition vinyl chloride, vinyl acetate, styrene, α-methylstyrene or 4,4'-divinylbenzene which can each be ring-substituted by methyl, chlorine, E¹—(CH₂)ᵥ, ⊕E¹—(CH₂)ᵥ— and/or nitro,
wherein
  R' stands for hydrogen or methyl,
  E¹ stands for a basic group convertible by reaction with R¹L into —⊕E¹,
  L stands for a group detachable as an anion and
  v stands for 0 or 1 and
  Y¹, Z¹, ⊕E¹, An⊖, x and R¹ have the above-mentioned meaning,
in the event that maleic anhydride is used by further reaction with a compound of the formula HN(R)—Z¹—E¹ or HN(R)—Z¹⊕E¹ (An⊖)ₓ
wherein
  R, Z¹, E¹, ⊕E¹, An⊖ and x have the above-mentioned meaning,
and, if non-cationic E¹ groups are still present, by their further reaction with R¹—L,
wherein
  R¹ and L have the abovementioned meaning, and optionally by subsequent mononitration or dinitration of existing aromatic groups or
  (b) by polycondensation of di-($C_2$–$C_3$-alkylene)-triamines or tri-($C_2$–$C_3$-alkylene)-tetramines of the formula $$H_2N + (CH_2)_k - E \}_w (CH_2)_k - NH_2$$

wherein
  k stands for 2 or 3,
  w stands for 1 or 2 and

E stands for a basic group which can be converted into —⊕E— by reaction with $R^1$—L, with dicarboxylic acids of the formula

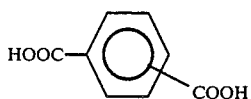

and/or HOOC—$(CH_2)_g$—COOH or their derivatives (such as acid chlorides, anhydrides, lower alkyl esters, hydrochlorides of the imino derivatives of lower alkyl esters or nitriles) wherein g stands for an integer from 0 to 6, and by further reaction with $R^1$—L, wherein $R^1$ and L have the abovementioned meaning, and optionally subsequent mononitration or dinitration of existing aromatic groups.

The number of repeat units in the molecule is about 8 to $8 \times 10^4$, preferably 100 to 5,000. The aromatically bonded nitro groups can be present for example in phenyl radicals of optionally copolymerised styrene, α-methylstyrene or 1,4-divinylbenzene, in any phenylene groups which are present in $Z^1$ or $⊕E^1$ or —⊕E—, preferably as

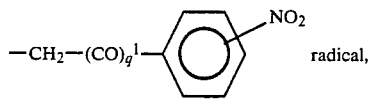

where $q^1 = 0$ or 1, or as substituent in a terephthalic acid or isophthalic acid member.

In examples of suitable starting compounds of the formula

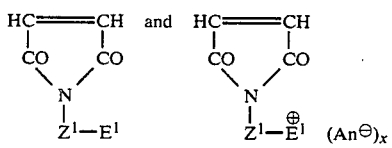

—$Z^1$—$E^1$ or —$Z^1$—$E^{⊕1}$ stands for radicals such as —$(CH_2)_3$—$N(CH_3)_2$, —$(CH_2)_3$—$N^⊕(CH_3)_3$

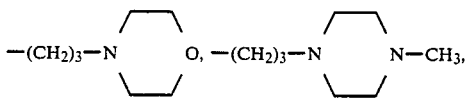

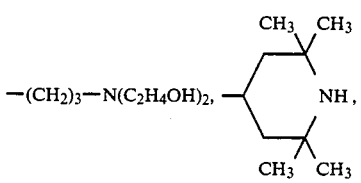

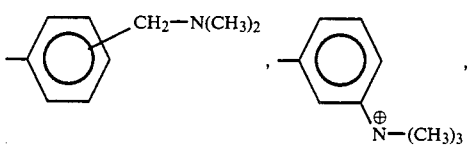

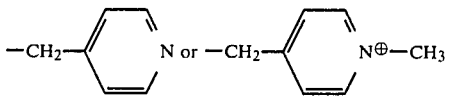

Preferred starting compounds of the formula $$CH_2=C-CO-Y^1-Z^1-E^1$$
$$\quad\quad\;\;|$$
$$\quad\quad R'$$

and

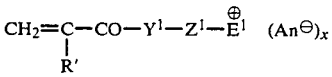

are acrylic or methacrylic acid esters or amides which are bonded via a bridge member $Z^1$ to a basic radical —$E^1$ or a cationic group —$E^{⊕1}$, such as $CH_2=CH-CO-NH-(CH_2)_3-N(CH_3)_2$,

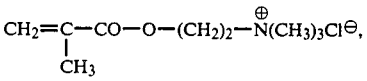

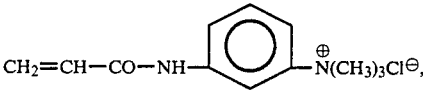

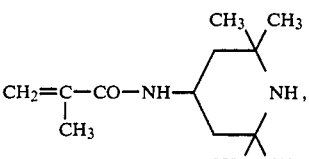

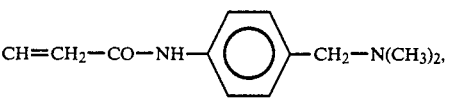

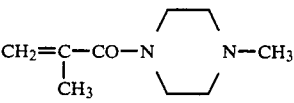

or

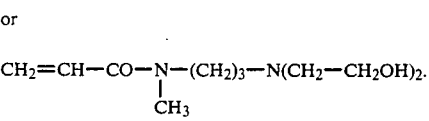

The monomers mentioned under (a) are polymerised or copolymerised in conventional manner, for example at temperatures of 15° to 120° C., preferably 50° to 90° C., in inert solvents, such as ethyl acetate or toluene, in the presence of a polymerisation initiator such as benzoyl peroxide.

The copolymerisation of maleic anhydride with styrene or nitrostyrene can be carried out for example in accordance with No. DE-B-1,495,850 and the further reaction with $HY^1$—$Z^1$—$E^1$, such as N,N-dimethylpropylenediamine, advantageously in accordance with No. DE-B-1,469,727, within the temperature range from 20° to 100° C., preferably without intermediate isolation of the polymeric precursor.

If desired, an amide thus obtained can also be cyclised at 40°–120° C. with acetic anhydride/sodium acetate to give the corresponding imide.

Examples of suitable di-($C_2$–$C_3$-alkylene)-triamines and tri-($C_2$–$C_3$-alkylene)-tetramines are diethylenetriamine, triethylenetetramine, [$H_2N$—($CH_2$))]$_2$N—$CH_3$, dipropylenetriamine and

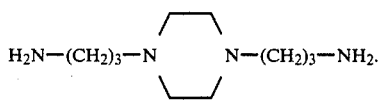

The polycondensation of the dialkylenetriamines and trialkylenetetramines with the dicarboxylic acids or dicarboxylic acid derivatives given under (b), such as terephthalic acid, isophthalic acid and/or adipic acid, is advantageously effected in accordance with Nos. DE-A-1,912,647 and 2,448,293 at temperatures of 150° to 230° C. in an inert high-boiling solvent, such as diethylene glycol or triethylene glycol or a polyglycol mixture, preferably while water is distilled off.

Typical groups L which are detachable as anions are halogen atoms, such as chlorine, bromine and iodine, arylsulphonate radicals, such as benzenesulphonate or p-toluenesulphonate, and methosulphate and ethosulphate.

Examples of suitable compounds $R^1$—L are hydrogen chloride and hydrogen bromide or alkylating agents such as dimethyl sulphate, diethyl sulphate, ethyl p-toluenesulphonate, methyl chloride, ethyl bromide, propyl iodide, n-butyl bromide, ethylene oxide, propylene oxide, aziridine, 3-chloropropyl bromide, 2-methoxyethyl bromide, bromoacetic acid, chloroacetamide, chloroacetonitrile, acrylonitrile, ethyl chloroacetate, allyl bromide, cyclohexyl bromide, benzyl chloride, phenacyl chloride, 3-nitrophenacyl bromide and 4-nitrobenzyl chloride.

The reaction of the polymers mentioned under (a) or of the polycondensates mentioned under (b) with $R^1$—L is advantageously carried out within the temperature range from 20° to 160° C. in an inert solvent analogously to the reaction of (XI) with (X) described hereinafter.

Suitable inert solvents are the same as for the reaction of (IX) with (X). The subsequent nitration of aryl or arylene radicals into polymers described under (a) or into polycondensates described under (b) is advantageously carried out with nitrating agents, in particular with nitric acid or nitric acid/sulphuric acid mixtures, within the temperature range from −5° to 90° C., resulting in preferably 1 or 2 nitro groups entering per aryl or arylene radical.

A particularly preferably employed group of compounds as per (a) contain repeat units of the formula

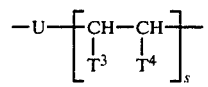 (III)

wherein
U stands for

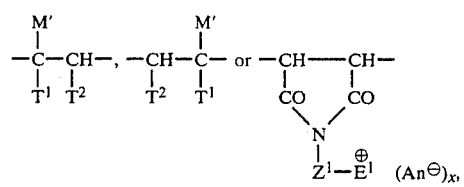

s stands for 0 or 1,
M' stands for hydrogen or methyl,
$T^1$ stands for —CO—N(R)—$Z^1$—$E^{\oplus 1}$ (An$^\ominus$)$_x$ or

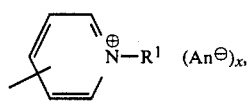

$T^2$ stands for $T^1$, COOH or—where $T^1$ =

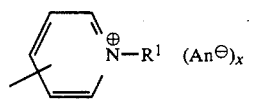

—for hydrogen, and one or the radicals $T^3$ and $T^4$ stands for phenyl, toluyl or chlorophenyl which can each be substituted by nitro and the other stands for hydrogen or methyl,
R, $Z^1$, $E^{\oplus 1}$, An$^\ominus$, x and $R^1$ have the same meaning as in formula (I), the number of sulpho and/or —O]$^\ominus$ groups being equal to or less than that of the cationic charges and wherein 1 to 3 aromatically bonded nitro groups are present per repeat unit.

A particularly preferably employed group of compounds as per (b) contain repeat units of the formula

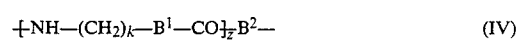 (IV)

wherein
$B^1$ stands
(1) for

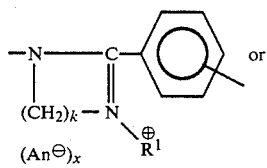

(2) for

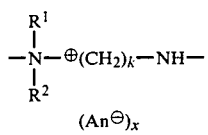

$(An^{\ominus})_x$ $B^2$—if $B^1$ has the meaning given under 1 and $z=0$ or 1—stands for

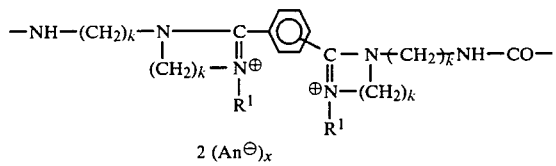

2 $(An^{\ominus})_x$ and—if $B^1$ has the meaning given under (2) and $z=1$—stands for

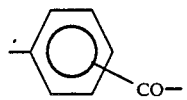

or —$(CH_2)_g$—CO—, k stands for 2 or 3 and g stands for an integer from 0 to 6 and wherein x, $R^1$, $R^2$ and $An^{\ominus}$ have the same meaning as in formula (I), the number of acid and/or —$O]^{\ominus}$ groups is equal to or smaller than that of the cationic charges and wherein 1 to 3, preferably 1 or 2, aromatically bonded nitro groups are present per repeat unit.

Typical anionic fluorescent brighteners are those which are members of the stilbene, distyrylbenzene, distyrylbiphenyl and 1,3-diphenylpyrazoline series, in particular 4,4′-bistriazinylaminostilbene-2,2′-disulphonic acids, 4,4′-bistriazolylstilbene-2,2′-disulphonic acids, naphthotriazolylstilbenemonosulphonic or naphthotriazolylstilbenedisulphonic acids and 4,4′-bis(sulphostyryl)-biphenyl types. They are described inter alia by H. Gold in K. Venkataraman, The Chemistry of Synthetic Dyes, Vol. V, pages 535–678 and in Ullmanns Encyclopädie der technischen Chemie [Ullmann's Encyclopaedia of Chemical Technology] (4th edition), Volume 17, pages 459 to 473. By quenching the blue fluorescence of the anionic whiteners the cationic nitro compounds nullify the white effect of the treated substrates. The process can be carried out in such a way that whitened substrates, such as natural, cellulosic or synthetic substrates, for example natural or regenerated cellulose, pulps or sheets of paper, coatings for paper, silk, wool, jute, hemp and also nylons, or even residues of whiteners are treated with the cationic nitro compounds.

The process according to the invention can also be used for obtaining lighter, brighter shades on cellulose materials by adding the cationic nitro compounds to the dyebath or aftertreating or pretreating the cellulose materials with the compounds. In this way the adverse effect of detergent whiteners on the shade is avoided or nullified.

The process according to the invention is particularly highly suitable for preparing non-brightened paper using whitened paper as the raw material, for the rapid, convenient removal of undesirable residues of brightener-treated paper pulps in paper machines, and for inactivating undesirable residues of aqueous organic, water-miscible solutions or dyeing liquors of anionic whiteners in dyeing apparatus, dyeing machines, stock reservoir vessels and supply lines. These residues are prevented from causing undesirable white effects or fluorescence effects during the subsequent, basically whitener-free application process.

When paper is coated, the cationic or amphoteric nitro derivative can be dispersed in the coating material (such as starch) and in that way be applied to the paper surface through the coating operation.

In the preparation of non-whitened paper from whitener-containing waste paper, after addition to the aqueous suspension of cellulose fibres the cationic or amphoteric nitro derivatives are rapidly absorbed by the fibre, owing to their high substantivity, and thus do not remain behind in the water during the sheet-forming process.

In whitened, completed paper, the white effect can be nullified by impregnating the paper with an aqueous solution of the cationic or amphoteric nitro derivative. This effect can also be used in a controlled manner for producing scriptorial or pictorial recordings or watermarks.

The treatment of fabrics, for example cotton, can be effected in an aqueous medium in conventional manner, for example using the pad-mangle or exhaustion method.

The required amount of cationic or amphoteric nitro compound is about 1–5, preferably 1–3, parts by weight per part by weight of fluorescent brightener. The amount used relative to dry substrate is preferably between 0.05 and 0.3% by weight.

Application is effected for example at pH 3–9.5, preferably pH 4–8.5, at temperatures of 10°–100° C., preferably 18°–60° C., and in particular at room temperature.

Nitro-free fluorescence quenchers are known from Nos. DE-A-1,912,647 and 2,448,293. Compared with those compounds, the compounds of the process according to the invention have a higher and more complete fluorescence-quenching action. The superiority is particularly evident within the neutral or weakly alkaline application range of pH 7–9.5. As a consequence of the fact that lower levels of fluorescence quencher of the process according to the invention produce in practice a complete nullification of the white effect due to the anionic whitener, any anionic whitener subsequently applied to the cellulose substrate to obtain, if desired, an additional white effect is much less impaired than if the pretreatment had been with the state of the art fluorescence quenchers, so that lower whitener levels are sufficient for producing a certain white effect.

The nitro compounds to be used according to the invention are also distinguished by high stability to hydrolysis and light effects and by high solubility in water. Their aqueous formulations are stable to storage, in particular in the presence of carboxamido- or carboximido-containing water-soluble compounds, such as urea, caprolactam, pyrrolidone or cyanamides of the formula

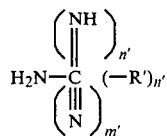   (V)

wherein
R' = —NH—C≡N, —NH—CO—NH$_2$ or —N-H—CO—NH—CH$_3$ and
n' = 0 and m' = 1 or
n' = 1 and m' = 0, as described for example in No. DE-A-3,425,813.2, for example dicyanodiamide.

The invention also relates to compounds
(a) which have the formula I except that $Z^2$ is different from —CH$_2$— when $X^2$, $Y^2$ and G stand for a single bond, r stands for 2 and W stands for phenylene or cyclohexylene,
(b) which have the formula (II),
(c) which have the formula (III) and
(d) which have the formula (IV) and to a process for their preparation.

Of the compounds mentioned above under (a), emphasis as technically particularly useful may be given to those wherein the chains occurring r times are identical and wherein
$K^{\oplus 1}$ stands for A—X$^1$—Y$^1$—Z$^1$—E$^\oplus$— or

A stands for A$^1$ = phenyl, biphenyl or naphthyl which can each, in addition to nitro, also be substituted by C$_1$-C$_4$-alkyl, C$_1$-C$_4$-alkoxy, chlorine, bromine, cyano, carbamoyl or hydroxyl, or thienyl,
X$^1$ stands for X$^{1'}$ = —CO—, —CH$_2$—CO—, —SO$_2$— or a single bond,
Y$^1$ stands for Y$^{1'}$ = —N(R)— or a single bond,
Y$^2$ stands for Y$^{2'}$ = —N(R)— or a single bond,
$E^\oplus$ stands for $E^{\oplus'}$ = —N$^\oplus$(R$^1$R$^2$R$^2$)— or

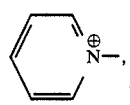

W stands for W' = r-dentate benzene, naphthalene, cyclohexyl, thiophene(2,5) or s-triazine(2,4,6) radical or a radical of the formula

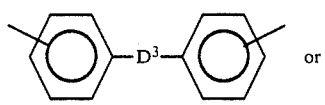 or

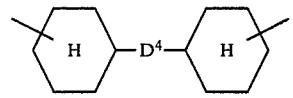, where
D$^3$ = —CH$_2$—, —CH(CH$_3$)—, —C(CH$_3$)$_2$—, —CH=CH—, —CH(C$_6$H$_5$)—, —CH(C$_6$H$_4$—)—, —CO—NH—, —NH—CO—NH—, —N(C$_1$-C$_2$-alkyl)—, —N(C$_6$H$_5$)—, —O—, —S—, —SO$_2$—, 1,1-cyclohexylene, p-phenylene, thiophene(2,5), 1,3,4-oxadiazole(2,5), 1,3,4-thiadiazole(2,5), oxazole(2,5), thiazole(2,5), a direct bond or

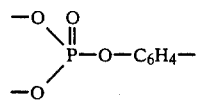

D$^4$ = —CH$_2$—, —CH(CH$_3$)—, —C(CH$_3$)$_2$—, —CH(C$_6$H$_{11}$)—, —CH(C$_6$H$_{10}$—)—, —CO—NH—, —NH—CO—NH—, —O—, 1,1-cyclohexylene or a direct bond, where the rings mentioned under W', D$^3$ and D$^4$ can be substituted by CH$_3$, CH$_3$O, Cl or NO$_2$, and wherein the remaining symbols have the above-mentioned meaning.

Technically particularly useful compounds have the formula

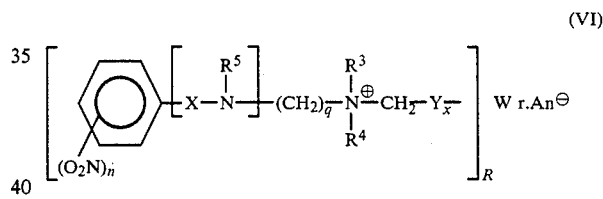   (VI)

and

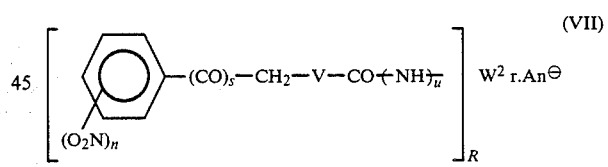   (VII)

wherein
X stands for —CO— or —SO$_2$—,
Y stands for —CO—NH—, —CO—NH—CO—NH— or —CO—,
R$^3$ and R$^4$ stand for C$_1$-C$_4$-alkyl which can be substituted by hydroxyl and
R$^4$ can also stand for a phenyl-C$_1$-C$_2$-alkyl or benzoylmethyl radical which can be substituted by nitro or
R$^3$ and R$^4$ can be cyclised and then, together with the nitrogen atom, form a pyrrolidine, piperidine, morpholine or piperazine ring each of which is optionally substituted by 1 or 2 methyl groups, R$^5$ stands for hydrogen or, together with R$^3$, also for the remaining members of a piperazine ring,
q stands for 2 or 3, or, if s = 0, also for 1,
u stands for 0 or 1,
W$^2$ stands for W or in the case of u = 1 also for a single bond, s stands for 0 or 1,
x stands for 0 or 1,
where x stands for 1 when X stands for CO and W stands for phenylene or cyclohexylene,
V stands for

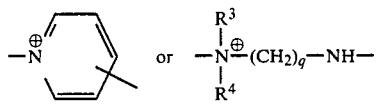

and $An^{\ominus}$, W, n and r have the meaning given in the formula (I).

A further preferred group of nitro derivatives are compounds of the formula

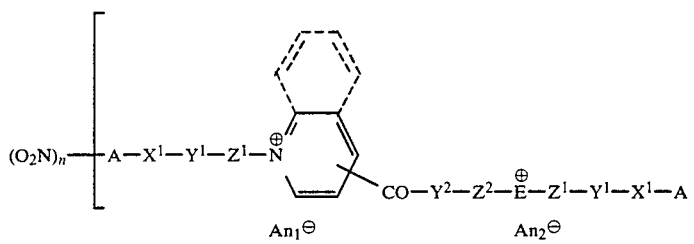

wherein n, A, $X^1$, $Y^1$, $Y^2$, $Z^1$, $Z^2$ and $E^{\oplus}$ have the abovementioned meaning and $An_1^{\ominus}$ and $An_2^{\ominus}$ stand for identical or different colourless anions.

Examples of the radicals $(O_2N)_nA$ are 4-nitrophenyl, 3-nitrophenyl, 3,5-dinitrophenyl, 2-nitrophenyl, 3-nitro-4-methylphenyl, 3-nitro-4-methoxyphenyl, 3-nitro-4-chlorophenyl, 3-methyl-4-nitrophenyl, 4'-nitro-biphenylyl, 2',4'-dinitro-biphenylyl, 3-nitro-5-dimethylaminophenyl, 5-nitronaphth-1-yl, 5-nitronaphth-2-yl, 5,7-dinitronaphth-1-yl, 5-nitrofur-2-yl, 5-nitrothien-2-yl, 6-nitro-benzo[b]fur-2-yl, 5-nitroindol-3-yl, 5-nitrothiazol-2-yl, 6-nitrobenzothiazol-2-yl, 5-nitro-1,3,4-thiadiazol-2-yl and 6-nitroquinol-4-yl.

If R in $Y^1$ stands for CO or $SO_2$, it can be linked to A in the o-position to form $X^1$ or—in the case of a condensed ring system—to the peri-position and then together with $(O_2N)_n$—A—$X^1$—N— form for example the radicals

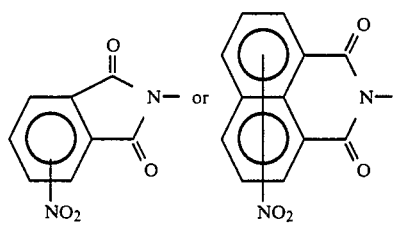

The compounds of the formula (I) are accessible by various methods.

Compounds of the formula $$(O_2N)_nA-X^1-Y^1-Z^1-E \qquad (IX)$$

wherein n, A, $X^1$, $Y^1$ and $Z^1$ have the abovementioned meaning and

E stands for the as yet non-cationic precursor of $E^{\oplus}$, can be reacted in a molar ratio of r:1 with compounds of the formula $$W(-G-X^2-Y^2-Z^2-L)_r \qquad (X)$$

wherein

W, G, $X^2$, $Y^2$, $Z^2$, L and r have the abovementioned meaning.

The reaction is advantageously carried out in an inert organic solvent within the temperature range from 40° to 160° C., requiring a reaction time of about 2–50 hours.

The reaction products (I) are as a rule obtained in the form of crystalline substances. If technically utilisable solutions or dispersions of (I) are desired, the reaction can be advantageously carried out in the solvent concerned, so that the isolation as substance is dispensed with.

Examples of suitable inert solvents are optionally chlorine-, nitro- or lower alkoxy-substituted hydrocarbons, such as benzene, toluene, xylene, mesitylene, chlorobenzene, o-dichlorobenzene, 1,2,4-trichlorobenzene, chlorotoluenes, dichlorotoluenes, nitrobenzene, or anisole, dichloromethane, chloroform, tetrachloromethane, 1,2-dichloroethane, 1,2-dichloropropane, 1,1,2,2-tetrachloroethane, 2-nitropropane, ethers, such as ethylene glycol dimethyl ether, dioxane, tetrahydrofuran, dipolar aprotic solvents, such as dimethylformamide, N-methylpyrrolidone and dimethyl sulphoxide, esters, such as caprolactone, nitriles, such as acetonitrile, solvents which contain polar OH groups, such as ethylene glycol, diethylene glycol, polyglycols, 2-cyanoethanol and water.

Examples of suitable starting compounds of the formula (X) are 1,4-bischloromethylbenzene, 1,4-bisbromomethylbenzene, 2,4-bischloromethyl-1,5-dimethylbenzene, 1,3,5-trischloromethylbenzene, 4,4'-bischloromethylbiphenyl, 1,4-bischloromethylnaphthalene, 2,6-bischloromethylnaphthalene, 4,4'-bischloromethyl-benzophenone, -diphenyl sulphone, -diphenylamine, -N-methyl-diphenylamine, -triphenylamine, -diphenyl ether, -diphenyl sulphide, -diphenylmethane, -triphenylmethane, -diphenylpropane, tris-(4-chloromethylphenyl)-methane, 2,5-bischloromethylthiophene, -1,3,4-oxadiazole, -1,3,4-thiadiazole, N,N',N''-trischloromethyl-s-triazine-2,4,6-trione, the p-toluenesulphonic acid triester of N,N',N''-trismethylolcyanuric acid, 4,4'-bischloroacetamidobenzanilide, 4,4'-bis-(chloroacetamidomethyl)-biphenyl (U.S. Pat. No. 4,370,486), 4,4'-bis-(chloroacetamido)-triphenylmethane, -diphenylmethane or -3,3'-dimethoxybiphenyl, 4,4',4''-tris-(chloroacetamido)-triphenylmethane, 4,4',4''-tris-(chloroacetamido)-triphenyl phosphonate, bis-(4-chloroacetamidocyclohexyl)-methane, 2,2-bis-(4-chloroacetamidocyclohexyl)-propane, 4,4'-bis-chloroacetyldiphenyl ether, 4,4'-bis-chloroacetyldiphenyl sulphide, 4,4'-bis-(chloroacetureido)-diphenylmethane and 4,4',4''-tris-(chloroacetureido)-triphenylmethane (from 4,4',4''-triaminotriphenylmethane and 3 equivalents of chloroacetyl isocyanate).

Compounds of the formula (IX) wherein $Y^1$ stands for —O—, —S—, —N(R)— or —N(R)NH—, R having the above-mentioned meaning, can be prepared by reacting nitro compounds of the formula

 (XI)

wherein

A and $X^1$ have the abovementioned meaning and Hal stands for a halogen atom which is detachable in the form of an anion, such as a chlorine, bromine or iodine atom, with a compound of the formula

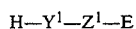 (XII)

wherein $Y^1$, $Z^1$ and E have the abovementioned meaning.

The reaction is advantageously carried out in water and/or an inert organic solvent, such as an optionally halogen- or nitro-substituted aromatic or aliphatic hydrocarbon of the abovementioned type and/or an acyl-transferring reaction medium which is capable of intermediate N-acylations, such as pyridine or picoline mixtures, acetonitrile, dimethylformamide or dimethyl sulphoxide, within the temperature range from about 0° to 110° C.

The proton acceptor used can be the nitrogen atom which is present in (XII) where it is bonded to $Z^1$, $R^1$ and optionally $R^2$ or an additionally employed base, such as sodium hydroxide solution, potassium hydroxide solution, sodium carbonate, potassium carbonate solution, alkali metal bicarbonate solution, magnesium oxide, triethylamine, triisopropanolamine, dimethylaniline, pyridine or picoline mixtures.

Examples of suitable starting compounds of the formula (XI) are 4-nitrobenzenesulphonyl chloride, 4-nitrobenzoyl chloride, 3-nitrobenzenesulphonyl chloride, 3-nitrobenzoyl chloride, 3,5-dinitrobenzoyl chloride, 4-chloro-3-nitrobenzoyl chloride, 4-chloro-3-nitrobenzenesulphonyl chloride, 3,5-dinitro-4-hydroxybenzoyl chloride, 3-carbamoyl-5-nitrobenzoyl chloride, 3-methyl-4-nitrobenzoyl chloride, 4-methyl-3-nitrobenzoyl chloride, 4-methyl-3-nitrobenzenesulphonyl chloride, 4-methoxy-3-nitrobenzoyl chloride, 2-nitrobenzenesulphonyl chloride, 2,4-dinitrobenzenesulphonyl chloride, 4-p-nitrophenylbenzoyl chloride, 4-p-nitrophenylbenzenesulphonyl chloride, p-(2,4-dinitrophenyl)-benzoyl chloride, p-(2,4-dinitrophenyl)-benzenesulphonyl chloride, 5-nitronaphthalene-1-sulphonyl chloride, 5-nitronaphthalene-2-sulphonyl chloride, 4-nitrophenylacetyl chloride, 2,4-dinitrophenoxyacetyl chloride, 2,4-dinitrophenylacetyl chloride, 4-nitrocinnamoyl chloride, 5-nitrothienyl chloride and 1,2-dimethyl-5-nitroindole-3-carbonyl chloride.

In the case where in compound (I) $Y^1$ denotes —N(R)— and R represents a —CO— or —SO$_2$— group which is bonded to A in the o— or peri-position relative to the A—$X^1$ bond, the starting compound used is advantageously not (XI) but the anhydride of the formula

 (XIII)

wherein $X^3$ stands for —CO— or —SO$_2$— and $X^1$, A and n have the abovementioned meaning, which is reacted with (XII). The reaction is carried out at reaction temperatures of about 50°–170° C. in one of the solvents recommended above.

Examples of (XIII) are 3-nitrophthalic anhydride, 4-nitrophthalic anhydride, 4-nitronaphthalic anhydride and 4-nitro-2-sulphobenzoic anhydride.

Examples of suitable starting compounds of the formula (XII) are 1-amino-3-dimethylamino-n-propane, 1-amino-3-diethylamino-n-propane, 1-amino-3-methylamino-n-propane, 1-amino-3-cyclohexylamino-n-propane, 1-amino-2-diethylaminoethane, 1-amino-2,2-dimethyl-3-dimethylamino-n-propane, N,N',N''-trimethyldiethylenetriamine, bis-(3-amino-n-propyl)-methylamine, bis-(3-amino-n-propyl)-amine, diethylenetriamine, 4-amino-1-diethylamino-n-pentane, glycine choline ester, choline β-aminoethyl ether, 2-[(3-amino-n-propyl)-methylamino]-ethanol, 2-(2-aminoethylamino)-ethanol, 2-dimethylaminoethanol, 2-(2-dimethylaminoethoxy)-ethanol, 2-diethylaminoethanol, 2-dimethylamino-2-propanol, 1-diethylamino-2-propanol, bis-(2-hydroxy-n-propyl)-methylamine, 3-dimethylamino-1-propanol, 2-diethylaminoethanethiol, N-(3-amino-n-propyl)-pyrrolidine, N-methyl-N'-(2-aminoethyl)-piperazine, N-methylpiperazine, N-β-hydroxyethylpiperazine, 1-(3-amino-n-propyl)-1,2,4-triazole, 1-(3-amino-n-propyl)-1,2,3-triazole, 1-(3-amino-n-propyl)-imidazole, 4-amino-N,N-dimethylbenzylamine, 4-aminomethyl-N,N-dimethyl-benzylamine and 4-aminomethylpyridine.

In a particularly efficient process variant, compounds of the formula (IX), prepared from (XI) and (XII) or of (XII) and (XIII), are not especially isolated but are converted in the same reaction medium into the free base and then reacted with (X).

A further process for preparing intermediate compounds of the formula (IX), which is particularly suitable for compounds in which $X^1$ denotes —CO—, $Y^1$ denotes a direct bond, $Z^1$ denotes a —CH(Q)—CH$_2$— group, and Q denotes hydrogen or methyl, is characterised in that a nitro compound of the formula

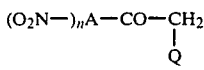 (XIV)

wherein
n, A and Q have the abovementioned meaning, is reacted with formaldehyde and an optically cyclic secondary amine of the formula

H—E (XV)

wherein
E has the abovementioned meaning, under the customary conditions of a Mannich reaction.

The reaction is advantageously carried out within the temperature range from 20° to 130° C. in water and/or in an organic solvent of the abovementioned type in the presence of an equivalent of a strong acid, such as hydrochloric acid or p-toluenesulphonic acid.

Examples of typical starting compounds of the formula (XIV) are 3-nitroacetophenone, 3-nitropropiophenone, 4-nitroacetophenone, 4-p-nitrophenylacetophenone, 3,5-dinitroacetophenone, p-2,4-dinitrophenylacetophenone, 1-acetyl-5-nitronaphthalene, 2-acetyl-5-nitrofuran, 2-acetyl-5-nitrothiophene, 2-acetyl-5-nitro-1,3,4-thiadiazole, 2-acetyl-5-nitrothiazole, 2-acetyl-6-nitrobenzo[b]furan, 2-acetyl-5-nitrobenzo[b]thiophene, 2-acetyl-5-nitrobenzothiazole and 2-acetyl-6-nitrobenzothiazole.

Examples of suitable secondary amines of the formula (XV) are dimethylamine, diethylamine, di-n-butylamine, 2-methylaminoethanol, diethanolamine, pyrrolidine, piperidine, morpholine, N-methylpiperazine, N-β-hydroxyethylpiperazine, 2-methylindoline, tetrahydroquinoline, N-methylaniline, 1,2,3- or 1,2,4-triazole and imidazole.

Here too an efficient process variant comprises not isolating the compound of the formula (IX) thus obtained after conversion into the base and reacting it further with (X) to give (I).

A further process for preparing intermediate compounds of the formula (IX), which is particularly suitable for compounds in which
$Y^1$ denotes a direct bond,
$Z^1$ denotes a —CH$_2$—CH(Q)—V$^1$— group,
$V^1$ denotes a direct bond or a —O—CH$_2$—CH$_2$— group, and
Q denotes hydrogen or methyl,
is characterised in that a nitro compound of the formula

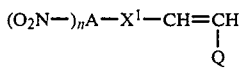 (XVI)

wherein
n, A, $X^1$ and Q have the abovementioned meaning, has added to it a compound

H—V$^1$—E (XVII)

wherein
V$^1$ and E have the abovementioned meaning.

The addition is carried out for example using the methods described in Nos. DE-A-2,534,180 and 2,700,996.

In a further process for preparing compounds of the formula (I), compounds of the general formula

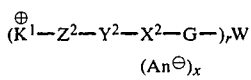 (XVIII)

wherein
$K^{\oplus 1}$, $X^2$, $Y^2$, $Z^2$, G, W, An$^{\ominus}$, x and r have the abovementioned meaning,
are reacted with nitrating agents, in particular with nitric acid or nitric acid/sulphuric acid mixtures.

Depending on the substituents in A and W and the nitrating conditions, 1–3 nitro groups go into $K^{\oplus 1}$ and/or W. The reaction is advantageously carried out within the temperature range from −5° to 90° C.

In analogous manner, the intermediate compounds of the formula (IX) can also be prepared by nitrating precursors which are free of nitro groups.

In a further process for preparing compounds of the formula (I), compounds of the formula (E—Z$^2$—Y$^2$—X$^2$—G—)$_r$W (XIX)

wherein
E, $X^2$, $Y^2$, $Z^2$, G, W and r have the abovementioned meaning,
are reacted in a molar ratio of 1:r with compounds of the formula (O$_2$N—)$_n$A—X$^1$—Y$^1$—Z$^1$—L (XX)

wherein
n, A, $X^1$, $Y^1$, $Z^1$ and L have the abovementioned meaning.

Suitable solvents and reaction conditions are the same as for the reaction of (IX) and (X).

A process for preparing compounds of the formula (VIII) is characterised in that compounds of the formula

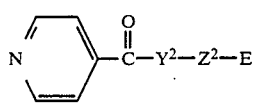 (XXI)

wherein
$Y^2$, $Z^2$ and E have the abovementioned meaning, are reacted in a molar ratio of 1:2 with compounds of the formula (XX).

Suitable solvents and reaction conditions are the same as for the reaction of (IX) with (X).

$N^{\oplus}$—$O^{\ominus}$— compounds are prepared by treating tertiary acyclic or cyclic (N—) or (N) compounds with hydrogen peroxide or peracetic acid. The treatment is advantageously carried out in an inert organic solvent, such as methyl ethyl ketone or glacial acetic acid, within the temperature range from 10° to 60° C., preferably 20° to 40° C.

Compounds of the formula (II) can be prepared, for example, by reacting cyanuric chloride in any order with 1 equivalent of a compound of the formula

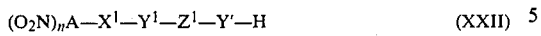
$(O_2N)_n A—X^1—Y^1—Z^1—Y'—H$ (XXII)

wherein
n, A, $X^1$, $Y^1$, $Z^1$ and Y' have the same meaning as in formula (II),
and 2 equivalents of a compound of the formula

$H—Y^2—Z^2—E^{\oplus 1} (An^{\ominus})_x$ (XXIII)

wherein
$Y^2$, $Z^2$, $E^{\oplus 1}$, $An^{\ominus}$ and x have the same meaning as in formula (II).

The reaction can be advantageously carried out in an aqueous medium, preferably in a mixture of a lower aliphatic ketone, such as methyl ethyl ketone, and water in the presence of potassium bicarbonate or sodium bicarbonate as acid acceptor in a first reaction stage at pH 4–4.5 and 10°–20° C., in a second reaction stage at pH 4–6 and 40° C. and in a third reaction stage (replacement of the 3rd chlorine atom of cyanuric chloride) at pH 6–7 and 60°–100° C., for example under reflux.

In other cases, a compound of the formula

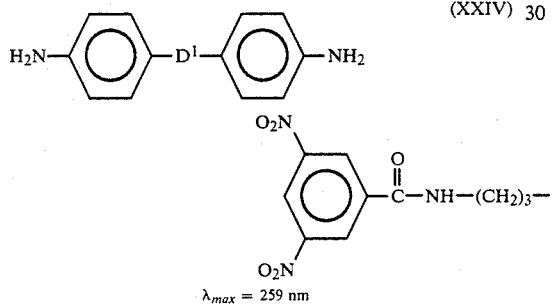
(XXIV)

or

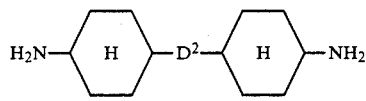
(XXV)

wherein
$D^1$ and $D^2$ have the same meaning as in formula (I), is reacted first with 2 equivalents of cyanuric chloride and then in succession with 2 equivalents of (XXII) and 2 equivalents of (XXIII).

Here too the reaction conditions are advantageously the same as those indicated above.

Intermediate products (XIX) of the special formula

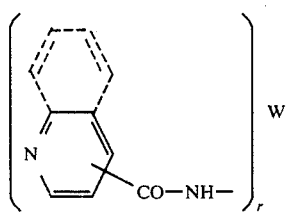
(XXVI)

wherein
r and W have the same meaning as in formula (I), are advantageously prepared by reacting a pyridine or quinolinecarboxylic acid in a molar ratio of r:1 with a diisocyanate or triisocyanate of the formula $(O=C=N)_r W$ in an inert solvent, such as toluene or chlorobenzene, within the temperature range from 90° to 140° C., carbon dioxide being eliminated.

PREPARATION EXAMPLES

Example 1

11.8 g of N-(N,N-dimethylamino-n-propyl)-3,5-dinitrobenzamide and 3.5 g of α,α'-dichloro-p-xylene are heated with stirring at 100° C. in 150 ml of dimethylformamide for 48 hours, and then cooled down. The crystalline precipitate is filtered off with suction, is washed with isopropanol and is dried in a vacuum desiccator. The result is 13.2 g of the compound of the formula

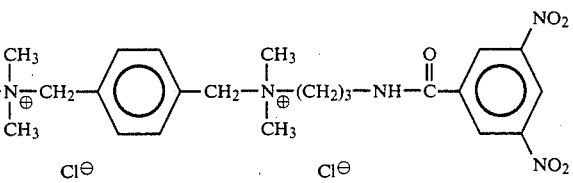
$\lambda_{max} = 259$ nm

The starting N-(N,N-dimethylamino-n-propyl)-3,5-dinitrobenzamide is prepared as follows:

20.4 g of 3-dimethylamino-n-propylamine are added dropwise with cooling and stirring to a suspension of 46.1 g of 3,5-dinitrobenzoyl chloride in 400 ml of anhydrous acetonitrile, the temperature being maintained between 20° and 30° C. Afterwards the mixture is stirred for a further 4 hours. The crystalline precipitate is filtered off with suction, is washed with isopropanol and is dried at 40° C. in vacuo.

The result is 62.1 g of N-(N,N-dimethylamino-n-propyl)-3,5-dinitrobenzamide hydrochloride in the form of colourless crystals (decomposition above 300° C.). To convert it into the free base, all of the hydrochloride is suspended in 450 ml of water, and the suspension is brought to an alkaline pH with 20 g of 45% strength sodium hydroxide solution and is stirred for 1 hour. The colourless crystalline precipitate is filtered off with suction, is washed with water and is dried in a vacuum desiccator. The result is 54.5 g of N-(N,N-dimethylamino-n-propyl)-3,5-dinitrobenzamide (m/e=296 (M+)).

An analogous procedure is used to prepare the following compounds:

| Example | | | | | |
|---|---|---|---|---|---|
| 2 | 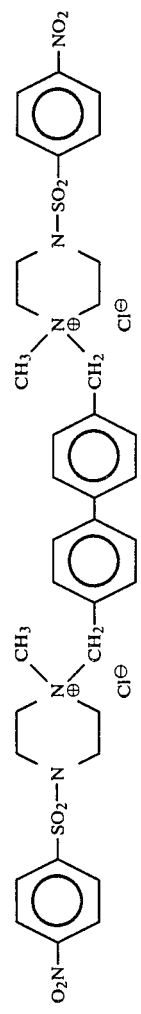 | | | | |
| 3 | | 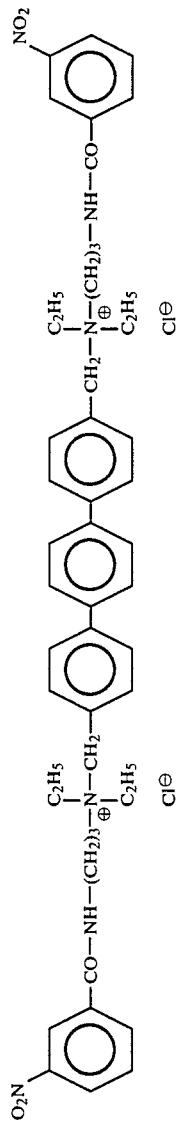 | | | |
| 4 | | | 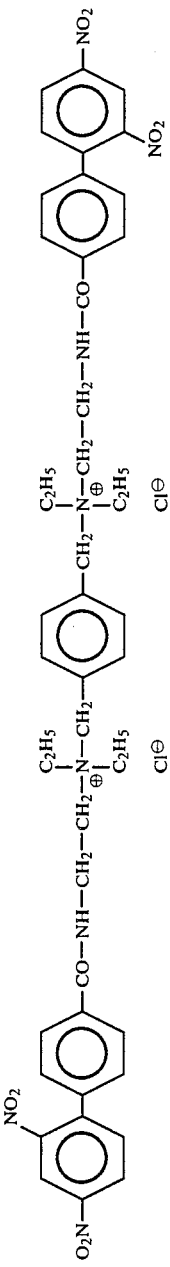 | | |
| 5 | | | | 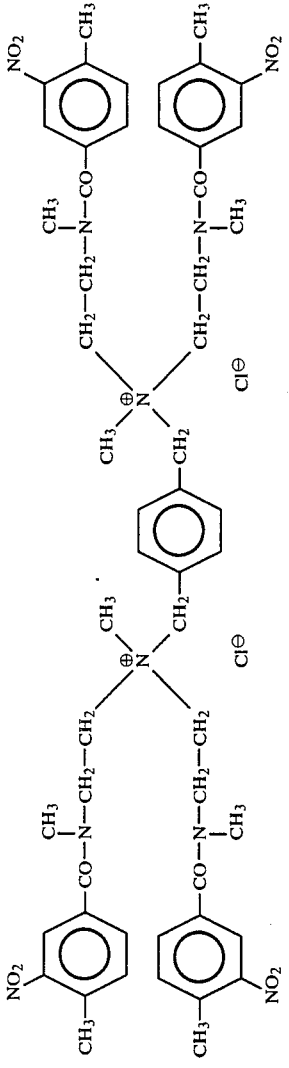 | |
| 6 | | | | | 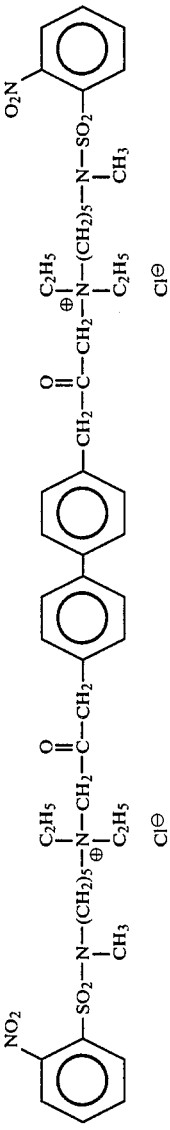 |

-continued

| Example | |
|---|---|
| 7 | (structure with piperazine rings bearing SO₂-aryl(NO₂)₂ groups, quaternary N⁺ with CH₂CH₂OH and benzyl substituents, Cl⁻ counterions) |
| 8 | (structure with two 3-methyl-4-nitrophenyl ester groups connected via azo linkage, quaternary ammonium centers with CH₃ groups, Cl⁻ counterions) |
| 9 | (structure with two 5-nitronaphthalene-1-carboxamide groups, central quaternary ammonium with CH₃ groups, Cl⁻ counterions) |
| 10 | (structure with two 2-nitro-4-nitrophenyl acetamide groups linked via (CH₂)₃, quaternary ammonium with CH₃ groups, Cl⁻ counterions) |
| 11 | (structure with thiophene core, quaternary ammonium with CH₃ groups, 4-nitrophenyl ester linkages, Cl⁻ counterions) |

-continued

| Example | |
|---|---|
| 12 | Structure containing 5-nitrothiophene-C(O)-NH-(CH₂)₃-N⁺(CH₃)₂-CH₂- linked via isoxazole (N-N, O) to -CH₂-N⁺(CH₃)₂-(CH₂)₂-NH-C(O)- 5-nitrothiophene, 2 Cl⁻ |
| 13 | Structure: 3-nitro-phthalimide-(CH₂)₃-N⁺(CH₃)₂-CH₂-(4-phenyl)-N(CH₃)-(4-phenyl)-CH₂-N⁺(CH₃)₂-(CH₂)₃-3-nitrophthalimide, 2 Cl⁻ |
| 14 | Structure: 3-nitro-4-methyl-C₆H₃-SO₂-NH-(CH₂)₃-N⁺(CH₃)₂-CH₂-(biphenyl)-CH₂-N⁺(CH₃)₂-(CH₂)₃-NH-SO₂-4-methyl-3-nitrophenyl, 2 Cl⁻ |
| 15 | Structure: 3-methoxy-4-nitro-C₆H₃-C(O)-CH₂-CH₂-N⁺(CH₃)₂-CH₂-(2-nitro-phenyl)-CH₂-N⁺(CH₃)₂-CH₂-C(O)-4-nitro-3-methoxyphenyl, 2 Cl⁻ |
| 16 | Structure: 4-nitro-C₆H₄-SO₂-CH₂-CH(CH₃)-N⁺(CH₃)₂-CH₂-(4-phenyl)-CH₂-N⁺(CH₃)₂-CH(CH₃)-CH₂-SO₂-4-nitrophenyl, 2 Cl⁻ |

-continued
| Example | | | | |
|---|---|---|---|---|
| 17 | 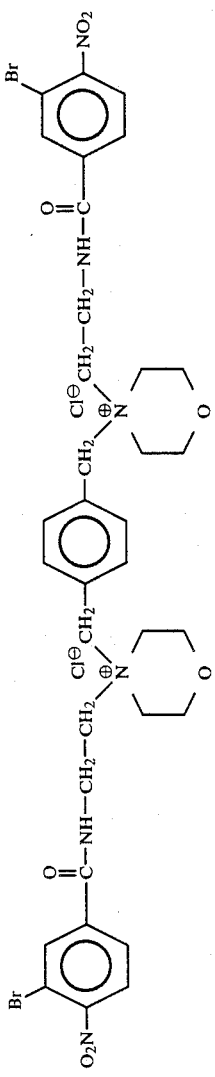 | | | |
| 18 | | 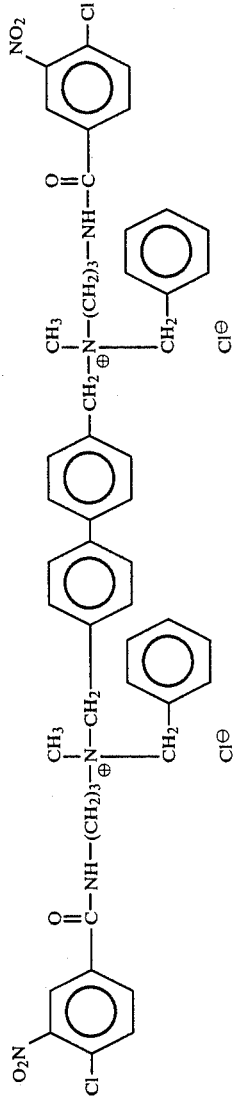 | | |
| 19 | | | 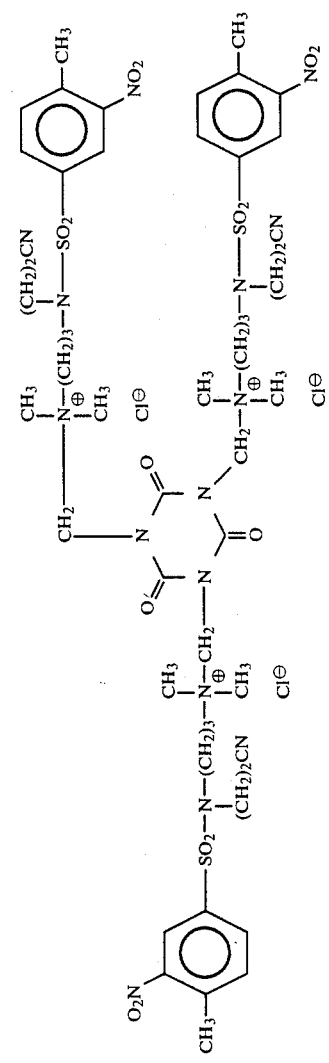 | |
| 20 | | | | 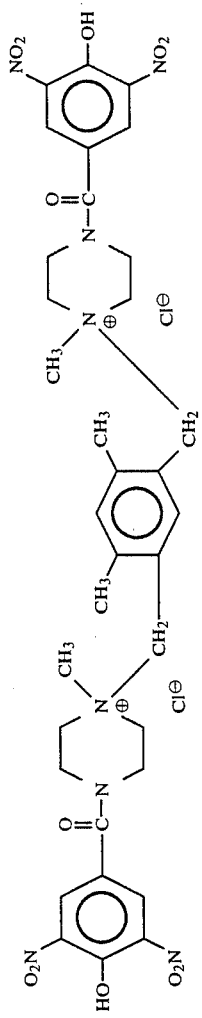 |

-continued
| Example | |
|---|---|
| 21 | 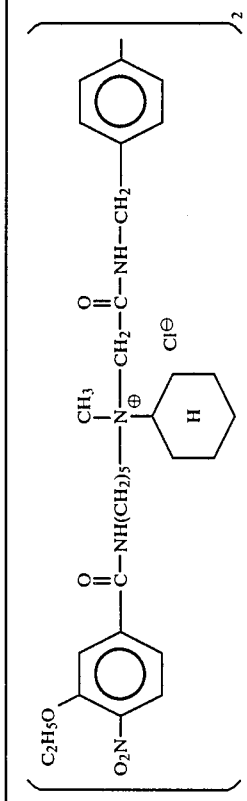 |
| 22 | 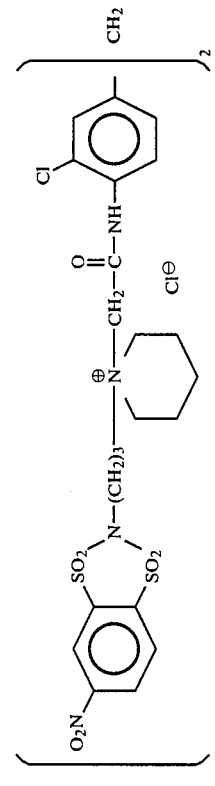 |
| 23 | 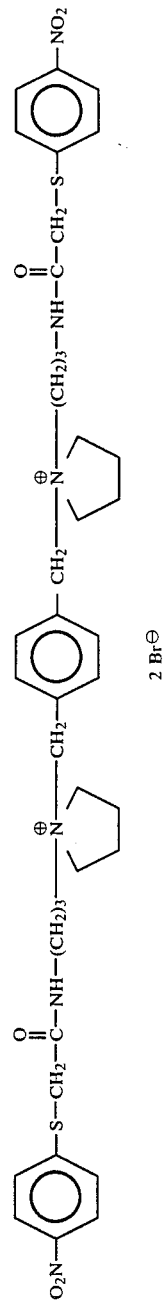 |
| 24 | 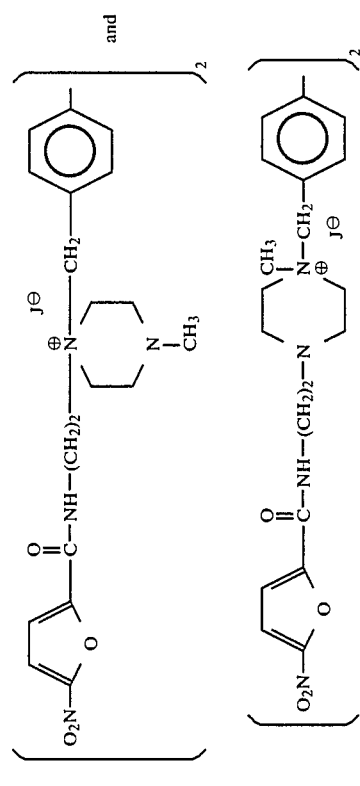 |
| 25 | |

Example 26

74.2 g of 4-nitrobenzoyl chloride are suspended in 400 ml of chlorobenzene, and 40.8 g of 3-dimethylamino-n-propylamine are added at 20°–30° C. with cooling and stirring, and the mixture is stirred at room temperature for 10 hours. Once thin layer chromatography has shown that the reaction is complete, 72 g of 30% strength sodium methylate solution are added dropwise, followed by 35 g of α,α'-dichloro-p-xylene, and the mixture is heated to 100° C. while distilling off methanol and is stirred at said temperature for 20 hours. After the mixture has cooled down, the crystalline precipitate is filtered off with suction, is washed with 500 ml of isopropanol and is dried at 40° C. in vacuo. The result is 143.5 g of colourless crystals which contain about 20 g of NaCl and otherwise consist of pure compound of the formula

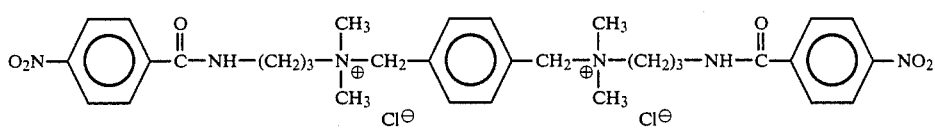

The same compound 26 can also be prepared using the method of Example 46 in DE-A-No.3,313,965.

Example 27

18.2 g of 4,4'-bis-(chloroacetamidocyclohexyl)methane and 25.6 g of N-(N,N-dimethylamino-n-propyl)-4-nitrobenzamide are heated at 90° C. for 6 hours in a mixture of 75 g of octaethylene glycol (mixture of homologues) and 7.5 g of caprolactam, and the mixture is diluted with 120 g of acetone at 20°–30° C. The colourless crystalline precipitate is filtered off with suction, is washed with acetone and is dried at 40° C. in vacuo. The result is 38.2 g of compound of the formula

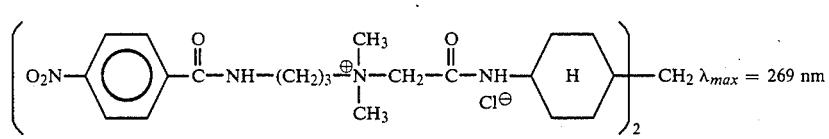

The starting 4,4'-bis-(chloroacetamidocyclohexyl)methane is prepared as follows:

105 g of 4,4'-diaminodicyclohexylmethane are dissolved in 1,000 g of anhydrous toluene, 116.5 g of chloroacetyl chloride are added dropwise at 20° to 40° C., and the mixture is refluxed for 8 hours and is cooled down. The colourless crystalline precipitate is filtered off with suction, is washed with toluene and is dried at 50° C. in vacuo. The result is 173 g of 4,4'-bis-(chloroacetamidocyclohexyl)-methane in the form of colourless crystals.

Example 28

15.4 g of α,α'-xylylene-bis-|(3-phenylacetamidopropyl)-dimethylammonium chloride| are added at 20° C. with stirring to a mixture of 20 ml of nitric acid (density 1.5) and 50 ml of concentrated sulphuric acid. The mixture is stirred at 20° to 50° C. for 4 hours, and is discharged onto 300 g of ice, and the product is salted out by adding about 200 ml of 20% strength sodium chloride solution. The crystalline precipitate is filtered off with suction and is washed with 12% strength sodium chloride solution. The result is 32 g of moist (solids content: 18 g, of which about 1.7 g are NaCl) compounds of the formula

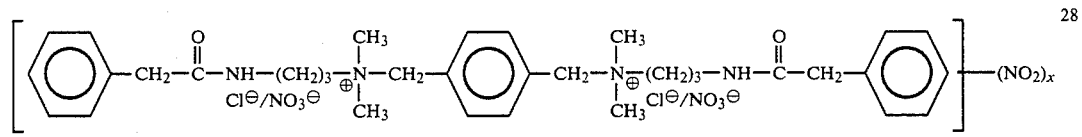

x = 3, 4, 5 and 6.

Example 29

15.1 g of N-(N,N-dimethylamino-n-propyl)-4-nitrobenzamide and 10.5 g of 4,4'-bis-(chloroacetamidophenyl)-methane are heated at 90° C. in 82 ml of water for 4 hours, and 19 g of urea are then added at 50° C. The result is an aqueous solution containing 20.2% of compound of the formula

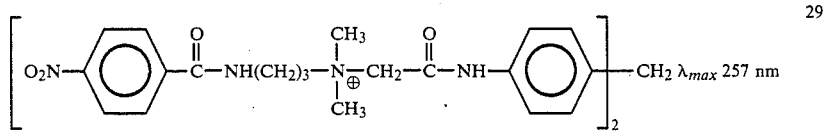

and 15% of urea. If in place of urea 12.7 g of caprolactam and a further 6.3 ml of water are used, the result is an approximately equally strong stable aqueous solution of 28, which contains about 10% of caprolactam.

If 4,4'-bis-(chloroactamidophenyl)-methane is replaced by an equivalent amount (10.8 g) of 4,4'-bis-(chloroacetamidocyclohexyl)-methane, the subsequent result, on addition of 19 g of urea, is in 82 ml of water at 90° C. (4 hours) an aqueous solution containing about 20.4% of compound of the formula 27 and about 15% of urea ($\lambda_{max}$=269 nm).

All these solutions are fully stable to storage. They are advantageously used in this form for quenching the fluorescence of anionic whiteners.

If the original method is repeated with 150 ml of boiling acetonitrile in place of water, the result is compound 29 in the form of colourless crystals in a yield of 21.5 g.

4,4'-Bis-(chloroacetamidophenyl)-methane is obtainable as follows:

79.2 g of 4,4'-diaminodiphenylmethane are suspended in 1,100 ml of chloroform, 153 g of triisopropanolamine and then dropwise at 20° to 25° C. with stirring and cooling 90.4 g of chloroacetyl chloride are added, and the mixture is stirred for 12 hours. The colourless crystalline precipitate is filtered off with suction, is washed with 400 ml of methanol and then in 7 liters of water, and is dried at 50° C. in vacuo.

Yield 128 g (91% of theory); m/e=350 (M⊕, 2Cl).

A procedure analogous to 29 is used to prepare the following compounds of the formula

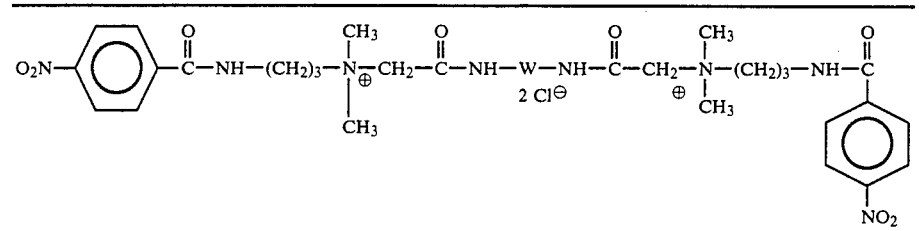

| Example | W |
|---|---|
| 30 | ![4,4'-biphenyl with two OCH3 groups] |
| 31 | ![diphenyl-C(CH3)2-] |
| 32 | ![diphenyl-CH(phenyl)-] |
| 33 | ![diphenyl ether] |
| 34 | ![diphenyl sulfide] |
| 35 | ![diphenyl sulfone SO2] |
| 36 | ![fluorenone] |

-continued
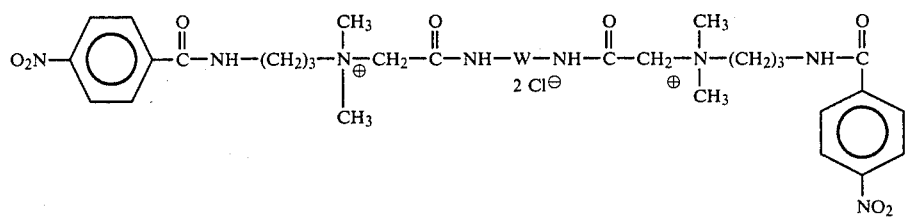
| Example | W |
|---|---|
| 37 | 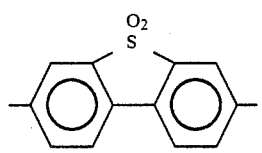 |
| 38 | 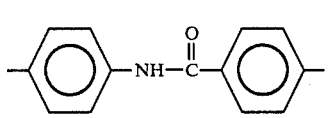 |
| 39 | 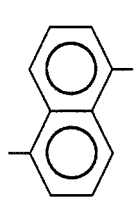 |
| 40 | 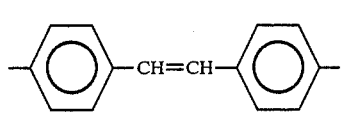 |
| 41 | 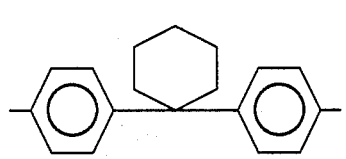 |
| 42 | 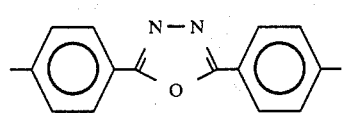 |
| 43 | 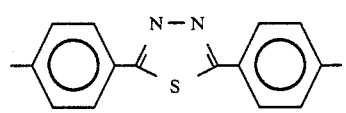 |
| 44 | 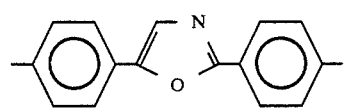 |
| 45 | 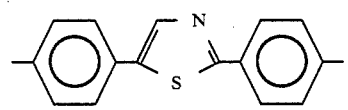 |
| 46 | 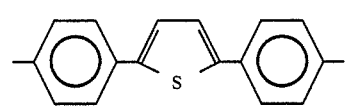 |

-continued
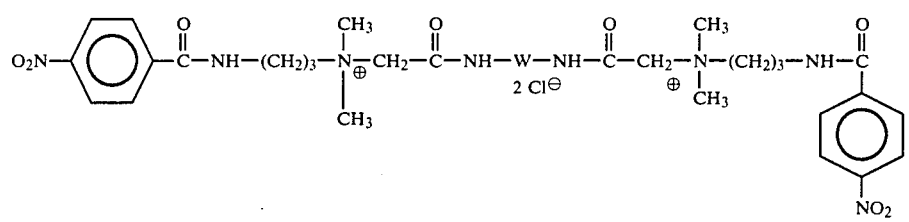
| Example | W |
|---|---|
| 47 | 3-Cl-C6H3-CH2-C6H3-3-Cl (bis(3-chlorophenyl)methane linker) |
| 48 | -C6H4-NH-C(O)-NH-C6H4- |
| 49 | -C6H4-C(O)-C6H4- |
| 50 | -C6H4-N(C6H5)-C6H4- |
| 51 | -C6H4-NH-C6H4- |
| 52 | dibenzofuran-diyl |
| 53 | -C6H10-C(CH3)2-C6H10- |
| 54 | -C6H10-NH-C(O)-NH-C6H10- |
| 55 | -C6H10-CO-NH-C6H10- |
| 56 | -C6H10-O-C6H10- |

-continued
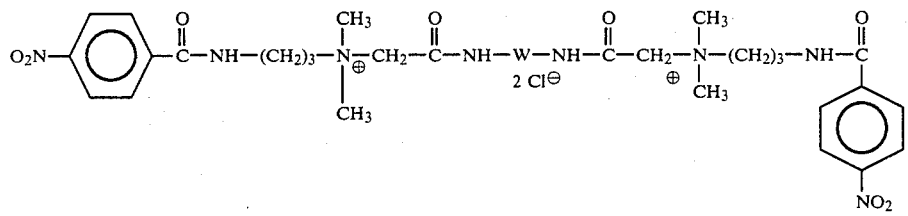
| Example | W |
|---------|---|
| 57 | 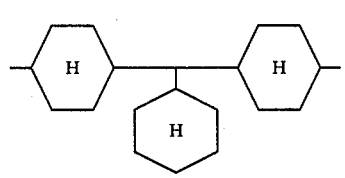 |
| 58 | 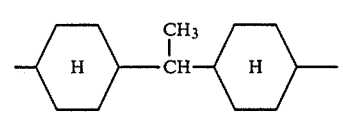 |
| 59 | 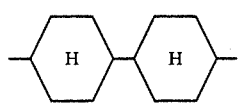 |
| 60 | 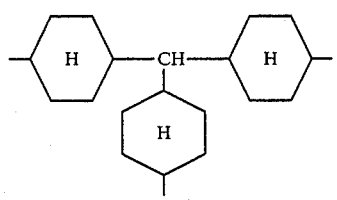 |
| 61 | 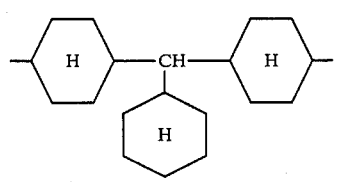 |
| 62 | 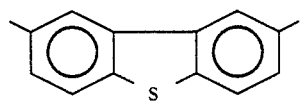 |
| 63 | 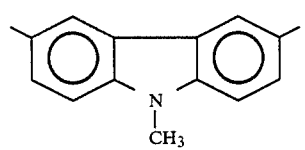 |
| 64 | 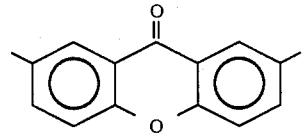 |

-continued
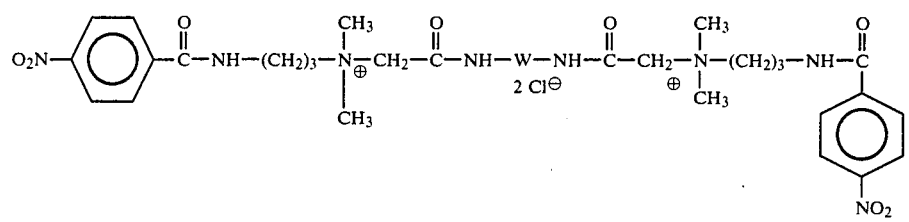
| Example | W |
|---|---|
| 65 | (3,6-dimethyl-10-methylacridin-9(10H)-one-diyl) |
| 66 | -C6H4-CH2-CH2-C6H4- |
| 67 | -C6H4-C(CH3)2-CH2-C(CH3)2-C6H4- |
| 68 | -C6H4-O-CH2-CH2-O-C6H4- |
| 69 | -C6H4-CH2-CH2-O-CH2-CH2-C6H4- |
| 70 | -C6H4-S(=O)-C6H4- |
| 71 | -C6H4-C6H4-C6H4- (terphenyl) |
| 72 | -C6H10-C(=O)-C6H10- |
| 73 | (5-yl-2-aryl-2H-benzotriazole) |
| 74 | -C6H4-CH2-C6H4- with -SO2- bridge |

-continued
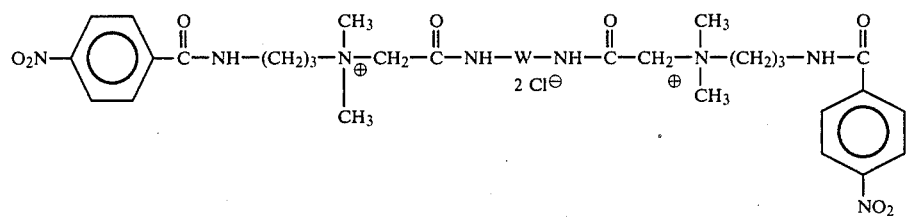
| Example | W |
|---|---|
| 75 | 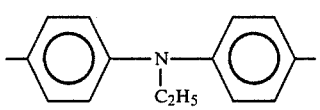 |
| 76 | 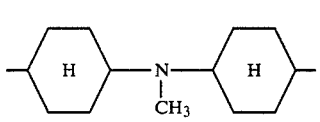 |
| 77 | 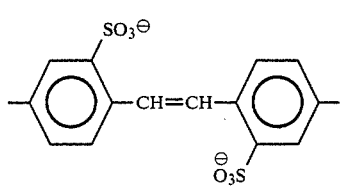 |
| 78 | 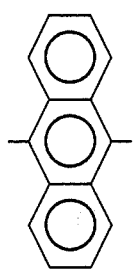 |
| 79 | 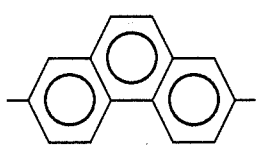 |
| 80 | 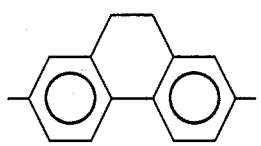 |
| 81 | 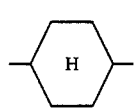 |
| 82 | 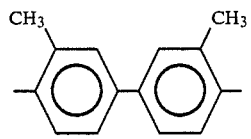 |

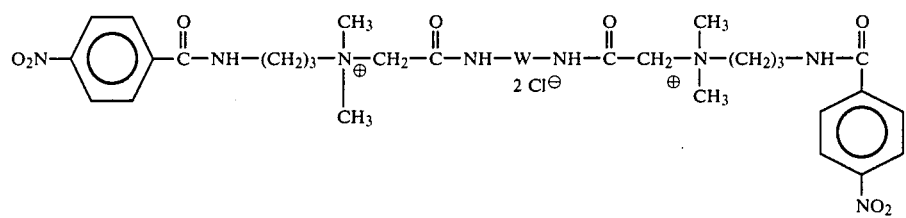
| Example | W |
|---|---|
| 83 | 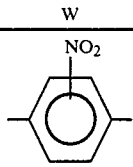 |
| 84 | 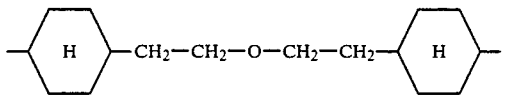 |
| 85 | 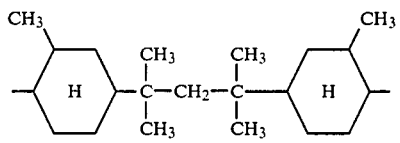 |
| 86 | 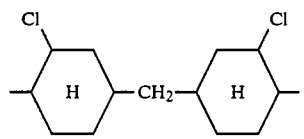 |
An analogous procedure is likewise used to prepare the following compounds of similar activity: Example
| Example | |
|---|---|
| 87 | 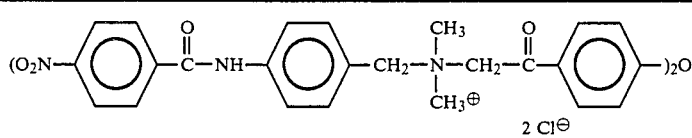 |
| 88 | 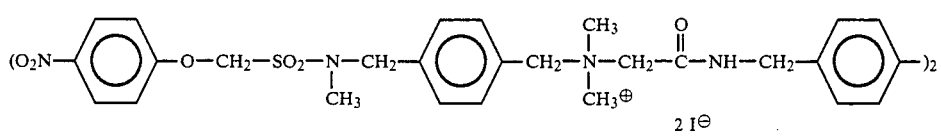 |
| 89 | 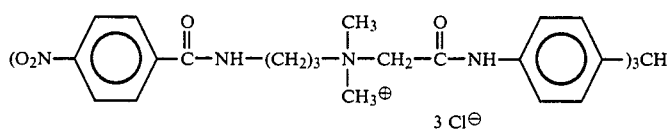 |
| 90 | 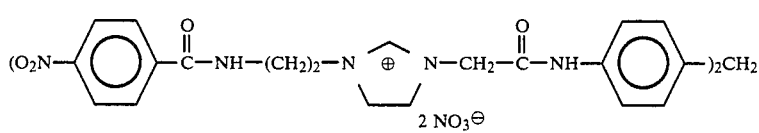 |

| Example | |
|---|---|
| 91 | 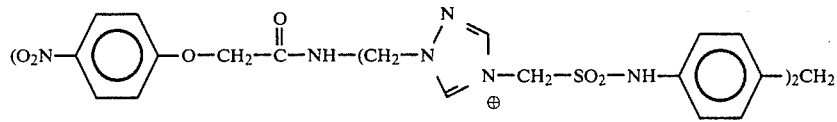 |
| 92 | 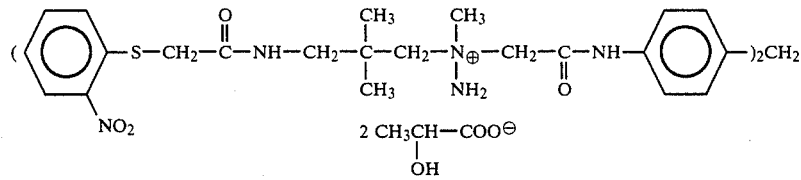 |
| 93 | 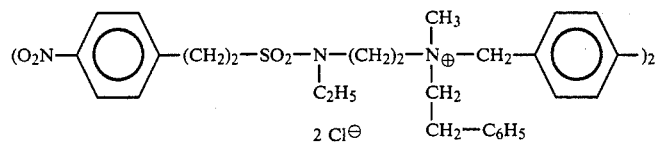 |
| 94 | 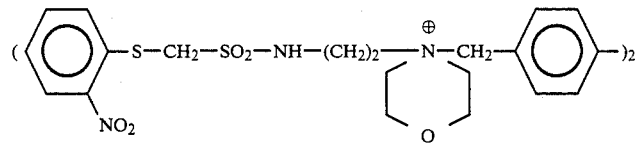 |
| 95 | 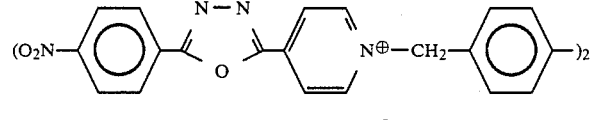 |
| 96 | 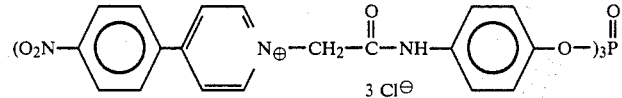 |
| 97 | 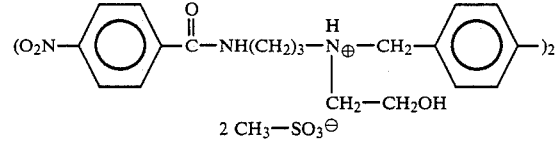 |
| 98 | 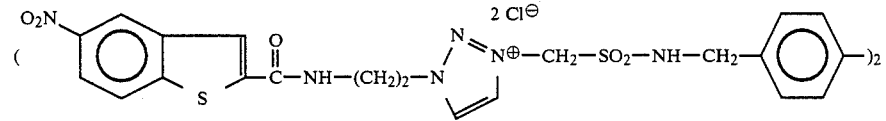 |
| 99 | 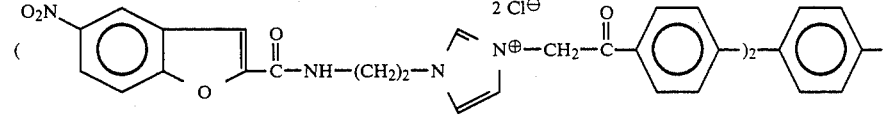 |

-continued

| Example | |
|---|---|
| 100 | 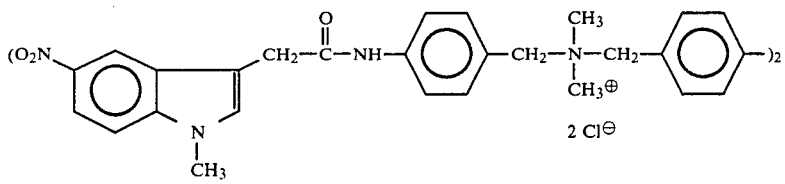 2 Cl⊖ |
| 101 | 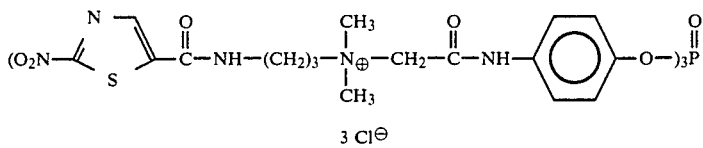 3 Cl⊖ |
| 102 | 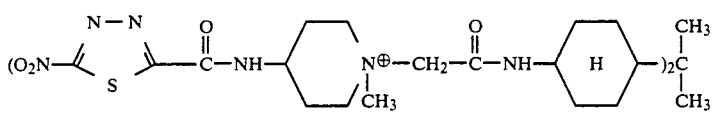 |
| 103 | 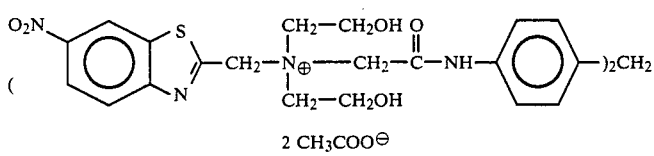 2 CH₃COO⊖ |

Example 104

50 g of 3-nitrophenacyl bromide and 40 g of bis-(isonicotinoylamidophenyl)-methane are heated at 100° C. in 250 ml of dimethylformamide for 30 hours, and cooled down. The colourless crystalline precipitate is filtered off with suction, is washed with isopropanol and is dried at 40° C. in vacuo. The result in 85 g of compound of the formula

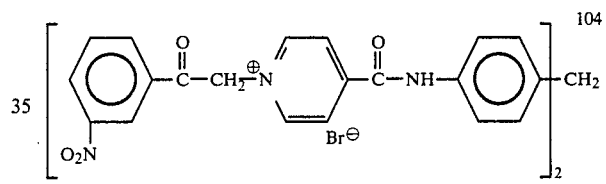

A 10% strength solution of 104 in lactic acid is completely miscible with water.

Bis-(isonicotinoylamidophenyl)-methane is accessible analogously to 4,4'-bis-(chloroacetamidophenyl)-methane (Example 29) from 4,4'-diaminodiphenylmethane and 2 equivalents of isonicotinoyl chloride.

3-Nitrophenacyl bromide can be prepaed from 3-nitroacetophenone and bromine analogously to Org. Synth., Coll. Vol. II, 420–481.

A procedure analogous to that for preparing compound 104 is used to prepare the following compounds of similar activity:

| Example | |
|---|---|
| 105 | 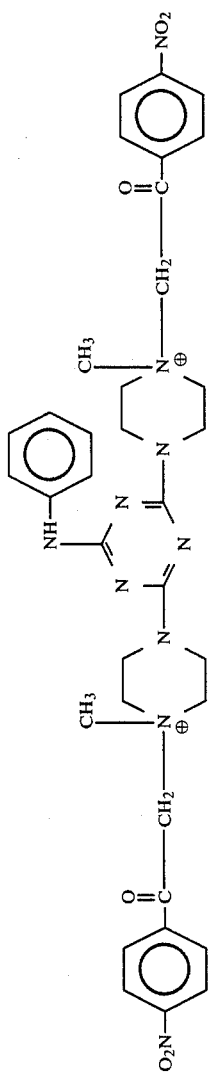 |
| 106 | 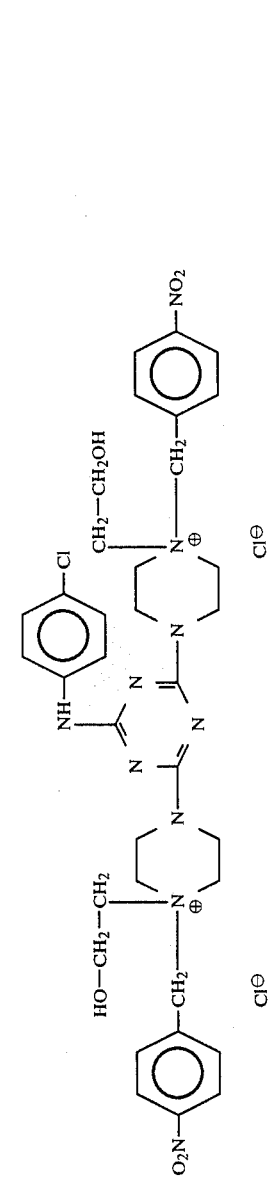 |
| 107 | 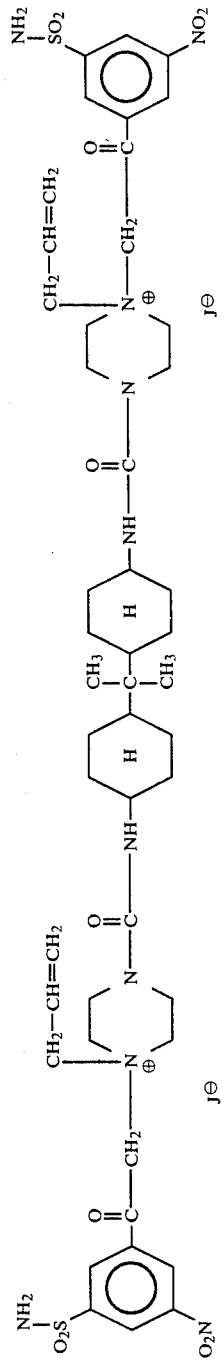 |
| 108 | 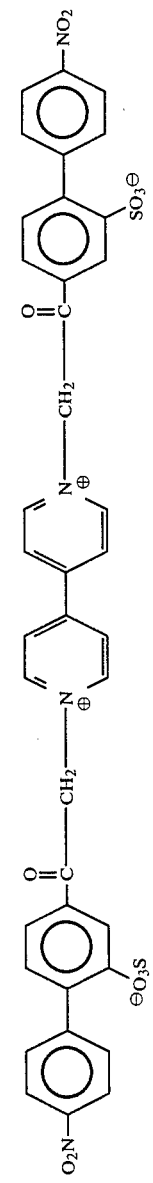 |

-continued
| Example | |
|---|---|
| 109 | 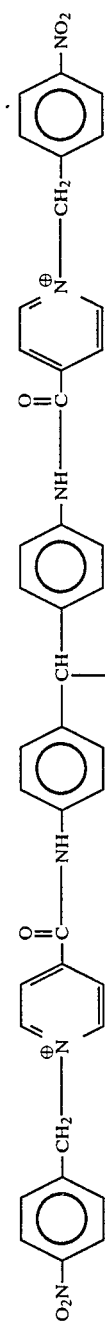 |
| 110 | 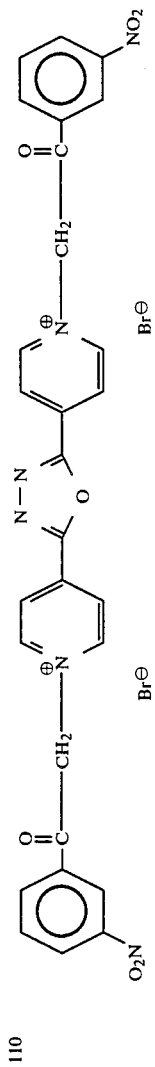 |
| 111 | 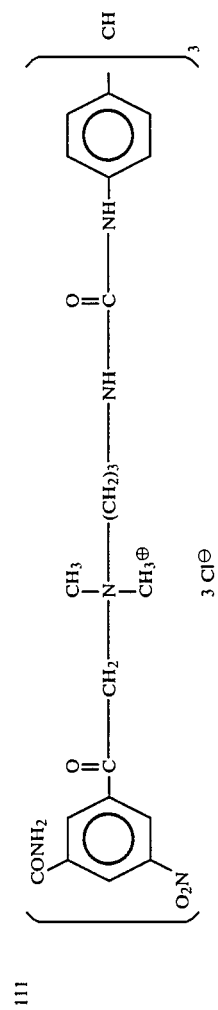 |
| 112 | 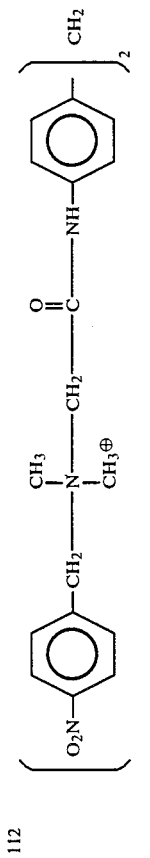 |
| 113 | 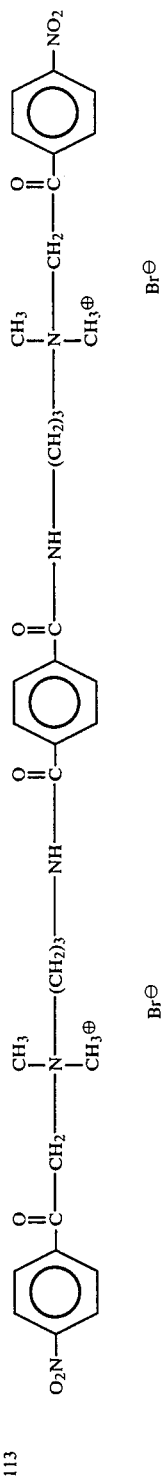 |

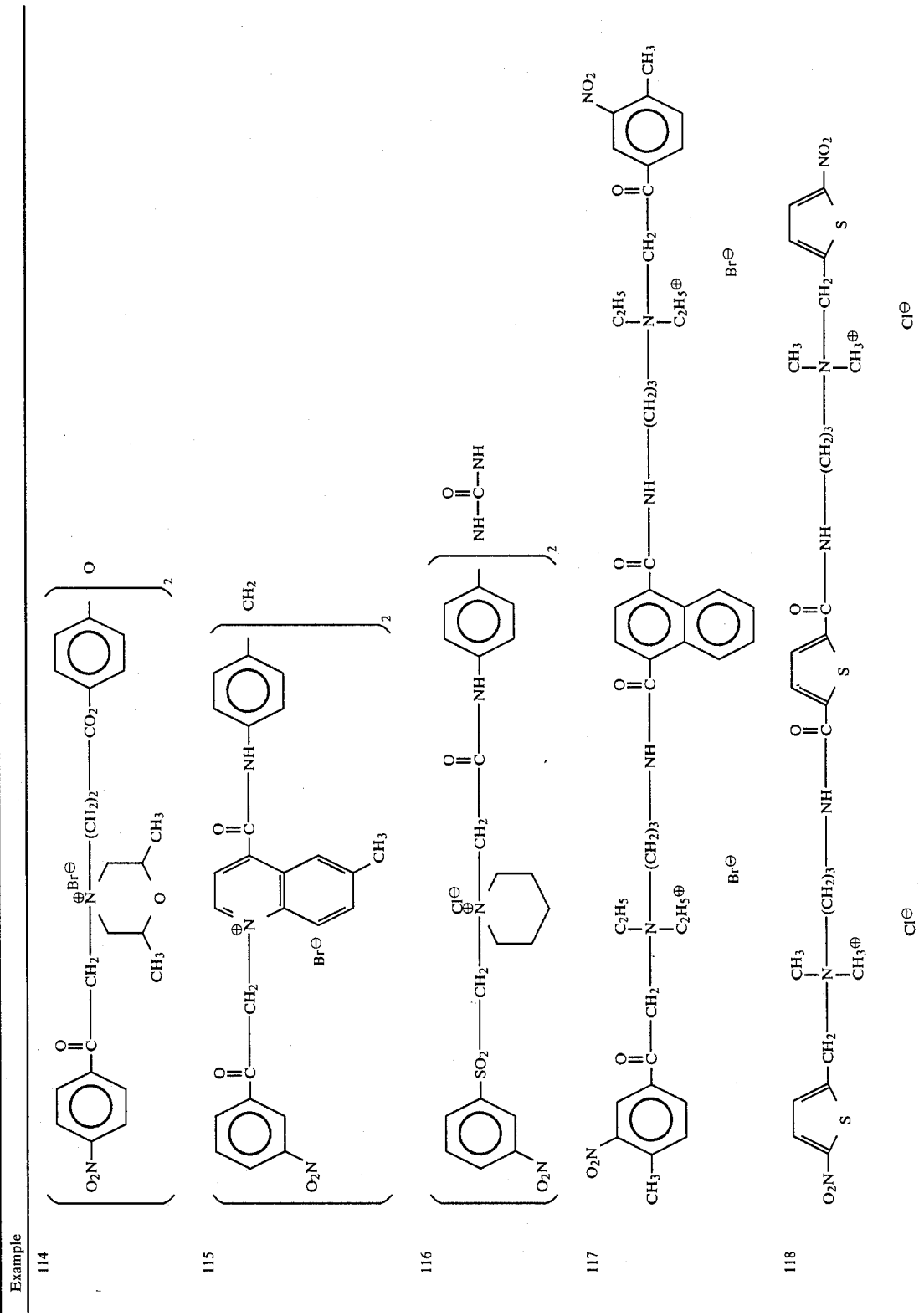

| Example | |
|---|---|
| 119 | 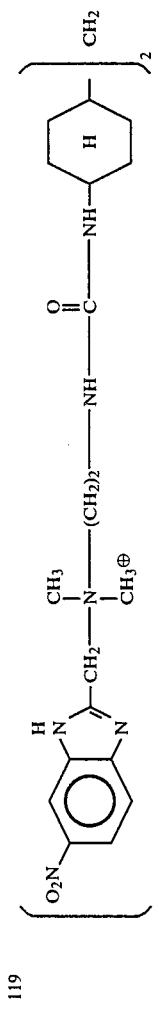 |
| 120 | 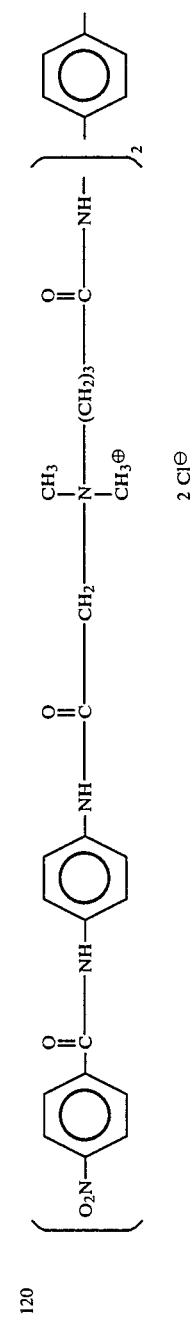 |
| 121 | 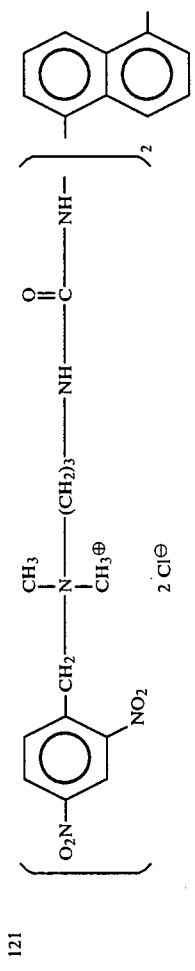 |
| 122 | 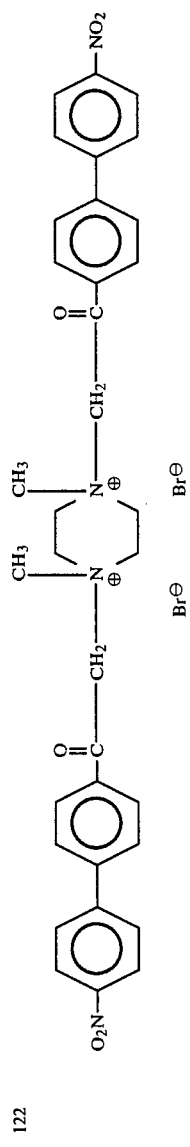 |

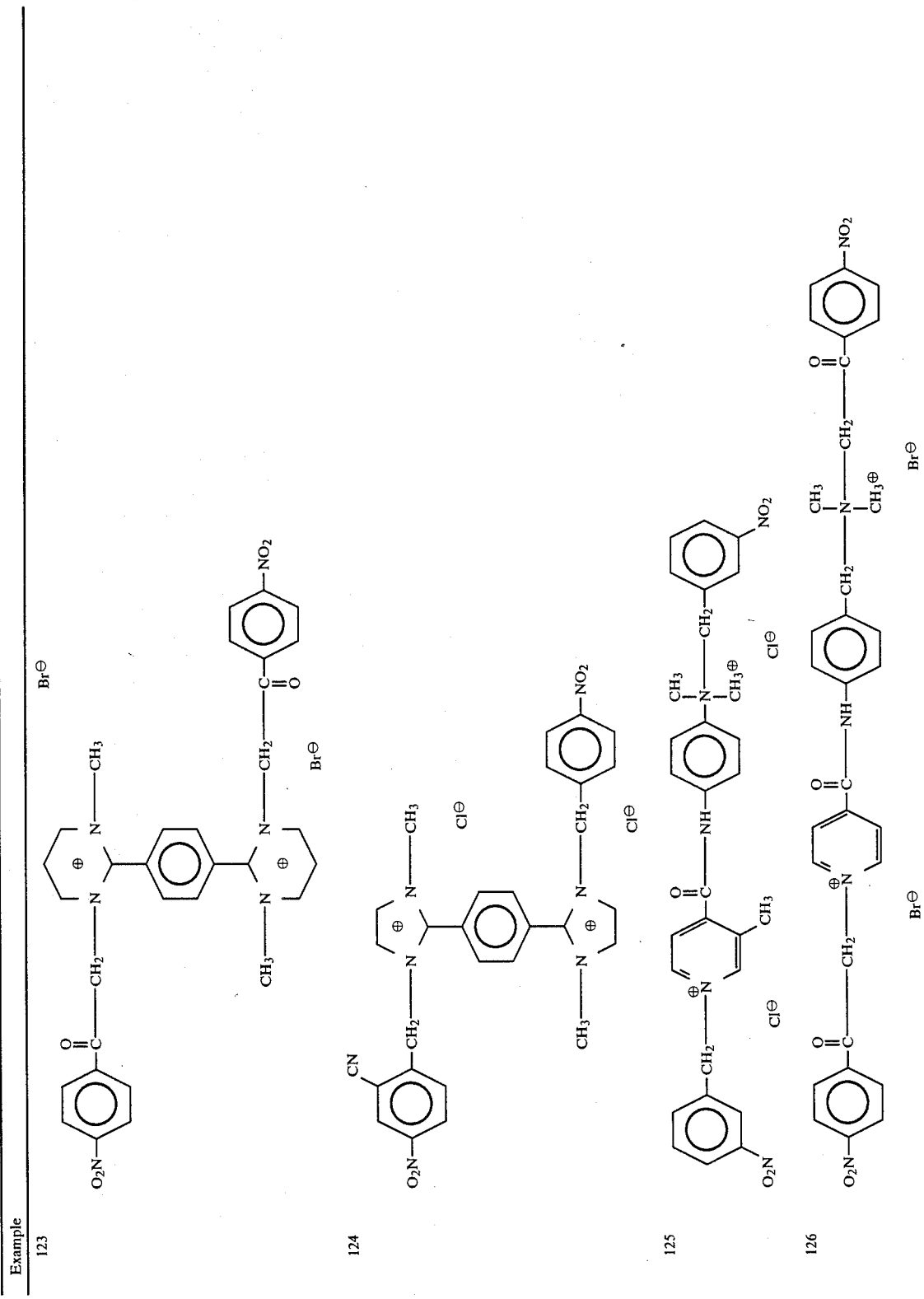

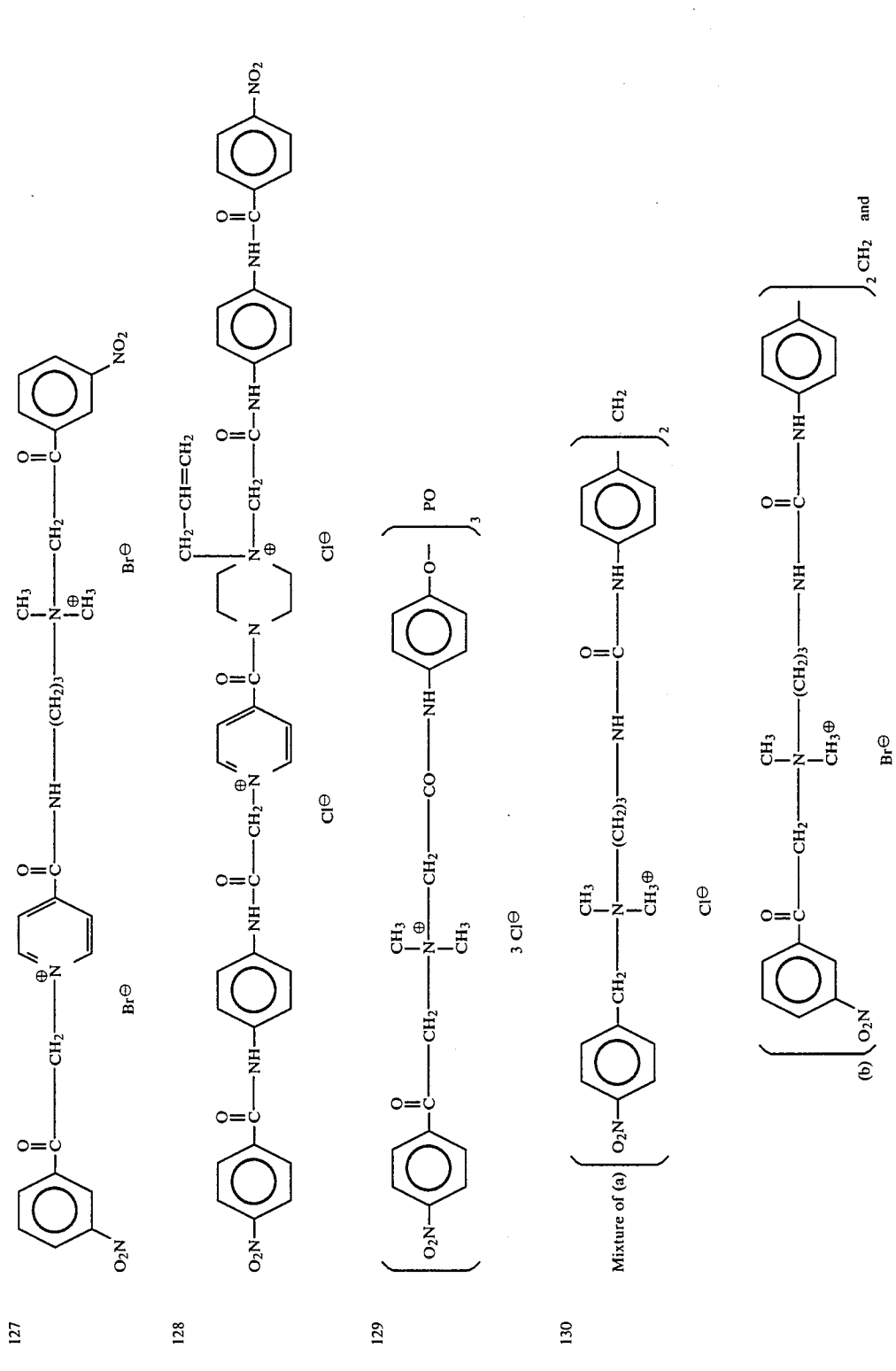

-continued
| Example | |
|---------|---|
| 131 | 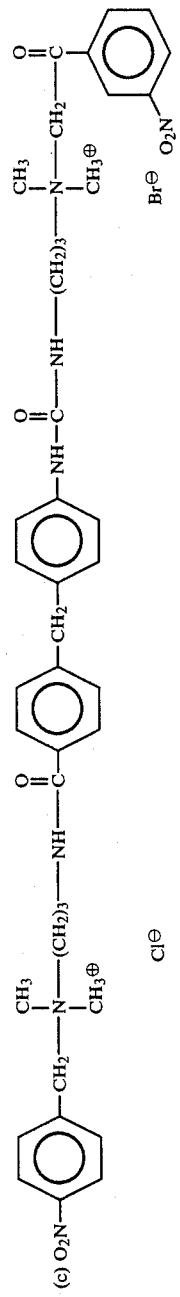 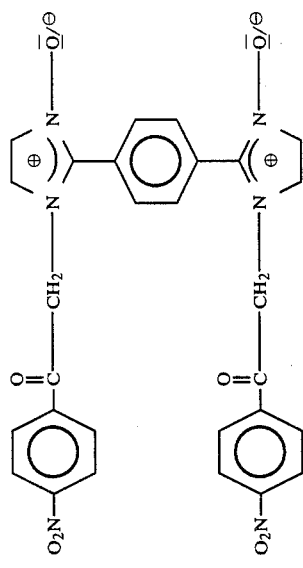 |
| 132 | 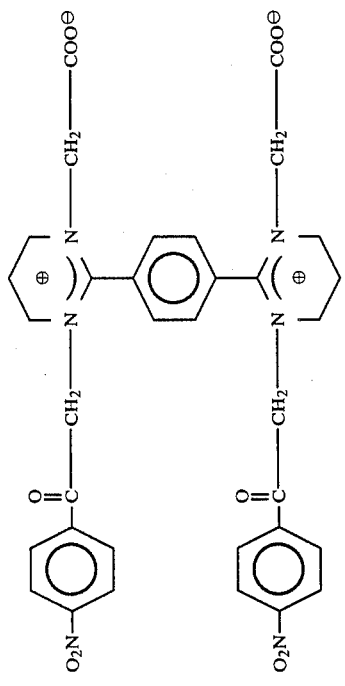 |

| Example | |
|---|---|
| 133 | 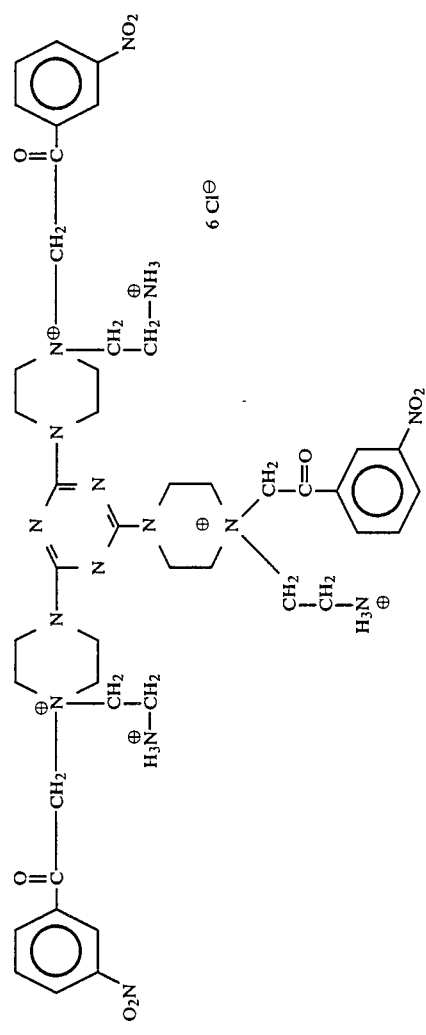 |

Example 134

166 g of isophthalic acid and 103 g of diethylenetriamine are used in line with Example D of No. DE-A-1,912,647 to prepare in water and triethylene glycol 1 mole of 50% strength polyimidazoline compound of the formula

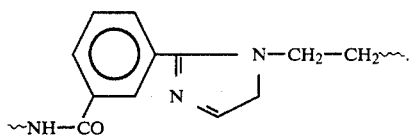

43.5 g thereof (0.1 equivalent, relative to the structural unit) are heated at 110° C. with 16 g of 4-nitrobenzyl chloride for 16 hours. On cooling down the mixture is diluted with 3.5 ml of water. The result is a pale brown, viscous solution which contains the compound

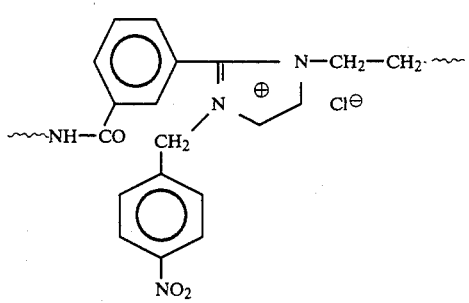

in triethylene glycol/water.

A fluorescence quencher for anionic fluorescent brighteners which is as strong as 134 is obtained when 4-nitrobenzyl chloride is replaced by an equivalent amount of 3-nitrophenacyl chloride.

g of triethylene glycol are added after 2 hours, and the condensation is continued at 190° to 200° C./40 to 50 mm Hg. After 20 hours the vacuum is nullified by means of nitrogen, and the reaction mixture is gradually diluted at 130° C. with 100 g of dry triethylene glycol. After cooling down the result is a brown viscous solution which contains a crude polyimidazoline derivative of the formula

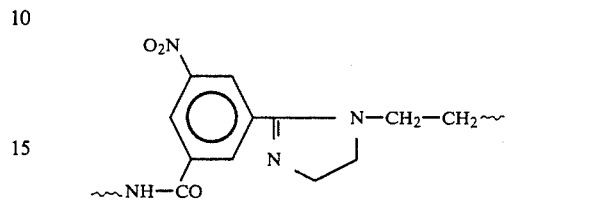

A tenth of the resulting solution is heated to 110° C. together with 8.5 g of chloroacetamide for 3 hours and is then diluted with 10 ml of water. After cooling down the result is a pale brown viscous solution which contains the compound

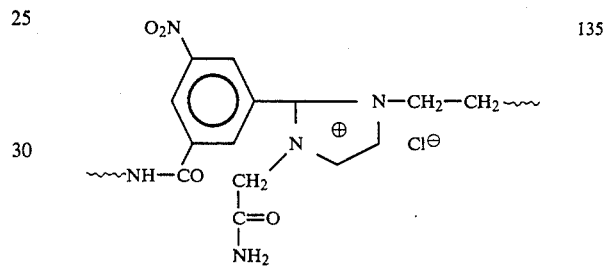

in triethylene glycol/water.

Example 136

9.3 g of 4-nitrobenzoyl chloride and 31 g of compound of the formula

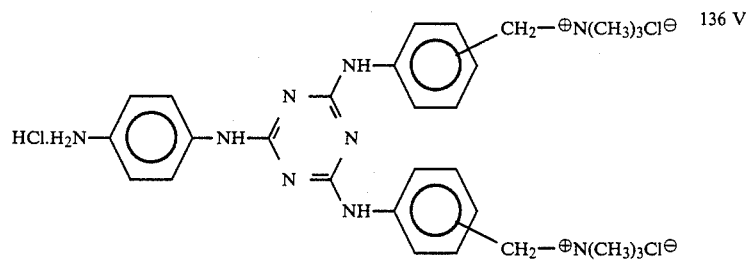

Example 135

227 g of 5-nitroisophthalic acid are added at 20° to 90° C. with stirring in analogy to Examples D and F of No. DE-A-1,912,647 to 103 g of diethylenetriamine and 150 ml of water, the result being an exothermic reaction. Under nitrogen the mixture is heated at 190° C. for 3 hours, water being distilled off via a column. The condensation is continued at 190° to 200° C./30 mm Hg, 120 are stirred at 20° to 25° C. initially with cooling in 200 ml of dimethylformamide in the presence of 19.1 g of triisopropanolamine for 20 hours, and the mixture is evaporated to dryness at a waterbath temperature of 40° C. in vacuo in a rotary evaporator. The residue is stirred with 200 ml of ethanol for 2 hours, is filtered off with suction and is washed with ethanol. The result is 35 g of compound of the formula

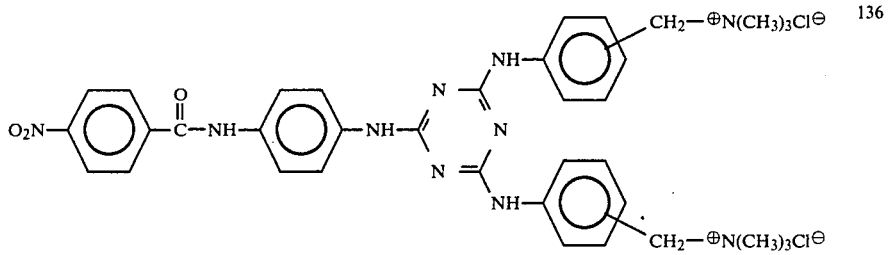

136

The intermediate product 136 V can be prepared as follows:

43.5 g of 4-aminoacetanilide are suspended in a mixture of
120 ml of water and
100 g of ice, and the suspension is subsequently brought to pH 5.5 by adding 1.7 ml of 10% strength hydrochloric acid.

This solution is combined with a cold suspension at 0° to 5° C., homogenised with a stirrer at about 10,000 revolutions, comprising 53.6 g of cyanuric chloride, 120 ml of water, 48 g of ice and 1.2 g of a polyether of lauryl alcohol and 5 moles of ethylene oxide.

The suspension thus obtained is stirred at 5° C. for 3 hours during which the pH is maintained at 4 by the dropwise addition of about 96 ml of 10% strength sodium hydroxide solution.

A solution of 166 g of a mixture of ⅔ of 4- and ⅓ of 3-aminobenzyltrimethylammonium methosulphate, brought to pH 5 with 30 g of sodium carbonate, is then added, followed by 160 ml of water, and the mixture is heated to 95° C., is brought to pH 8 with about 120 g of sodium carbonate and is stirred at 95° C. and pH 8 for 3 hours.

The mixture is then stirred under reflux with 180 ml of concentrated hydrochloric acid for 2 hours and is filtered to remove slight turbidity, the filtrate is much reduced to a rotary evaporator, the residue is extracted with 1 liter of methanol, and the extract is evaporated in dryness.

Yield: 153 g of 136 V.

The starting aminobenzyltrimethylammonium methosulphate was prepared as follows:

47.5 ml of dimethyl sulphate are added dropwise at 20° to 25° C. to 75 g of a mixture of ⅔ of 4- and ⅓ of 3-aminobenzyldimethylamine in 200 ml of acetone, colourless crystals being precipitated. The mixture is stirred at room temperature for 3 hours. The crystalline precipitate is filtered off with suction, is stirred with 250 ml of isopropanol, is filtered off with suction, is washed with 100 ml of isopropanol and is dried at 50° C. in vacuo. Yield 129 g.

A procedure analogous to that for preparing compound 136 is used to prepare the following compounds:

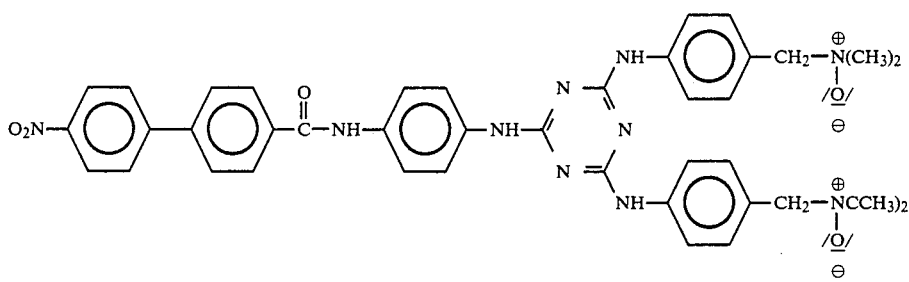

137

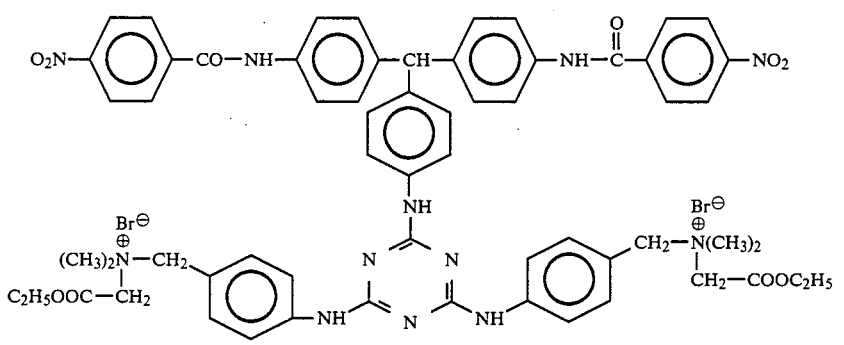

138

-continued
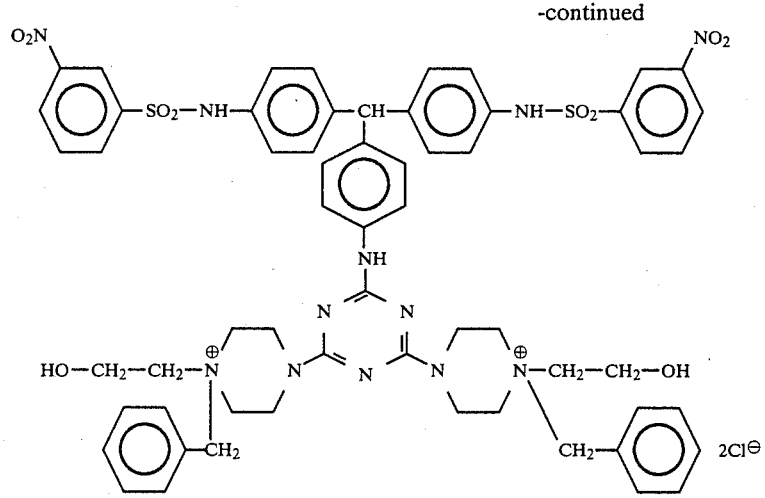
139
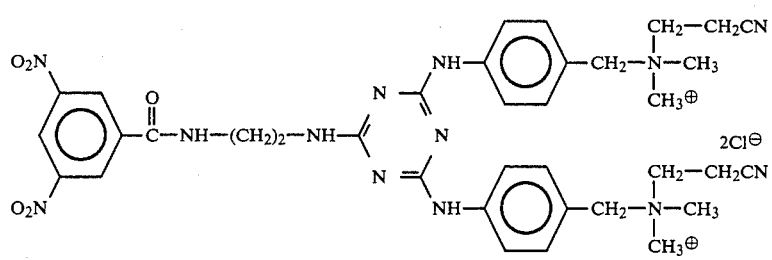
140
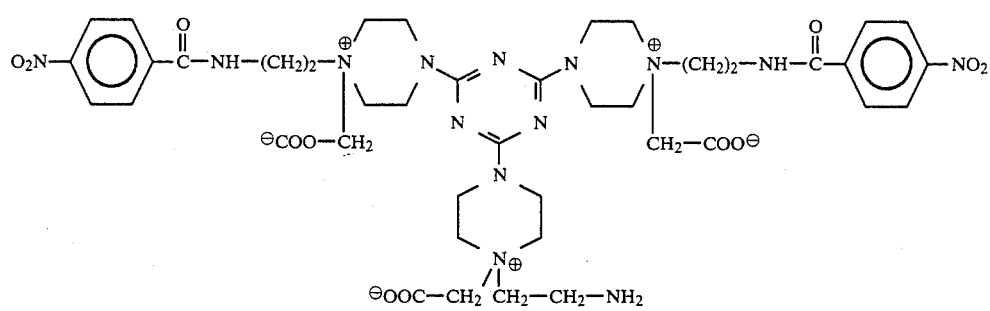
141
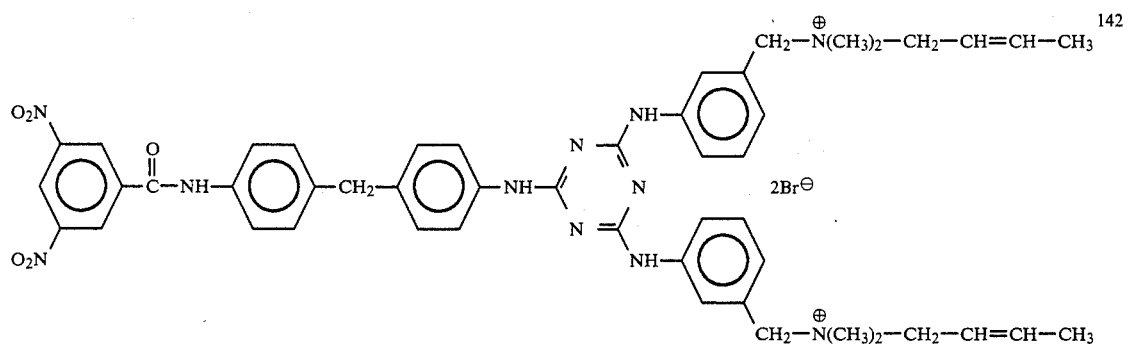
142
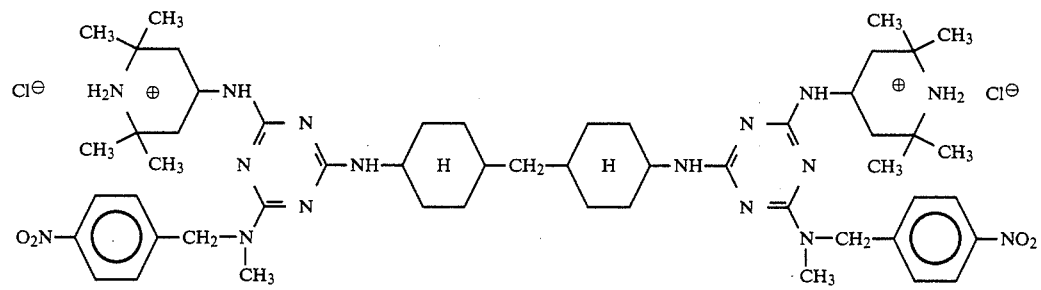
143

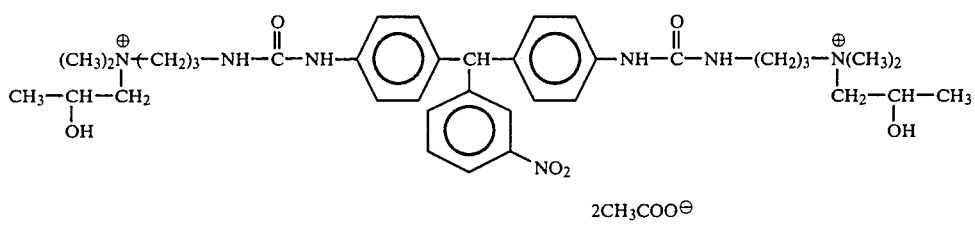

144

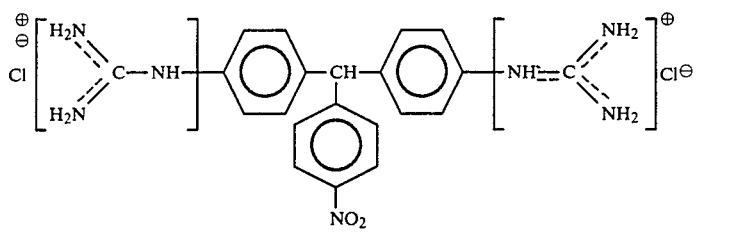

145

The compounds are likewise highly active fluorescence quenchers.

Example 146

A solution of 30 g of styrene and 6 g of benzoyl peroxide in 100 g of ethyl acetate is added dropwise at 80° C. in accordance with the method of German Auslegeschriften Nos. 1,495,850 and 1,469,727 to a solution of 70 g of maleic anhydride in 70 g of ethyl acetate in the course of 12 hours; afterwards the solvent is evaporated off in vacuo. The resulting copolymer, which has a molecular weight of about 2,000, is suspended in 100 g of toluene. 75 g of 3-dimethylaminopropylamine are added dropwise at 25°–75° C. to the suspension in the course of 2 hours, and the mixture is stirred for a further 15 hours. The crystalline precipitate is filtered off with suction, is washed with toluene, and is dried. The polymeric compound thus prepared contains structural units of the formula

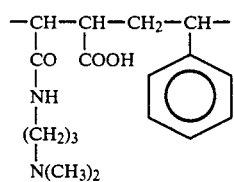

146 V 0.1 equivalent thereof (relative to the structural unit) and 16 g of 4-nitrobenzyl chloride are heated at 120° C. in 100 ml of triethylene glycol for 15 hours, the mixture is cooled down, and 10 ml of water are added. The result is a pale brown viscous solution which contains a polymeric compound having structural units of the formula

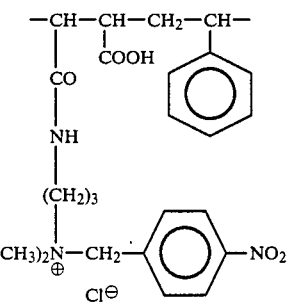

146

The compound has a strong fluorescence-quenching action under the conditions of Use Example B.

An equally strong fluorescence quencher is obtained when 4-nitrobenzyl chloride is replaced by an equivalent amount of 3-nitrophenacyl chloride.

An analogous procedure is used to prepare polymeric fluorescence quenchers which contain the following structural units:

```
    —CH—CH—CH2—CH—                                  147
        |        |      |
        CO    COOH   
        |                        
        NH                      
        |
       (CH2)2
        |
       N(CH3)3       NO2
        ⊕           CH3SO4⊖
```

```
    —CH—CH—                                          148
        |      |
        CO  COOH
        |
        NH
        |
       (CH2)3
        |
  (CH3)2N—CH2—CO—⟨  ⟩
        ⊕
        Br⊖
                        NO2
```

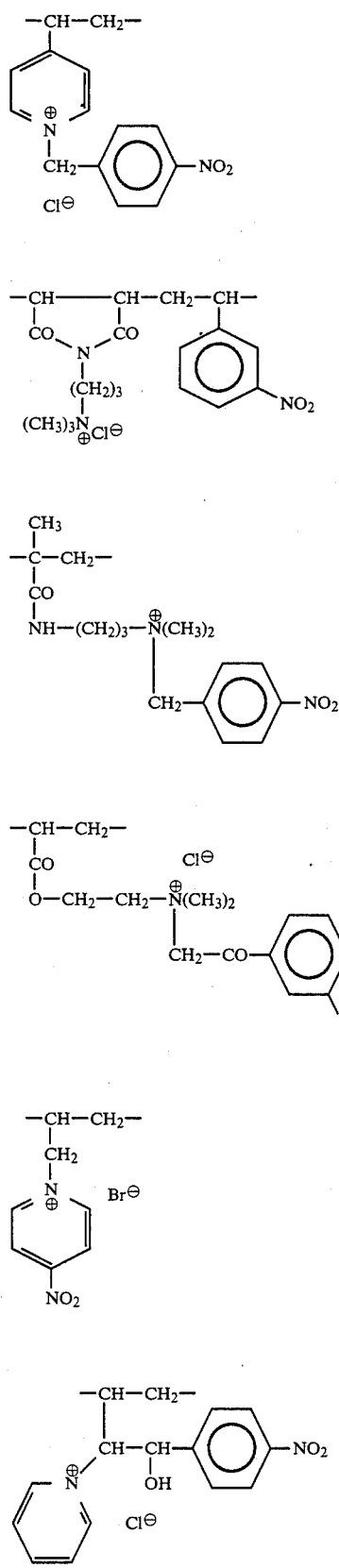
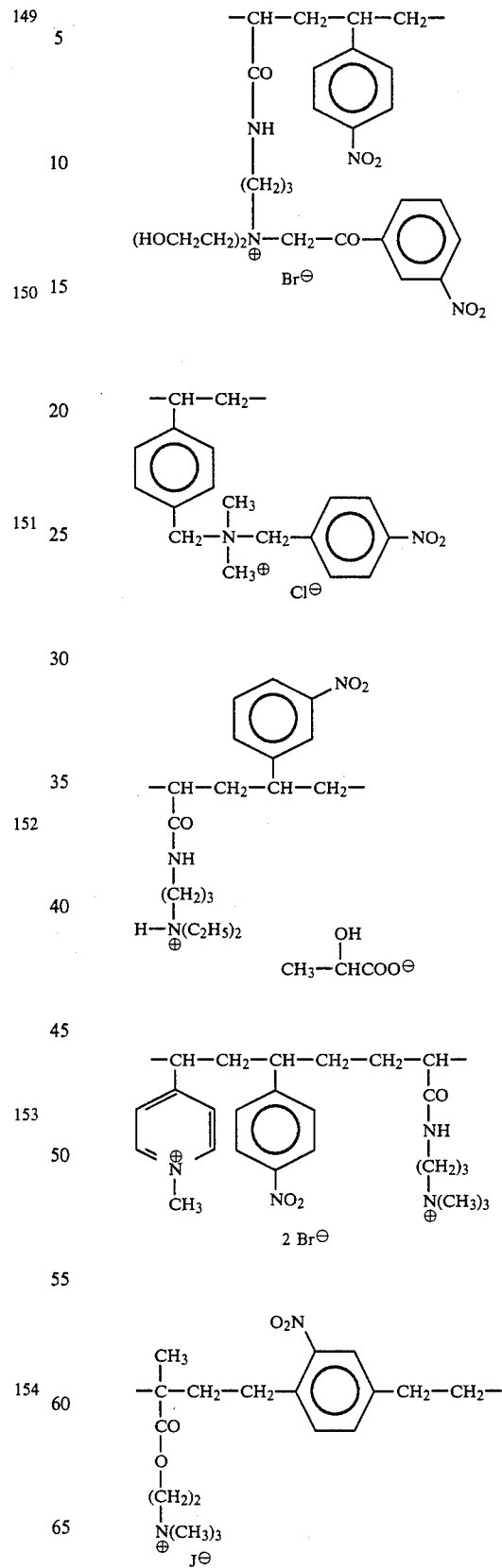

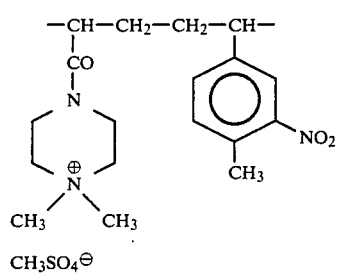
160
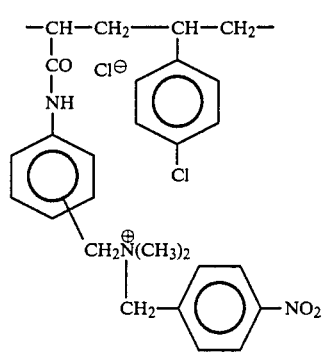
161
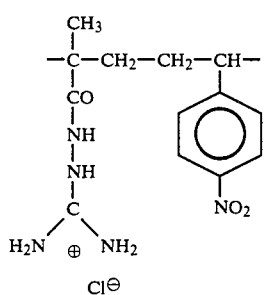
162
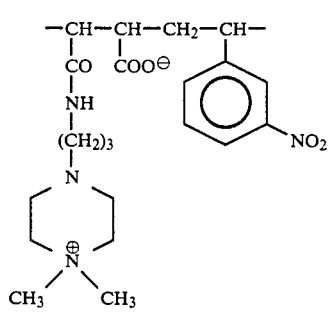
163
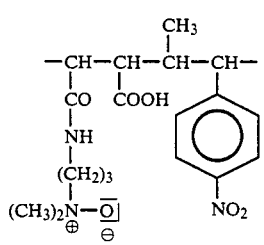
164
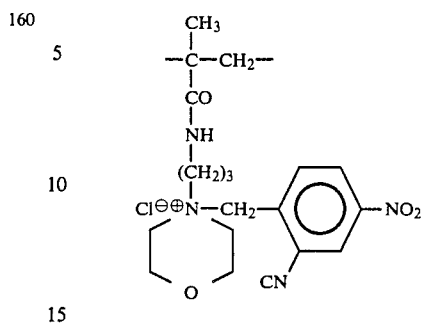
165
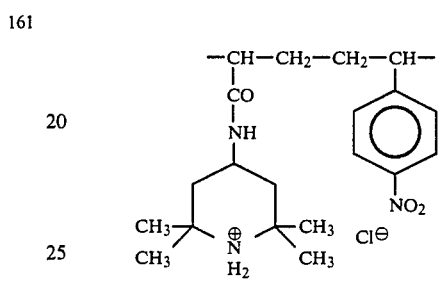
166
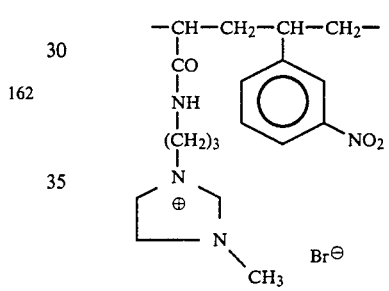
167
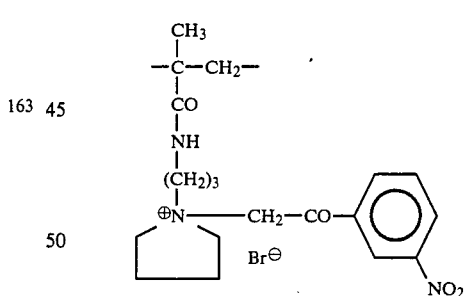
168
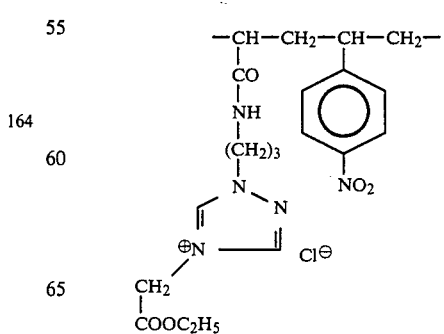
169

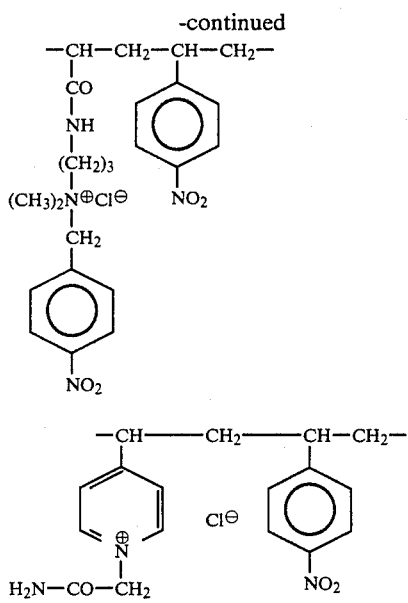

170

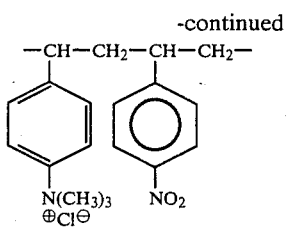

172

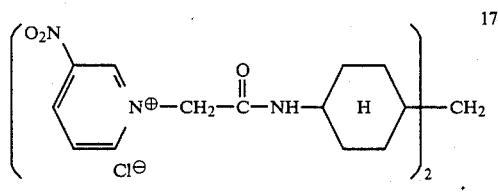

171

EXAMPLE 173

35 g of 4,4-bis-(chloroacetamidophenyl)-methane and 27 g of 4-nitropyridine are heated at 120° C. in 150 ml of dimethylformamide under nitrogen for 4 hours. When the mixture has cooled down the crystalline precipitate is filtered off with suction, is washed with isopropanol and is dried in vacuo. The result is 52 g of compound of the formula

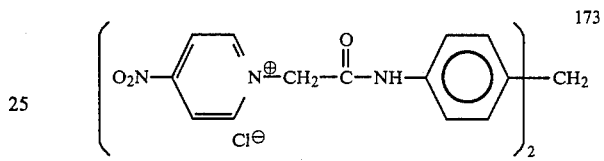

173

173 shows a strong fluorescence-quenching action under the conditions of Use Example B. An analogous procedure is used to prepare the following, equally strongly fluorescence-quenching compounds:

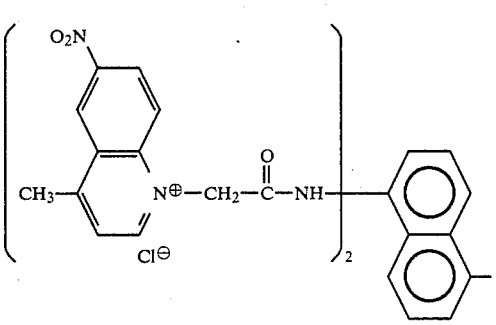

174

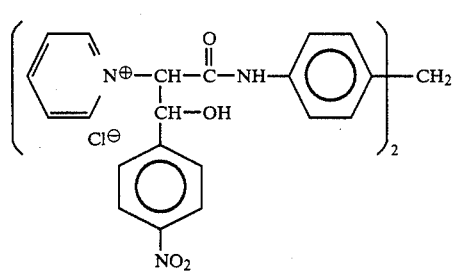

175

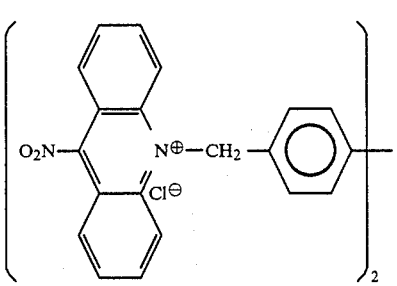

176

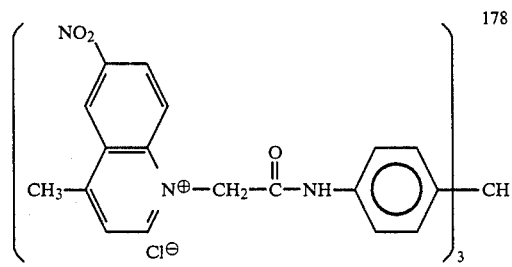

177

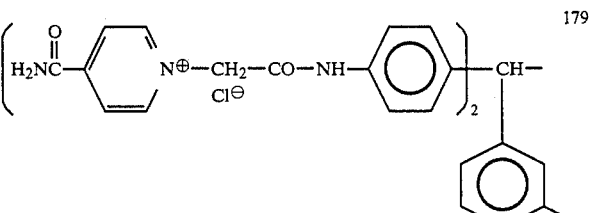

178

179

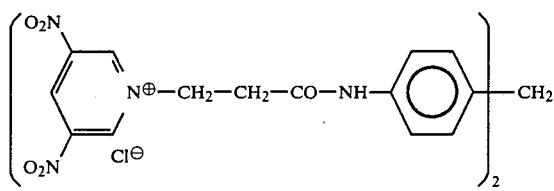 180
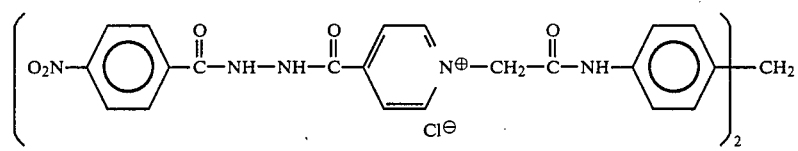 181
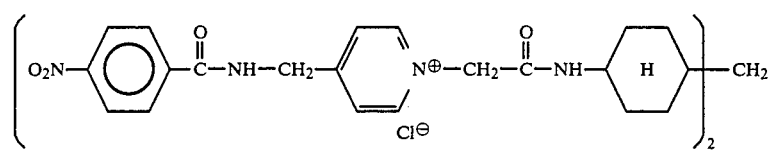 182
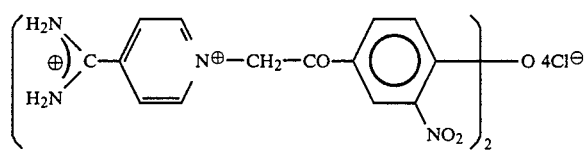 183
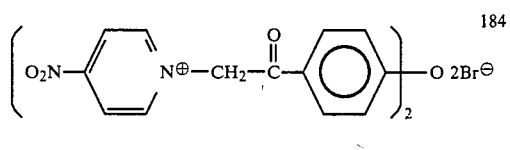 184
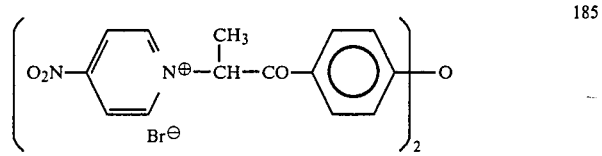 185
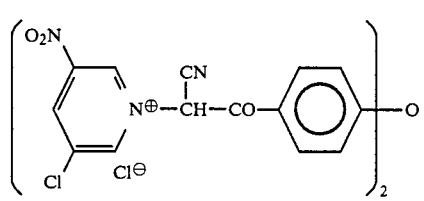 186
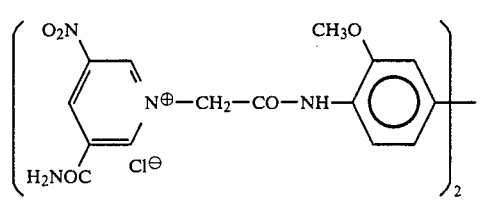 187
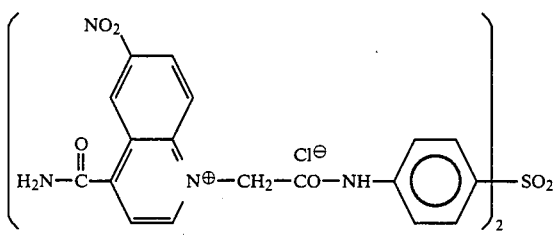 188
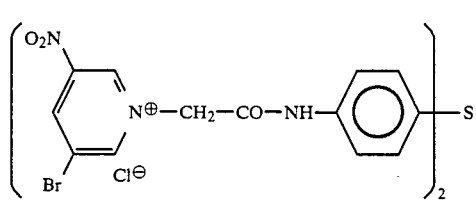 189
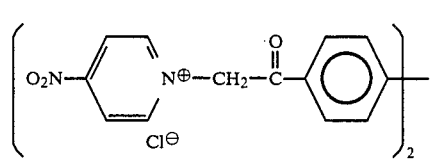 190

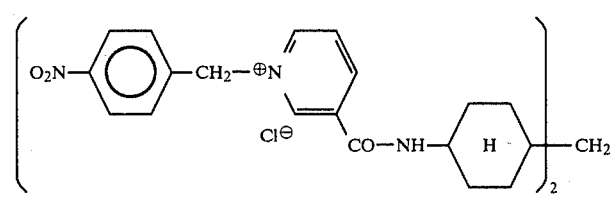
191
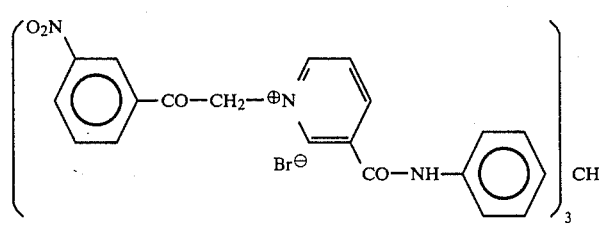
192
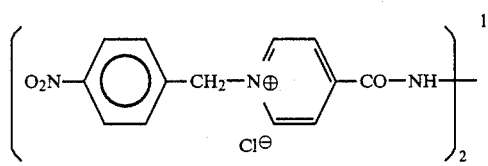
193
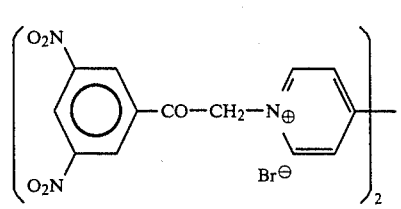
194
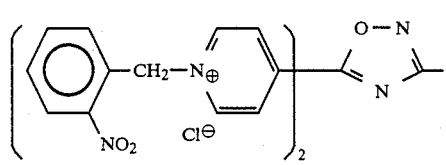
195
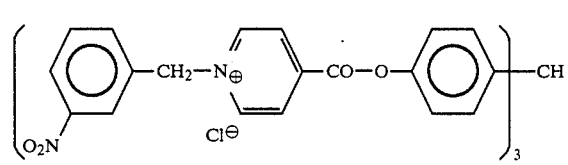
196
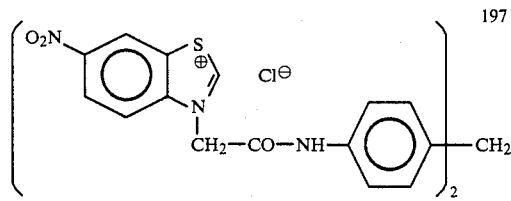
197
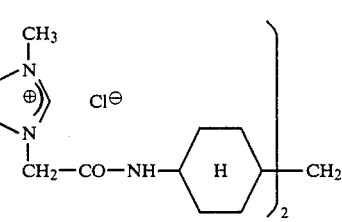
198
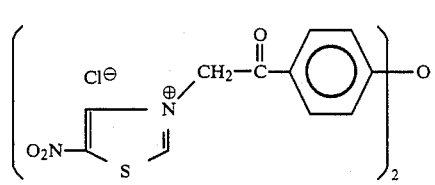
199
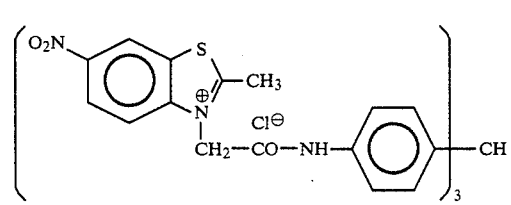
200
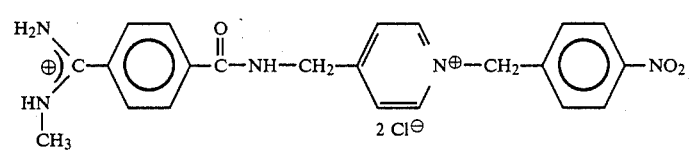
201
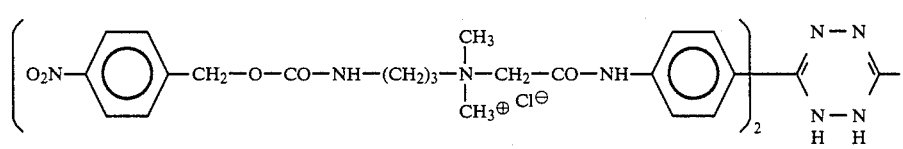
202
(Preparation analogous to Exmple 27)

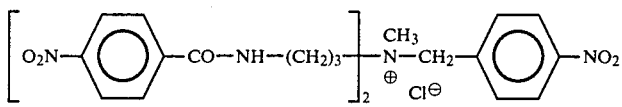

203

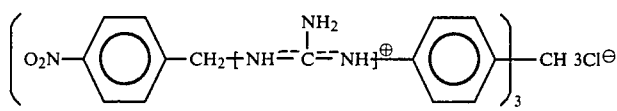

204

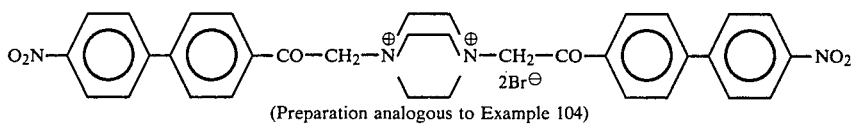

205

(Preparation analogous to Example 104)

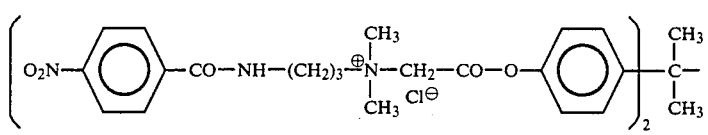

206

(Preparation analogous to Example 27)

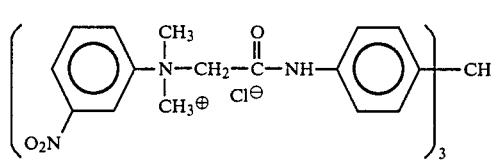

207

(Preparation analogous to Example 27)

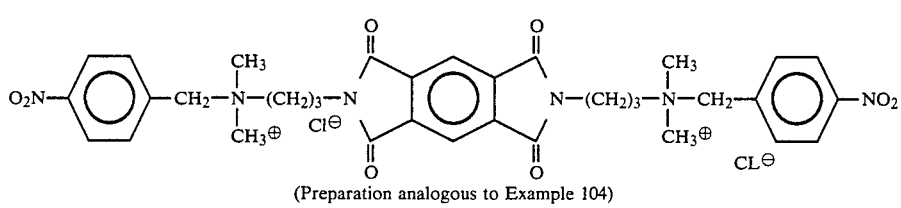

208

(Preparation analogous to Example 104)

Use Example A 5,000 parts of bleached sulphite cellulose pulp having a Schopper-Riegler freeness of 40° and a solids content of 2% (corresponding to 100 parts of sulphite cellulose) are brought with stirring to pH 7.5 with sodium hydroxide solution, a solution of 0.2 part of the fluorescent brightener of the formula

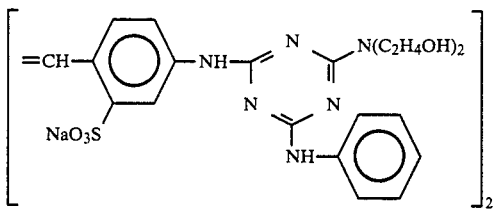

in 100 parts of water is added, and the mixture is stirred for 5 minutes. 100 parts of an aqueous solution which contains 0.4 part of the fluorescence quencher described in Preparation Example 27 are added, the mixture is stirred for 1 minute, and a sheet of paper is formed. On drying, the result is paper which is virtually no different from non-brightened paper.

If, on the other hand, the same amount is used of a fluorescence quencher prepared according to Example A or B of No. DE-A-1,912,647 or according to Preparation Example 1 of No. DE-A-2,448,293, the paper obtained has a distinctly noticeable white effect.

On repeating the comparative experiments at pH 9, the difference is still greater.

Use Example B 5,000 parts of bleached sulphite cellulose pulp having a Schopper-Riegler freeness of 40° and a solids content of 2% are stirred with 3 parts of crystallised aluminium sulphate for a few minutes, and a solution of 0.1 part of the fluorescent brightener of the formula

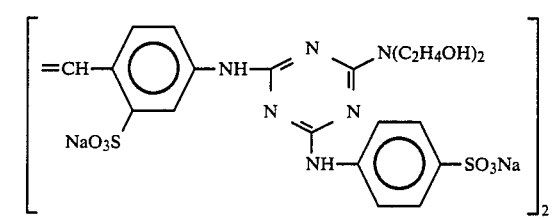

in 100 parts of water is added. 15 minutes later, 2 parts of rosin milk was added. The mixture is thoroughly stirred and then brought to pH 4.5 with sulphuric acid.

100 parts of an aqueous solution which contains 0.7 part of the fluorescence quencher described in Example 89 are then added, and the mixture is stirred for 1 minute, is diluted with water to 20,000 parts, and is used to form a sheet of paper. On drying, the result is sized paper which is virtually no different from non-brightened paper.

Equally powerful fluorescence-quenching effects are obtained when one of the fluorescence quenchers described in the other preparation examples is used.

Use Example C

From brightened waste paper as the raw material, paper having a weight of 80 g/m² is produced on a paper machine.

To quench the fluorescence of the fluorescent brighteners contained therein, the paper web is sprayed in the second half of the wet end with a dilute aqueous solution of the compounds described in Preparation Example 129 in such a way that the dry paper contains 0.02 to 0.1% (depending on the concentration of the brightener in the raw material) of fluorescence quencher.

The paper thus manufactured corresponds in the visual properties to a grade of paper which contains no fluorescent brighteners.

On using the fluorescence quenchers described in the remaining preparation examples the same success is obtained.

Use Example D 10 g of bleached nettle cotton fabric are treated at 50° C. in a liquor ratio of 20:1 with a solution of 0.1% of BLANKOPHOR ® BA 267% for 30 minutes. After rinsing and drying, the Berger whiteness is measured as 150 (basic white about 80).

The fabric thus whitened is then treated at 50° C. in a liquor ratio of 20:1 with 0.1% of the fluorescence quencher described in Preparation Example 112 for 30 minutes. After rinsing and drying, the Berger whiteness is again determined and found to be within the range from 100 to 110. Visually only a very small white effect is still perceivable.

Other compounds described in Preparation Examples 1 to 133 can also be used equally successfully.

Use Example E

The possibility of rendering inactive the unwanted residues of aqueous solutions of anionic whiteners in dyeing apparatus, dyeing machines, stock reservoir vessels and supply lines by using fluorescence quenchers of Examples 1 to 145 may be illustrated using the following quantitative model experiment:

(a) 0.03 mmol of a fluorescent brightener of the formula

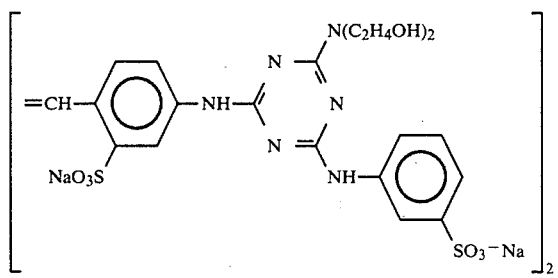

(42.2 mg of 86.5% pure = 36.5 mg of 100% pure) is dissolved in 100 ml of water.

(b) 0.1 mmol of fluorescence quencher of the formula 29 (85.4 mg) is dissolved in 100 ml of water.

(c) 5 ml of the solution prepared in (a) are made up to 100 ml. (d) 5 ml of the solution prepared in (a) and X ml of the solution prepared in (b) are mixed and made up to 100 ml (x=1, 2, 3, 4).

In a Zeiss DMR 21 spectrophotometer with a 1 ml quartz cuvette and a ZF M4 fluorescence attachment (450 W xenon lamp), using fluorescence excitation with UV light at 345 nm, the intensity of the fluorescence emissions of the following solutions at 436 nm is measured:

Solution (c) ($1.5 \times 10^{-5}$ mol/l of brightener) 100% fluorescence intensity Solution (d), x=1 ($10^{-5}$ mol/l of 29) 59% fluorescence intensity Solution (d), x=2 ($2.0 \times 10^{-5}$ mol/l of 29) 27% fluorescence intensity Solution (d), x=3 ($3.0 \times 10^{-5}$ mol/l of 29) 3% fluorescence intensity Solution (d), x=4 ($4.0 \times 10^{-5}$ mol/l of 29) 0% fluorescence intensity The experiment shows that, at room temperature in dilute aqueous solution, fluorescence quencher 29 renders the abovementioned fluorescent brightener inactive to a substantial degree at as low a molar ratio as 2:1 and completely at a molar ratio of 2.7:1.

If compound 29 is replaced by one of the compounds described in No. DE-A-1,912,647 or 2,448,293, complete fluorescence quenching is never obtained, not even if the quencher is used in higher concentrations.

If compound 29 is replaced by the fluorescence quencher of the formula 89, complete fluorescence quenching is obtained at a molar ratio as low as 4:3 (quencher/fluorescent brightener).

We claim:

1. A process for quenching the fluoresence produced by anionic fluorescent brighteners in a substrate by adding to said substrate one or more virtually colorless, water-soluble cationic or amphoteric compounds wherein the compounds have the formula

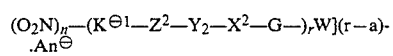

wherein $K^{\oplus 1}$ stands for $E^{\oplus 1}$- or $A-X^1-Y^1-Z^1-E^{\oplus}-$, A stands for a benzene, biphenyl, naphthalene, furan, benzofuran, thiophene, benzothiophene, thiazole, benzothiazole, benzimidazole, 1,3,4-thiadiazole or indole radical which, in addition to nitro, can also be substituted by $C_1$-$C_4$-alkyl, halogen, carbamoyl, sulphamoyl, cyano, hydroxyl, $C_1$-$C_4$-alkoxy or a sulpho group, $X^1$ stands for —$(CH_2)_t$—CO—, —$CH_2$—$Y^1$—GO—, —$(CH_2)_t$—$SO_2$—, —O—$CH_2$—CO—, —O—$CH_2$—$SO_2$—, —S—$CH_2$—CO—, —S—$CH_2$—$SO_2$— or a single bond, t stand for 0, 1 or 2, $X^2$ stands for —CO—, —CO—NH—CO—, —$SO_2$— or a single bond, $Y^1$ and $Y^2$ each stand for —O—, —S—, —N(R)—, —N(R)—NH— or a single bond, R stands for hydrogen, $C_1$-$C_2$-alkyl or cyanoethyl or, in $Y^1$ and $Y^2$, also for —CO— or —$SO_2$—, each of which can be bonded to the o- or periposition of A or of a benzene ring W, $Z^1$ and $Z^2$ each stand for $C_1$-$C_6$-alkylene, p-benzylene, p-xylylene or a single bond, $E^\oplus$ stands for —$N^\oplus(R^1R^2)$—,

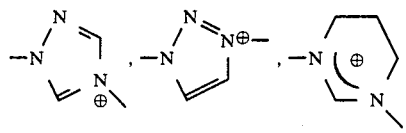

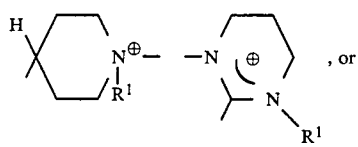

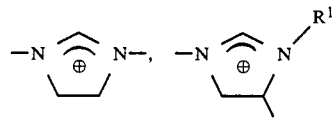

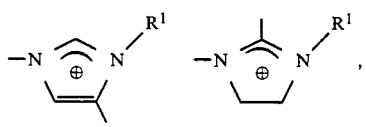

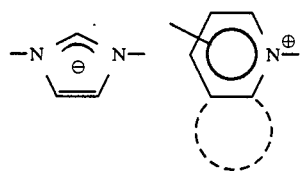

wherein
these rings can be optionally substituted by 1-4 methyl groups, and each of the two free valencies can be bonded to —$X^1$—$Y^1$—$Z^1$— or to —$Z^2$—$Y^2$—$X^2$—G—, $E^{\oplus 1}$ stands for —$N^\oplus(R^1R^2R^2)$,

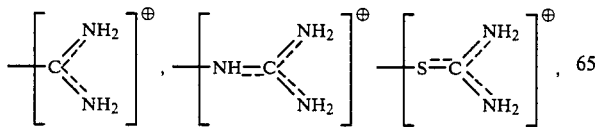

-continued

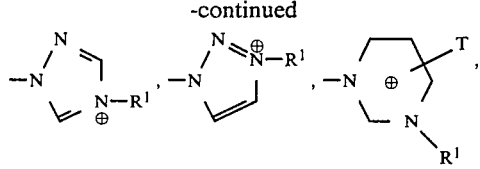

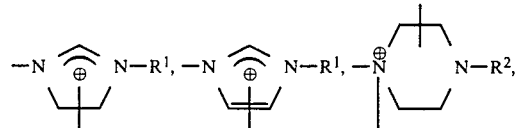

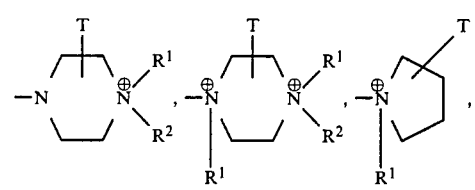

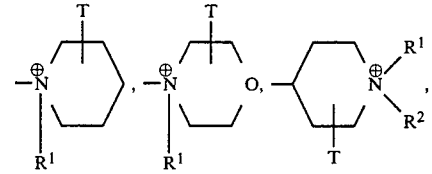

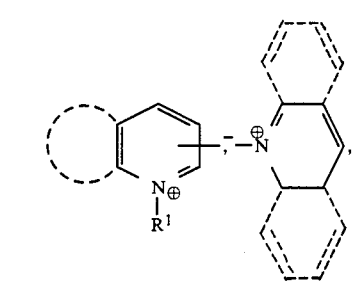

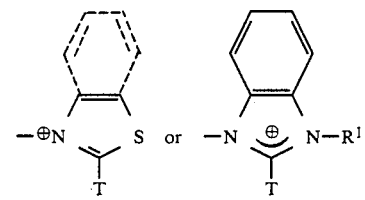

T stands for hydrogen or—depending on the nature of the ring—for 1-4 methyl groups, wherein
the aromatic radicals, in addition to 1 or 2 nitro groups, can also be substituted by $C_1$-$C_{14}$-alkyl, halogen, cyano or carbamoyl and the amidinium, guanidinium and thiuronium radicals can also be substituted by 1-2 $R^2$ radicals, $R^1$ and $R^2$, independently of each other, stand for hydrogen, $C_1$-$C_4$-alkyl, which can be substituted gy OH, $NH_2$, halogen, $C_1$-$C_4$-alkoxy, COOH, $CONH_2$, CN or $C_1$-$C_4$-alkoxycarbonyl, $C_2$-$C_4$-alkenyl, cyclohexyl, phenyl-$C_1$-$C_3$-alkyl or benzoylmethyl which, in addition to nitro, can each also be ring-substituted by $C_1$-$C_4$-alkyl, $C_1$-$C_4$-alkoxy, Cl or Br, R¹ also stands for —O]⊖ or A—X¹—Y¹—Z¹—, R and R¹ can also be cyclised and then, together with —N—Z¹—N— or —N—2^Z—N—, form a piperazine radical which is optionally substituted by 1 or 2 methyl groups, or R¹ and R² can also be cyclised and then, together with the nitrogen atom to which they are bonded, form a pyrrolidine, piperidine, morpholine or piperazine ring each of which is optionally substituted by 1 to 4 methyl groups and can be substituted on the second N atom by optionally OH— or NH₂-substituted C₁- to C₃-alkyl, G stands for —NH—, —NH—CH₂—, —O— or a single bond, W stands for an r-dentate radical from the group comprising benzene, naphthalene, anthracene, phenanthrene, 9,10-dihydrophenanthrene, cyclohexane, fluoren-9-one(3,6), thiophene(2,5), dibenzofuran(3,6), dibenzothiophene(3,6), dibenzothiophene-S-dioxide(2,7), 9-H-thioxanthene-S-dioxide(3,6), carbazole(3,6), 9-H-xanthene-9-one(2,7), 9-acridone(2,7), 1,3,4-oxadiazole(2,5), 1,2,4-oxadiazole(3,5), 1,3,4-thiadiazole(2,5), s-triazine(2,4,6), piperazine(1,4), 1,2-dihydro-1,2,4,5-tetrazine(3,6) or for a radical of the formula

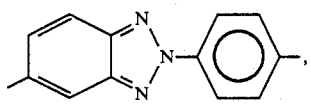

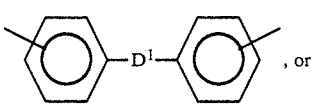, or

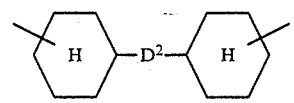

or for the case where —E⊕— denotes a bidentate pyridinium or quinolinium radical also for a single bond, D¹ and D², independently of each other, stand for a straight-chain or branched C₁-C₇-alkylene radical which is optionally interrupted by —O—, or for —O—C₂—C₄-alkylene—O—, —O—, —NH—, —N(C₁-C₂-alkyl)—, —CO—, —CO—NH—, —N-H—CO—NH—, 1,1-cyclohexylene or a direct bond, D¹ can also stand for —CH(C₆H₅)—, —CH(C₆H₄—)—, —N(C₆H₅)—, —CH=CH—, —S—, —SO₂—, —SO—, m- or p-phenylene, thiophene(2,5), 1,3,4-oxadiazole(2,5), 1,3,4-thiadiazole(2,5), oxazole(2,5), thiazole(2,5), 1,2-dihydro-1,2,4,5-tetrazine(3,6) or

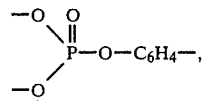

D² can also stand for —CH(C₆H₁₁)— or —CH(C₆H₁₀—)—, where the rings mentioned under W, D¹ and D², in addition to nitrogen, can also be substituted by C₁-C₄-alkyl, C₁-C₄-alkoxy, halogen and/or a sulpho group, n stands for an integer from 1 to 6, a stands for the number of anionic and/or N⊕—O⊖ groups and correspondingly for 0, 1, 2 or 3, r stands for 2 or 3 and is ≧a, and An⁻, if present, stands for a colourless anion, and wherein the chains occurring r times can be identical or different, and wherein in the case of r=2 the grouping
—E⊕—Z²—Y²—X²—G—W—G—X²—Y²—Z²—E⊕—
as a whole can also stand for

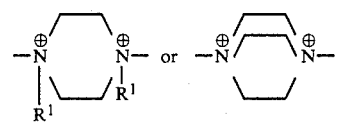

2. A process according to claim 1, wherein the compounds have the general formula

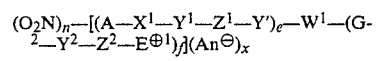

wherein
Y' stands for —O—, —S—, —NH—, —(CH₃)— or a single bond, e stands for 1, 2 or, if W¹ and/or E⊕¹ as a whole contain at least one nitro group and W¹=W, also for 0, f stands for 2 or 3, x, depending on the number of anionic and/or —N⁶¹—O⊕— groups in the molecule and depending on f, stands for 0, 1, 2 or 3, W¹ stands for

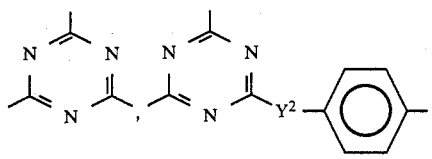

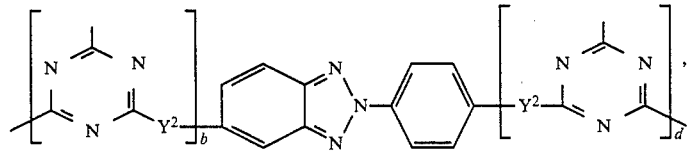

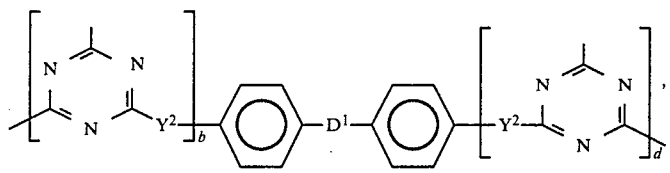

or

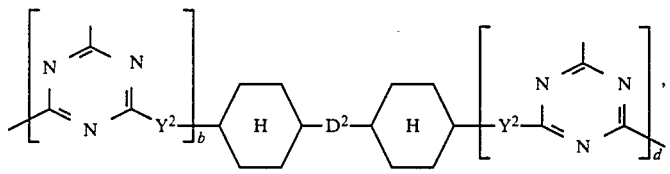

b and d stand for 0 or 1 and
G² stands for rNH—CO— or a single bond and
wherein
n, A, E⊕¹, X¹, Y¹, Y², Z¹, Z², R¹, R², x and An⊖ have the same meaning as in claim 3.

3. A process according to claim 2, wherein the compounds are oligomeric or polymeric compounds which contain per repeat unit 1–3 nitro groups and 1–2 cationic E⊕¹ groups, E⊕¹ having the same meaning as in claim 4, and wherein said compounds are obtained:

(a) by polymerisation or copolymerisation of one or more monomers from the group comprising maleic anhydride,

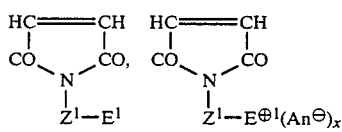

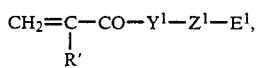

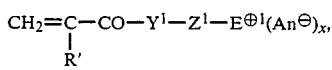

N-allylpyridinium halide or its adducts with a nitrobenzaldehyde, E¹—CH=CH₂, such as 2- or 4-vinylpyridine, and optionally in addition vinyl chloride, vinyl acetate, styrene, α-methylstyrene or 4,4′-divinylbenzene which can each be ring-substituted by methyl, chlorine, E¹—(CH₂)ᵥ—, E⊕¹—(CH₂)ᵥ— and/or nitro,
wherein
R′ stands for hydrogen or methyl,
E¹ stands for a basic group convertible by reaction with R¹L into —E⊕¹,
L stands for a group detachable as an anion and v stands for 0 or 1 and
Y¹, Z¹, E⊕¹, An⊖, x and R¹ have the above-mentioned meaning,
in the event that maleic anhydride is used as the monomer by further reaction with a compound of the formula HN(R)—Z¹E⊕¹ or HN(R)—Z¹—E¹-(An⊖)ₓ
wherein R, X¹, E¹, E⊕¹, An⊖ and x have the above-mentioned meaning,
and, if non-cationic E¹ groups are still present, by their further reaction with R¹—L, wherein
R¹ and L have the above-mentioned meaning, and optionally by subsequent mononitration or dinitration of existing aromatic groups or (b) by polycondensation of di-(C₂–C₃-alkylene)-triamines or tri-(C₂–C₃-alkylene)-tetramines of the formula

H₂N—(CH₂)ₖ—E—ᵥ(CH₂)ₖ—NH₂ wherein
k stands for 2 or 3,
w stands for 1 or 2 and
—E— stands for a basic group which can be converted into —E⊕— by reaction with R¹—L, with dicarboxylic acids of the formula

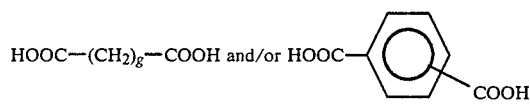

or their derivatives (such as acid chlorides, anhydrides, lower alkyl esters, hydrochlorides of the imino derivatives of lower alkyl esters or nitriles) wherein g stands for an integer from 0 to 6, and by further reaction with R¹—L,
wherein
R¹ and L have the abovementioned meaning, and optionally subsequent mononitration or dinitration of existing aromatic groups.

4. A process according to claim 3, wherein the compounds contain repeat units of the formula

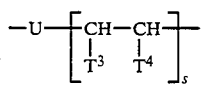

or

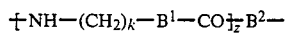

wherein
U stands for

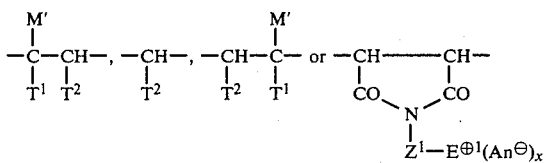

s stands for 0 or 1,
M' stands for hydrogen or methyl,
$T^1$ stands for —CO—N(R)—$Z^1$—$E^{\oplus 1}$(An$^\ominus$), or

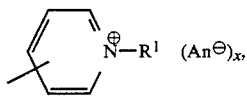

$T^2$ stands for $T^1$, COOH or—where $T^1$=

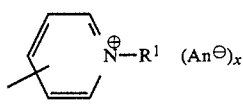

—for hydrogen,
and one of the radicals $T^3$ and $T^4$ stands for phenyl, tolyl or chlorophenyl which can each be substituted by nitro and the other stands for hydrogen or methyl,
$B^1$
(1) for

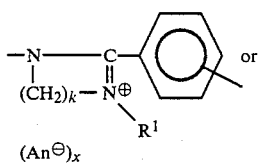

(2) for

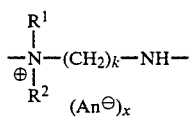

$B^2$—if $B^1$ has the meaning given under (1) and z=0 or 1—for

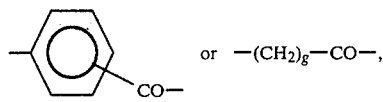

k stands for 2 or 3 and
g stands for an integer from 0 to 6 and wherein x, $Z^1$, $E^1$, $R^1$, $R^2$ and An$^\ominus$ have the same meaning as in claim 4,
the number of acid and/or —O]$^\ominus$ groups is equal to or smaller than that of the cationic charges and wherein 1 to 3 aromatically bonded nitro groups are present per repeat unit.

5. A composition for quenching the fluorescence produced by fluorescent brighteners comprising water and a virtually colorless, water-soluble, cationic or amphoteric compounds of the formula $$(O_2N)_m[(A-X^1-Y^1-Z^1-E^{\oplus 1}-Z^2-Y^2-X^2-G)_rW](r-a).An^\ominus$$

wherein
A stands for a benzene, biphenyl, naphthalene, furan, benzofuran, thiophene, benzothiophene, thiazole, benzothiazole, benzimidazole, 1,3,4-thiadiazole or indole radical which, in addition to nitro, can also be substituted by $C_1$-$C_4$-alkyl, halogen, carbamoyl, sulphamoyl, cyano, hydroxyl, $C_1$-$C_4$-alkoxy or a sulpho group,
$x^1$ stands for —(CH$_2$)$_t$—CO—, —CH$_2$—$Y^1$—CO—, —(CH$_2$)$_t$—SO$_2$—, —O—CH$_2$—CO—, —O—CH$_2$SO$_2$—, —S—CH$_2$—CO—, —S—CH$_2$—SO$_2$— or a single bond, t stands for 0, 1 or 2,
$X^2$ stands for —CO—, —CO—NH—CO—, —SO$_2$— or a single bond,
$Y^1$ and $Y^2$ each stand for —O—, —S—, —N(R)—, —N(R)—NH— or a single bond,
R stands for hydrogen, $C_1$-$C_2$-alkyl or cyanoethyl or, in $Y^1$ and $Y^2$, also for —CO— or —SO$_2$—, each of which can be bonded to the o- or peri-position of A or of a benzene ring W,
$Z^1$ and $Z^2$ each stand for $C_1$-$C_6$-alkylene, p-benzylene, p-xylylene or a single bond, $E^\oplus$ stands for —N$^\oplus$($R^1R^2$)—,

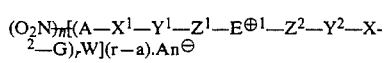

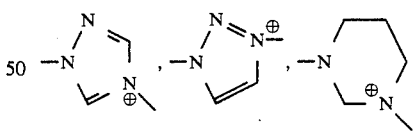

and—if $B^1$ has the meaning given under (2) and z=1—for

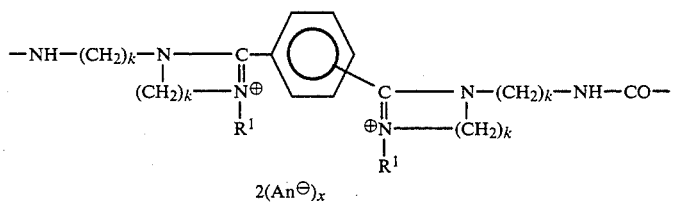

103
-continued

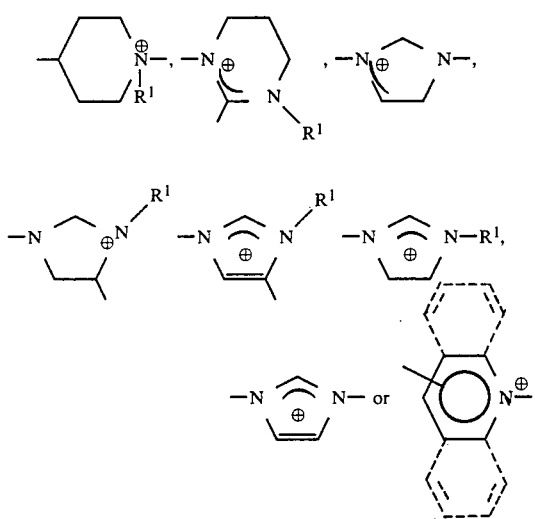

wherein
these rings can be optionally substituted by 1-4 methyl groups, and each of the two free valencies can be bonded to —$X^1$—$Y^1$—$Z^1$— or to —$Z^2$—$Y^2$—$X^2$—G—, $E^{\oplus 1}$ stands for —$N^\oplus(R^1R^2R^2)$,

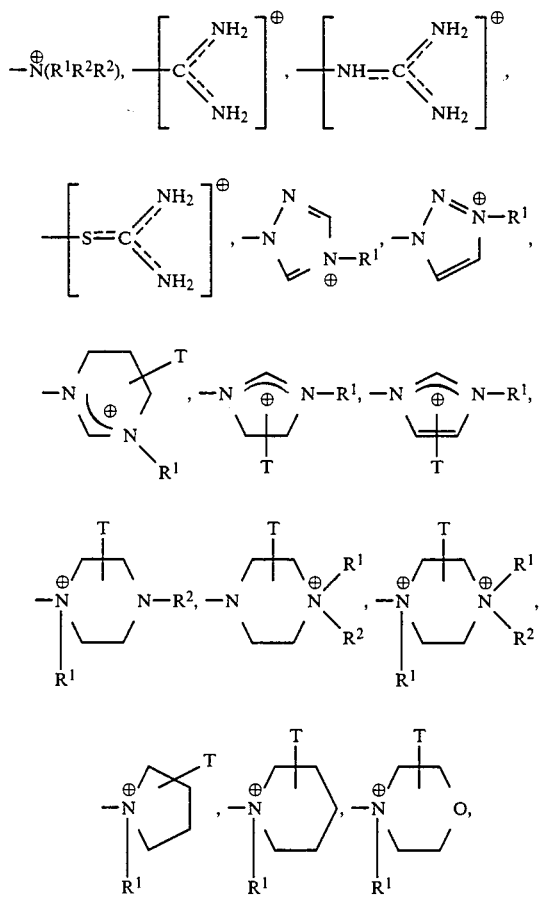

104
-continued

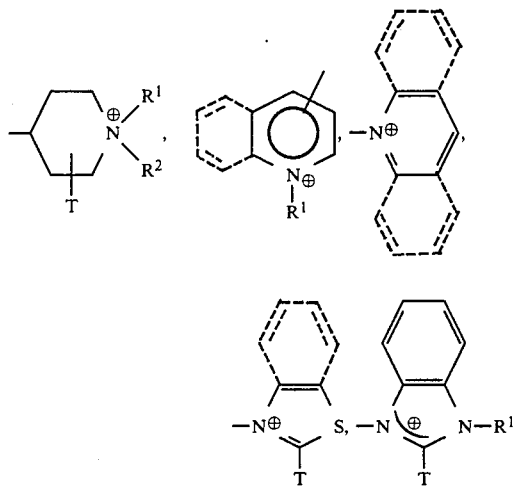

T stands for hydrogen or—depending on the nature of the ring—for 1-4 methyl groups, wherein
the aromatic radicals, in addition to 1 or 2 nitro groups, can also be substituted by $C_1$-$C_4$-alkyl, halogen, cyano or carbomoyl and the amidinium, guanidinium and thiuronium radicals can also be substituted by 1-2 $R^2$ radicals, $R^1$ and $R^2$, independently of each other, stand for hydrogen, $C_1$-$C_4$-alkyl, which can be substituted by OH, $NH_2$, halogen, $C_1$-$C_4$-alkoxy, COOH, $CONH_2$, CN or $C_1$-$C_4$-alkoxycarbonyl, $C_2$-$C_4$-alkenyl, cyclohexyl, phenyl—$C_1$-$C_3$-alkyl or benzoylmethyl which, in addition to nitro, can each also be ring-substituted by $C_1$-$C_4$-alkyl, $C_1$-$C_4$-alkoxy, Cl or Br, $R^1$ also stands for —$O]^\ominus$ or A—$X^1$—$Y^1Z^1$—, R and $R^1$ can also be cyclised and then, together with —N—$Z'$—N— or —N—4—N—, form a piperazine radical which is optionally substituted by 1 or 2 methyl groups, or $R^1$ and $R^2$ can also be cyclised and then, together with the nitrogen atom to which they are bonded, form a pyrrolidine, piperidine, morpholine or piperazine ring each of which is optionally substituted by 1 to 4 methyl groups and can be substituted on the second N atom by optionally OH— or $NH_2$-substituted $C_1$- to $C_3$-alkyl, G stands for —NH—, —NH—$CH_2$—, —O— or a single bond, W stands for an r-dentate radical from the group comprising benzene, naphthalene, anthracene, phenanthrene, 9,10-dihydrophenanthrene, cyclohexane, fluoren-9-one(3,6), thiophene(2,5), di-benzofuran(3,6), dibenzothiophene(3,6), dibenzothiophene-S-dioxide(2,7), 9-H-thioxanthene-S-dioxide(3,6), 9-H-xanthene-9-one(2,7), 9-acridone(2,7), 1,3,4-oxadiazole(2,5), 1,2,4-oxadiazole(3,5), 1,3,4-thaizizazole(2,5), s-triazine (2,4,6), piperazine(1,4), 1,2-dihydro-1,2,5-tetrazine(3,6) or for a radical of the formula

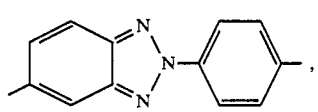

-continued

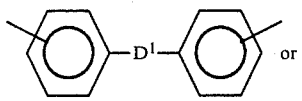 or

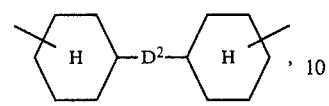, or for the case where —E⊕— denotes a bidentate pyridinium or quinolinium radical also for a single bond,
D¹ and D², independently of each other, stand for a straight-chain or branched C₁-C₇-alkylene radical which is optionally interrupted by —O—, or for —O—C₂-C₄-alkylene—O—, —O—, —NH—, —N(C₁-C₂-alkyl)—, —CO—, —CO—NH—, —N-H—CO—NH—, 1,1-cyclohexylene or a direct bond,
D¹ can also stand for —CH(C₆H₅)—, —CH(C₆H₄)—, —N(C₆H₅)—, —CH=CH—, —S—, —SO₂—, —SO—, m- or p-phenylene, thiophene(2,5), 1,3,4-oxadiazole(2,5), 1,3,4-thiadiazole(2,5), oxazole(2,5), thiazole(2,5), 1,2-dihydro-1,2,4,5-tetrazine(3,6) or

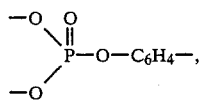,

D² can also stand for —CH(C₆H₁₁)— or —CH(C₆H₁₀—)—, where the rings mentioned under W, D¹ and D², in addition to nitrogen, can also be substituted by C₁-C₄-alkyl, C₁-C₄-alkoxy, halogen and/or a sulpho group,
n stands for an integer from 1 to 6, a stands for the number of anionic and/or N⊕—O⊖ groups and correspondingly for 0, 1, 2 or 3,
r stands for 2 or 3 and is ≧a, and
An⊖, if present, stands for a colourless anion, and wherein the chains occurring r times can be identical or different,
and wherein in the case of r=2 the grouping

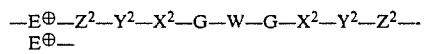

as a whole can also stand for

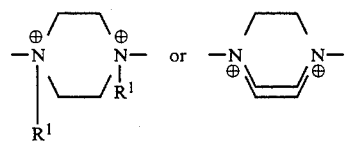

with the proviso that I is different from —CH₂— when X², Y² and G stand for a single bond, r stands for 2 and W stands for phenylene or cyclohexylene, 6. A composition for quenching the fluorescence produced by fluorescent brighteners comprising water and a virtually colorless, water-soluble, cationic or amphoteric compounds of the formula

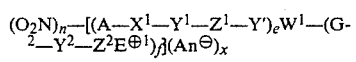

wherein
Y' stands for —O—, —S—, —NH—, —N(CH₃)— or a single bond,
e stands for 1, 2 or, if W¹ and/or E⊕¹ as a whole contain at least one nitro group and W¹=W, also for 0,
f stands for 2 or 3,
x, depending on the number of anionic and/or —N⊕—O⊖— groups in the molecule and depending on f, stands for 0, 1, 2 or 3,
W¹ stands for

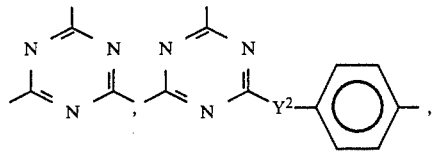

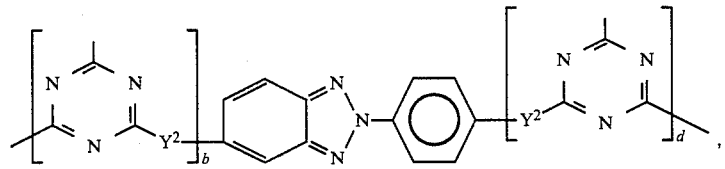,

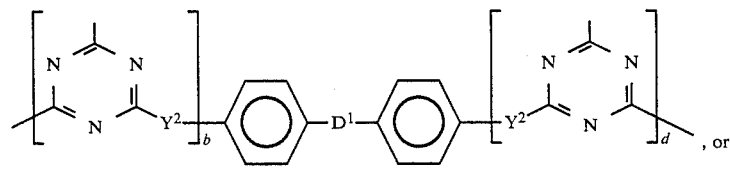, or

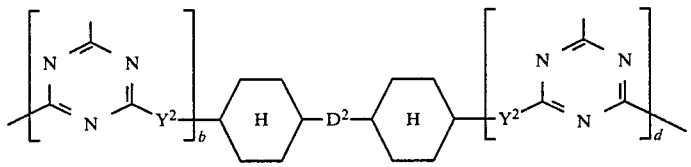

b and d stand for 0 or 1 and
G² stands for —NH—CO— or a single bond
and wherein
n, A, E⊕¹, Z¹, Y¹, Y², Z¹, Z², R¹, R² and An⊖, if present, stands for a colourless anion.

7. A composition for quenching the fluorescence produced by fluorescent brighteners comprising virtually colorless, water-soluble, cationic or amphoteric compounds which contain repeat units of the formula

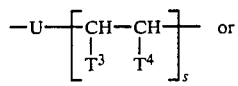

—NH—(CH₂)ₖ—B¹—CO$_z$ B²— wherein
U stands for

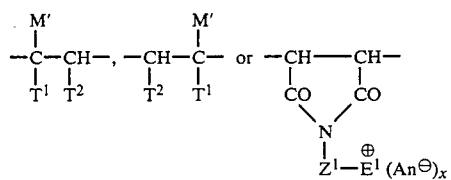

s stands for 0 or 1,
M' stands for hydrogen or methyl,
T¹ stands for —CO—N(R)—Z¹—E⊕¹(An⊖)$_x$ or

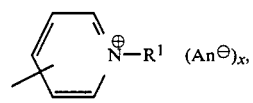

T² stands for T¹, COOH or—where T¹=

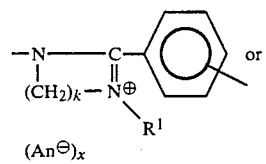

for hydrogen, and one of the radicals T³ and T⁴ stands for phenyl, toluyl or chlorophenyl which can each be substituted by nitro and the other stands for hydrogen or methyl, B¹
(1) for

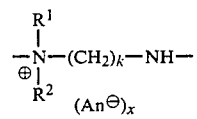

(2) for

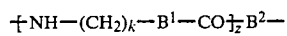

B²—if B¹ has the meaning given under (1) and z=0 or 1—for

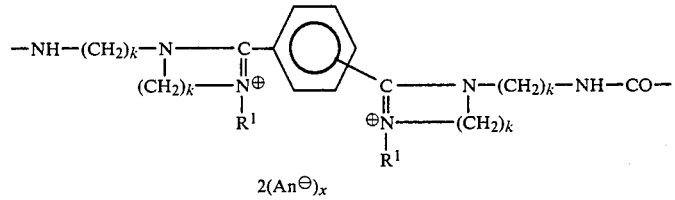

and—if B¹ has the meaning given under (2) and z=1—for

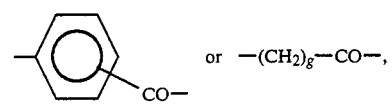

k stands for 2 or 3 and
g stands for an integer from 1 to 6 and wherein x, Z¹, E¹, R¹, R² and An⁻ have the same meaning as in claim 4,
the number of acid and/or —O]⁻ groups is equal to or smaller than that of the cationic charges and wherein 1 to 3 aromatically bonded nitro groups are present per repeat unit.

* * * * *

UNITED STATES PATENT AND TRADEMARK OFFICE
CERTIFICATE OF CORRECTION

PATENT NO. : 4,695,405

DATED : September 22, 1987

INVENTOR(S) : Horst Harnisch, et al.

It is certified that error appears in the above-identified patent and that said Letters Patent is hereby corrected as shown below:

Col. 1, line 17  Correct spelling of --oligomeric--

Col. 2, line 60 and
Col. 3, line 5   Second structure insert --  -- as follows:

Col. 4, line 56  Delete " 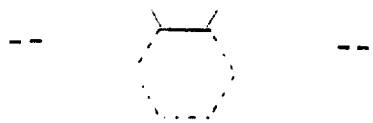 " and substitute

Col. 5, line 39  Delete dotted structure and substitute --  --

Col. 6, line 20  Middle formula delete dotted structure and substitute -- 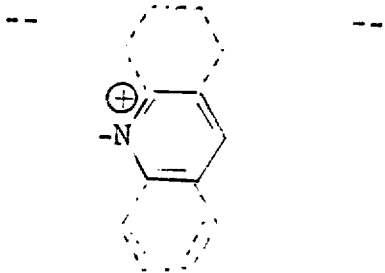 --

Col. 6, line 20  Delete third formula and substitute

Col. 6, line 30  First formula delete dotted structure and substitute --  --

UNITED STATES PATENT AND TRADEMARK OFFICE
CERTIFICATE OF CORRECTION

PATENT NO. : 4,695,405

DATED : September 22, 1987

INVENTOR(S) : Horst Harnisch, et al.

It is certified that error appears in the above-identified patent and that said Letters Patent is hereby corrected as shown below:

| | |
|---|---|
| Col. 8, line 8, Col. 98, line 21 ; Col. 106, line 3 | Delete "$\overline{z}$" and substitute --$\underline{z}$-- |
| Col. 9, line 25 | Before "$E^1$" delete "$\ominus$" and substitute --$\oplus$-- |
| Col. 14, line 37 | After "one" delete "or" and substitute --of-- |
| Col. 17, line 15 | Delete "C=N" and substitute --C$\equiv$N-- |
| Col. 18, lines 40 and 48 | End of formula delete "R" and substitute --r-- |
| Col. 39, line 5 | Correct spelling of --chloroacetamidophenyl-- |
| Col. 45-46, Examples 64 and 65 | Beginning of formula delete " $\Upsilon$ " and substitute --$\curlyvee$--; |
| Col. 45-46, Example 64 and 65 | End of formula delete " $\curlywedge$ " and substitute --$\curlywedge$-- |
| Col. 47-48, Example 68 | Insert -- -- at end of formula as follows: --$\curlywedge$-- |
| Col. 51, 52, Example 90 | Middle of formula insert --$\frown$-- as follows: --$\oplus$-- |
| Col. 55, line 50 | After "result" delete "in" and substitute --is-- |
| Col. 56, line 46 | Correct spelling of --prepared-- |
| Col. 63-64, Example 120 | End of formula after "$(CH_2)_3$—" insert --NH- -- |
| Col. 65-66, Examples 123 and 124 | Middle of top structure insert --$\smile$-- |

UNITED STATES PATENT AND TRADEMARK OFFICE
CERTIFICATE OF CORRECTION

PATENT NO. : 4,695,405

DATED : September 22, 1987

INVENTOR(S) : Horst Harnisch, et al.

It is certified that error appears in the above-identified patent and that said Letters Patent is hereby corrected as shown below:

| | |
|---|---|
| Col. 65-66, Examples 123 and 124 | Middle of bottom structure insert -- ⌒ -- as follows: as follows -- ⊕ --; |
| Col. 69-70, Example 130c | Beginning of formula after " O " insert --NH-- |
| Col. 73, line 14 | Delete second bonding line as follows: -- ⋁ -- |
| Col. 74, line 30 | Middle of formula insert -- ⌒ -- as follows -- (± -- |
| Col. 76, line 20 | After "reduced" delete "to" and substitute --in-- |
| Col. 76, line 21 | End of line delete "in" and substitute --to-- |
| Col. 83, Example 162 | Bottom of formula insert -- ⌒ -- as follows: -- ⊕ -- |
| Col. 86, Example 176 | End of formula delete " - " as follows -- C -- |
| Col. 89-90 | Last line, correct spelling of --Example-- |
| Col. 92, line 67 | Before "added" delete "was" and substitute --are-- |
| Col. 95, line 5 | End of line delete "CO-," and substitute --CO-,-- |
| Col. 95, line 50 | Second formula delete dotted structure and substitute |

UNITED STATES PATENT AND TRADEMARK OFFICE
CERTIFICATE OF CORRECTION

PATENT NO. : 4,695,405

DATED : September 22, 1987

INVENTOR(S) : Horst Harnisch, et al.

It is certified that error appears in the above-identified patent and that said Letters Patent is hereby corrected as shown below:

| | |
|---|---|
| Col. 96, line 56 | Delete "$C_{14}$-" and substitute --$C_4$- -- |
| Col. 96, line 62 | Delete "gy" and substitute --by-- |
| Col. 97, line 1 | Delete "]" and substitute --[-- |
| Col. 97, line 3 | Middle of line delete "$2^2$" and substitute --$Z^2$-- |
| Col. 98, line 44 | Delete "-($CH_3$)-" and substitute -- -$N(CH_3)$- -- |
| Col. 98, line 50 | Delete "-$N^{\oplus}$-1-$O^{\ominus}$-" and substitute -- -$\overset{\oplus}{N}$-$\overset{\ominus}{O}$- -- |
| Col. 99, line 25 | Delete "claim 3" and substitute --claim 1-- |
| Col. 99, line 30 | Delete "claim 4" and substitute --claim 2-- |
| Col. 100, line 21 | Delete "$x^1$" and substitute --$Z^1$-- |
| Col. 101, line 11 | After "(An$^{\ominus}$)" delete "," and substitute --x-- |
| Col. 102, line 50 | Third formula insert --\\-- as follows: -- \\$_{\ominus}$ -- |
| Col. 103, line 5 | Third structure delete "($\ominus$" and substitute -- $\ominus$ -- |
| Col. 103, line 10 | First formula insert --⌒-- as follows: -- ⌒ -- |
| Col. 103, lines 14-21 | Delete second formula and substitute |

UNITED STATES PATENT AND TRADEMARK OFFICE
CERTIFICATE OF CORRECTION

PATENT NO. : 4,695,405

DATED : September 22, 1987

INVENTOR(S) : Horst Harnisch, et al.

It is certified that error appears in the above-identified patent and that said Letters Patent is hereby corrected as shown below:

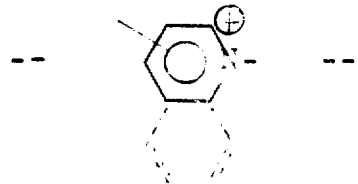

| | |
|---|---|
| Col. 104, line 27 | Correct spelling of --carbamoyl-- |
| Col. 104, line 39 | After "Y$^1$" insert -- - -- |
| Col. 104, line 41 | Delete "Z'" and substitute --Z$^1$-- |
| Col. 104, line 59 | After "(3,6)," insert --carbazole (3,6),-- |
| Col. 104, line 61 | Correct spelling of --thiadiazole-- |
| Col. 104, line 62 | Delete "1,2,5" and substitute --1,2,4,5-- |
| Col. 106, line 1 | Delete "O$^\oplus$" and substitute --O$^\ominus$-- |
| Col. 106, line 21 | Delete "I" and substitute --Z-- |
| Col. 107, line 13 | Delete "Z$^1$" and substitute --X$^1$-- (first occurrence) |

Signed and Sealed this

Fourth Day of April, 1989

Attest:

DONALD J. QUIGG

Attesting Officer

Commissioner of Patents and Trademarks